(12) United States Patent
Iris et al.

(10) Patent No.: US 6,420,111 B1
(45) Date of Patent: *Jul. 16, 2002

(54) MULTIPLEX VGID

(75) Inventors: Francois J.M. Iris, Chaville; Jean-Louis Pourny, Neuilly, both of (FR)

(73) Assignee: ValiGen (US), Inc., Newtown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/232,074

(22) Filed: Jan. 15, 1999

Related U.S. Application Data

(63) Continuation-in-part of application No. 09/007,905, filed on Jan. 15, 1998, now Pat. No. 6,221,585.

(51) Int. Cl.[7] .................... C12Q 1/68; C12P 19/34; C07H 21/04; C07H 21/00; G01N 33/543
(52) U.S. Cl. .................. 435/6; 435/97.1; 536/24.1; 536/25.4; 935/80; 436/518; 436/501; 436/528
(58) Field of Search .................. 435/6, 91.1; 536/24.1, 536/25.4; 935/80; 436/518, 501, 528

(56) References Cited

U.S. PATENT DOCUMENTS

| | | |
|---|---|---|
| 4,376,110 A | 3/1983 | David et al. |
| 4,882,269 A | 11/1989 | Schneider et al. |
| 5,334,522 A | 8/1994 | Resnick, M.A. et al. |

(List continued on next page.)

FOREIGN PATENT DOCUMENTS

| | | |
|---|---|---|
| EP | 0 370 694 | 5/1990 |
| EP | 0 596 028 | 4/1997 |
| WO | WO 89/01526 | 2/1989 |
| WO | WO 93/02216 | 2/1993 |
| WO | WO 93/20233 | 10/1993 |
| WO | WO 93/22457 | 11/1993 |
| WO | WO 95/12688 | 5/1995 |
| WO | WO 95/12689 | * 5/1995 |
| WO | WO 97/43443 | 11/1997 |
| WO | WO 99/36575 | 7/1999 |

OTHER PUBLICATIONS

Byrne et al. A screening to identify genes commonly overexpressed in carcinomas and the identification of a novel complementary DNA sequence. Cancer Research. vol. 55, pp. 2896–2903, Jul. 1995.* wieland et al. a method for difference cloning: Gene amplification following substractive hydridization. Proc. Natl. Acad. Sci. USA vol. 87, pp. 2720–2724, Apr. 1990.*

Duguid and Dinauer, 1990, "Library subtraction of in vitro cDNA libraries to identify differentially expressed genes in scrapie infection", Nucl. Acids Res. 18:2789–2792.

(List continued on next page.)

Primary Examiner—Kenneth R. Horlick
Assistant Examiner—Teresa Strzelecka
(74) Attorney, Agent, or Firm—Pennie & Edmonds LLP

(57) ABSTRACT

The present invention relates generally to the field of genomics. More particularly, the present invention relates to a method for gene identification beginning with user-selected input phenotypes. The method is referred to generally as the ValiGene[SM] Gene Identification method, or the VGID[SM] method. When more than two source populations of nucleic acids are simultaneously compared, the method may be referred to as multiplex VGID[SM]. The method employs nucleic acid mismatch binding protein chromatography to effect a molecular comparison of one phenotype with others. Genes are identified as having a specified function, or as causing or contributing to the cause or pathogenesis of a specified disease, or as associated with a specific phenotype, by virtue of their selection by the method. Identified genes may be used in development of reagents, drugs and/or combinations thereof useful in clinical or other settings for prognosis, diagnosis and/or treatment of diseases, disorders and/or conditions. The method is equally suited for gene identification for agricultural, bioengineering, medical, veterinary, and many other applications.

53 Claims, 12 Drawing Sheets

U.S. PATENT DOCUMENTS

| | | | |
|---|---|---|---|
| 5,436,142 A | | 7/1995 | Wigler et al. |
| 5,459,039 A | | 10/1995 | Modrich et al. |
| 5,482,845 A | * | 1/1996 | Soares et al. ............. 435/91.1 |
| 5,501,964 A | | 3/1996 | Wigler et al. |
| 5,556,750 A | | 9/1996 | Modrich et al. |
| 5,637,685 A | | 6/1997 | Soares et al. |
| 5,679,522 A | | 10/1997 | Modrich et al. |
| 5,702,894 A | | 12/1997 | Modrich et al. |
| 5,726,022 A | | 3/1998 | Burmer |
| 5,750,335 A | | 5/1998 | Gifford |
| 5,804,382 A | | 9/1998 | Sytkowski et al. |
| 5,830,662 A | | 11/1998 | Soares et al. |
| 5,858,659 A | | 1/1999 | Sapolsky et al. |
| 5,858,754 A | | 1/1999 | Modrich et al. |
| 5,861,482 A | | 1/1999 | Modrich et al. |
| 5,876,929 A | | 3/1999 | Wigler et al. |
| 6,033,861 A | * | 3/2000 | Schafer et al. ................ 435/6 |
| 6,221,585 B1 | | 4/2001 | Iris et al. |

OTHER PUBLICATIONS

Lisitsyn and Wigler, 1995, "Representational difference analysis in detection of genetic lesions in cancer", Meth. Enzymol. 254:291–304.

Lisitsyn et al., 1994, "Direct isolation of polymorphic markers linked to a trait by genetically directed representational difference analysis", Nature Genet. 6:57–63.

Lisitsyn et al., 1993, "Cloning the differences between two complex genomes", Science 259:946–951.

Milner et al., 1995, "A kinetic model for subtractive hybridization", Nucl. Acids Res. 23:176–187.

Wang and Brown, 1991, "A gene expression screen", Proc. Natl. Acad. Sci. USA 88:11505–11509.

Zeng et al., 1994, "Differential cDNA cloning by enzymatic degrading subtraction (EDS)", Nucl. Acids Res. 22:4381–4385.

Allen, D.J. et al., 1997, "MutS mediates heteroduplex loop formation by a translocation mechanism", EMBO J. 16:4467–4476.

Alt et al., 1978, "Selective Multiplication of Dihydrofolate Reductase Genes in Methotrexate–Resistant Variants of Cultured Murine Cells", J. Biol. Chem. 253:1357–1370.

Bellanné–Chantelot et al., 1997, "Search for DNA Sequence Variations Using a MutS–Based Technology", Mutation Research Genomics 382:35–43.

Chen, J. and Viola, M.V., 1991, "A method to detect ras point mutations in small subpopulations of cells", Analytical Biochem. 195:51–56.

Cox, E.C., 1997, "MutS, proofreading and cancer", Genetics 146:443–446.

De Wind, N. et al., 1995, "Inactivation of the mouse Msh2 gene results in mismatch repair deficiency, methylation tolerance, hyper recombination, and predisposition to cancer", Cell 82:321–330.

Drummond, J.T. et al., 1997, "DHFR/MSH3 amplification methotrexate–resistant cells alters the hMutSα/hMutSβ ratio and reduces the efficiency of base–base mismatch repair", Proc. Natl. Acad. Sci. USA 94:10144–10149.

Edelmann, W. et al., 1997, "Mutation in the Mismatch Repair Gene Msh6 Causes Cancer Susceptibility", Cell 91:467–477.

Faham, M. and Cox, D.R., 1997, "A novel in vivo method to detect DNA sequence variation", Genome Res. 5:474–482.

Fang, W. et al., 1997, "Methyl–directed repair of mismatch small heterologous sequences in cell extracts form *Escherichia coli*", JBC 36:22714–22720.

Feinstein, S.I. and Low, K.B., 1986, "Hyper–recombining recipient strains in bacterial conjugation", Genetics 113:13–33.

Fishel, R. et al., 1994, "Purified human MSH2 protein binds to DNA containing mismatched nucleotides", Cancer Res. 54:5539–5542.

Fishel, R. et al., 1993, "The human mutator gene homolog MSH2 and its association with hereditary nonpolyposis colon cancer", Cell 75:1027–1038.

Fishel, R. et al., 1994, "Binding of mismatched microsatellite DNA sequences by the human MSH2 protein", Science 266:1403–1405.

Geschwind, D.H. et al., 1996, "A biotinylated MutS fusion protein and its use in a rapid mutation screening technique", Genetic Analysis:Biomol Engineering 13:105–111.

Haber, L.T. and Walker, G.C., 1991, "Altering the conserved nucleotide binding motif in the *Salmonella typhimurium* MutS mismatch repair protein affects both its ATPase and mismatch binding activities", EMBO J. 10(9):2707–2715.

Hieter, P. and Boguski, M., 1997, "Functional Genomics: It's All How You Read It", Science 278:601–602.

Holmes, J.J. et al., 1990, "Strand–specific mismatch correction in nuclear extracts of human and *Drosophila melanogaster* cell lines", Proc. Natl. Acad. Sci. USA 87:5837–5841.

Hsu et al., 1994, "Detection of DNA Point Mutations with DNA Mismatch Repair Enzymes", Carcinogenesis 15:1657–1662.

Hunter, N. and Borts, R.H., 1997, "MIh1 is unique among mismatch repair proteins in its ability to promote crossing–over during meiosis", Genes and Development 11:1573–1582.

Iaccarino, I. et al., 1996, "MSH6, a *Saccharomyces cerevisiae* protein that binds to mismatches as a heterodimer with MSH2", Current Biology 6:484–486.

Jiricny et al., 1988, "Mismatch–Containing Oligonucleotide Duplexes Bound by the *E. coli* mutS–Encoded Protein", Nucl. Acids Res. 16:7843–7853.

Johnson, R.E. et al., 1996, "Requirements of the yeast MSH3 and MSH6 genes for MSH2–dependent genome stability", J. Biol. Chem. 271:7285–7288.

Jolly, C.J. et al., 1997, "Rapid methods for the analysis of immunoglobulin gene hypermutation: application to transgenic and gene targeted mice", Nucl. Acids Res. 25:1913–1919.

Su, S.S. et al., 1988, "Mispair specificity of methyl–directed DNA mismatch correction in vitro", J. Biol. Chem. 263:6829–6835.

Timblin et al., 1990, "Application for PCR technology to subtractive cDNA cloning: identification of genes expressed specifically in murine plasmacytoma cells", Nuc. Acid Res. 18(6): 1587–1593.

Urdea et al., 1988, "A comparison of non–radioisotopic hybridization assay methods using fluorescent, chemiluminescent and enzyme labeled synthetic oligodeoxyribonucleotide probes", Nucl. Acid Res. 16:4937–4956.

Varlet, I. et al., 1994, "Cloning and expression of the Xenopus and mouse Msh2 DNA mismatch repair genes", Nucleic Acids Res. 22(25):5723–5728.

Wagner, R. and Radman M., 1995, "Mismatch Binding Protein–Based Mutation Detection Systems", Methods, A Companion to Methods in Enzymology 7:199–203.

Wagner, R. et al., 1995, "Mutation detection using immobilized mismatch binding protein (MutS)", Nuc. Acids Res. 23(19):3944–3948.

Whitehouse, A. et al., 1997, "Analysis of the mismatch and insertion/deletion binding properties of *Thermus thermophilus*, HB8, MutS", BBRC 233:834–837.

Wu, T.H. and Marinus, M.G., 1994, "Dominant negative mutator mutations in the mutS gene of *Escherichia coli*", J. Bacteriology 176:5393–5400.

Zahrt, T.C. and Maloy, S., 1997, "Barriers to recombination between closely related bacteria: MutS and RecBCD inhibit recombination between *Salmonella typhimurium* and *Salmonella typhi*", Proc. Natl. Acad. Sci. USA 94:9786–9761.

Zeng et al., 1994, "Differential cDNA Cloning by Enzymatic Degrading Subtraction (EDS)", Nucl. Acids Res. 22:4381–4385.

Haralambidis et al., 1989, "The synthesis of polyamide—oligonucleotide conjugate molecules", Nucl. Acids Res. 18(3):493–499.

Alani, E. et al., 1995, "The *Saccharomyces cerevisiae* Msh2 protein specifically binds to duplex oligonucleotides containing mismatched DNA base pairs and insertions", Genes Dev. 9(2):234–247.

Alani, E. et al., 1997, "*Saccharomyces cerevisiae* MSH2, a mispaired base recognition protein, also recognizes Holliday junctions in DNA", J. Mol. Biol. 265:289–301.

Kolodner, R., 1996, "Biochemistry and genetics of eukaryotic mismatch repair", Cold Spring Harbor Lab. Press 10:1433–1442.

Kolodner, R. et al., 1994, "Human mismatch repair genes and their association with hereditary nonpolyposis colon cancer", Cold Spring Harbor Laboratory Proceedings, LIX, 331–338.

Lavery et al., 1997, "Selective Amplification via Biotin– and Restriction–Mediated Enrichment (SABRE), a Novel Selective Amplification Procedure for Detection of Differentially Expressed mRNAs", Proc. Natl. Acad. Sci. USA 94:6831–6838.

Leach, F.S. et al., 1993, "Mutations of a mutS homolog in hereditary nonpolyposis colorectal cancer", Cell 75:1215–1225.

Lishanski, A. et al., 1997, "Mutation detection by mismatch binding protein, mutS, in amplified DNA: application to the cystic fibrosis gene", Proc. Natl. Acad. Sci. USA 91:2674–2678.

Lu, A.L. et al., 1983, "Methyl–directed repair of DNA base pair mismatches in vitro", Proc. Natl. Acad. Sci. USA 80:4639–4643G.

Modrich, P. and Lahue, R., 1996, "Mismatch repair in replication fidelity, genetic recombination, and cancer biology", Annu. Rev. Biochem. 65:101–133.

Modrich, P., 1995, "Mismatch repair, genetic stability and tumor avoidance", Philos. Trans. R. Soc. Lond. B. Biol. Sci. 347(1319):89–95.

Myers, R. M. et al., 1985, "Detection of single base substitutions in total genomic DNA", Nature 313:495–498.

Palombo, F. et al., 1995, "GTBP, a 160–kilodalton protein essential for mismatch–binding activity in human cells", Science 268(5219):1912–1914.

Pang, P.P. et al., 1985, "Identification and characterization of the mutL gene products of *Salmonella typhimurium* LT2", J. Bacteriol. 163:1007–1015.

Papadopoulos, N. et al., 1995, "Mutations of GTBP in genetically unstable cells", Science 268(5219):1915–1917.

Parker, B.O. and Marinus, M.G., 1992, "Repair of DNA heteroduplexes containing small heterologous sequences in *Escherichia coli*", Proc. Natl. Acad. Sci. USA 89:1730–1734.

Parsons, R. et al., 1993, "Hypermutability and mismatch repair deficiency in RER+ tumor cells", Cell 75:1227–1236.

Parsons et al., 1997, "Evaluation of MutS as a tool for direct measurement of point mutations in genomic DNA", Mutat. Res. 374(2): 277–85.

Parsons, B.L. and Heflich, R.H., 1997, "Evaluations of mutS as a tool for direct measurement of point mutations in genomic DNA", Mut. Res. 374:277–285.

Patanjali, R. et al., 1991, "Construction of a uniform–abundance (normalized) cDNA library", Proc. Natl. Acad. Sci. USA 88:1943–1947.

Radman, M. and Wagner, R., 1988, "The High Fidelity of DNA Duplication", Sci. Am. 259(2):40–46.

Reitmair, A. H. et al., 1995, "MSH2 deficient mice are viable and susceptible to lymphoid tumors", Nat. Genet. 11(1):64–70.

Schar, P. et al., 1997, "Mismatch repair in *Schizosaccharomyces pombe* requires the mutL homologous gene pms1: molecular cloning and functional analysis", Genetics 146:1275–1286.

Smith J. and Modrich, P., 1997, "Removal of polymerase–produced mutant sequences from PCR products", Proc. Natl. Acad. Sci. USA 94:6847–6850.

Smith, J. and Modrich, P., 1996, "Mutation detection with MutH, MutL, and MutS mismatch repair proteins", Proc. Natl. Acad. Sci. USA 93:4374–4379.

Su, S.S. and Modrich, P., 1986,"*Escherichia coli* mutS–encoded protein binds to mismatched DNA pairs", Proc. Natl. Acad. Sci. USA 83:5057–5061.

\* cited by examiner

BLASTX

Query=         #1
       (329 letters)

Translating both strands of query sequence in all 6 reading frames

Database: Non-redundant GenBank CDS
          translations+PDB+SwissProt+SPupdate+PIR
          204,173 sequences; 58,078,033 total letters.

```
                                                                Smallest
                                                                  Sum
                                             Reading  High  Probability
Sequences producing High-scoring Segment Pairs: Frame Score  P(N)      N gi|984587          (D38582) DinP [Escherichia coli] ... -2    118  2.7e-20  2
pir||H64239        UV protection protein mucB homolo... -2    110  4.1e-16  2
gi|1303974         (D84432) YqjW [Bacillus subtilis]    -2     98  1.1e-15  2
gi|1303959         (D84432) YqjH [Bacillus subtilis]    -2    104  1.1e-15  2
sp|P34409|YLW6_CAEEL HYPOTHETICAL 59.1 KD PROTEIN F22B... -2   92  1.4e-14  2
``` gi|984587 (D38582) DinP [Escherichia coli] gi|1208981 (D83536) unknown
         [Escherichia coli]
         Length = 351

Minus Strand HSPs:

Score = 118 (54.3 bits), Expect = 2.7e-20, Sum P(2) = 2.7e-20
 Identities = 26/64 (40%), Positives = 36/64 (56%), Frame = -2

Query:   193 RGVVTTANYVARQLGIHSAMRSAEARRLAPDGIFLTPDFAKYKAISKQIHAVFRTITPKI 14
             RGV++TANY AR+ G+ SAM + A +L P    L    F YK  S  I  +F  T +I
Sbjct:    38 RGVISTANYPARKFGVRSAMPTGMALKLCPHLTLLPGRFDAYKEASNHIREIFSRYTSRI 97

Query:    13 EAVA 2 (SEQ ID NO: 7)
             E ++
Sbjct:    98 EPLS 101 (SEQ ID NO: 8)

SCORE = 100 (46.0 bits), Expect = 2.7e-20, Sum P(2) = 2.7e-20
 Identities = 19/29 (65%), Positives = 22/29 (75%), Frame = -2

Query:   307 KFXHVDIDAFYAQVEMRDNPALRHQPLII 221 (SEQ ID NO: 10)
             K HVD+D F+A VEMRDNPALR  P+ I          (SEQ ID NO: 12)
Sbjct:     3 KIIHVDMDCFFAAVEMRDNPALRDIPIAI 31 (SEQ ID NO: 11)

pir||H64239 UV protection protein mucB homolog - Mycoplasma genitalium
        (SGC3) gi|1046068 (U39720) UV protection protein [Mycoplasma
  genitalium]

FIG. 5A

Length = 411

Minus Strand HSPs:

Score = 110 (50.6 bits), Expect = 4.1e-16, Sum P(2) = 4.1e-16
Identities = 24/55 (43%), Positives = 32/55 (58%), Frame = -2

```
Query:  193 RGVVTTANYVARQLGIHSAMRSAEARRLAPDGIFLTPDFAKYKAISKQIHAVFRT 29'
            R VV+T NYVAR  GI S K  +A  L P+ IF  +F Y+ SK+I +V +
Sbjct:   53 RSVVSTCNYVARSYGIRSGMSILKALELCPNAIFAHSNFRNYRKHSKRIFSVIES 107
```

Score = 79 (36.3 bits), Expect = 4.1e-16, Sum P(2) = 4.1e-16
Identities = 15/28 (53%), Positives = 20/28 (71%), Frame = -2

```
Query:  304 FXHVDIDAFYAQVEMRDNPALRHQPLII 221 (SEQ ID NO: 16)
            F + D DAF+A VE +NP L +QPLI+
Sbjct:   20 FLYFDFDAFFASVEELENPELVNQPLIV 47 (SEQ ID NO: 17)
``` gi|1303974 (D84432) YqjW [Bacillus subtilis]
    Length = 412

Minus Strand HSPs:

Score = 98 (45.1 bits), Expect = 1.1e-15, Sum P(2) = 1.1e-15
Identities = 17/34 (50%), Positives = 26/34 (76%), Frame = -2

```
Query:  295 VDIDAFYAQVEMRDNPALRHQPLIISRDPAETGG 194 (SEQ ID NO: 19)
            VD+ +FYA VE +NP L+++P+I+S DP + GG
Sbjct:   10 VDMQSFYASVEKAENPHLKNRPVIVSGDPEKRGG 43 (SEQ ID NO: 20)
```

Score = 88 (40.5 bits), Expect = 1.1e-15, Sum P(2) = 1.1e-15
Identities = 21/60 (35%), Positives = 32/60 (53%), Frame = -2

```
Query:  190 GVVTTANYVARQLGIHSAMRSAEARRLAPDGIFLTPDFAKYKAISKQIHAVFRTITPKIE 11
            GVV  A  +A+Q G+  +A R  EA+    P+ + L P   +Y +S QI A+   T  +E
Sbjct:   43 GVVLAACPLAKQKGVVNASRLWEAQEKCPEAVVLRPRMQRYIDVSLQITAILEEYTDLVE 102
``` gi|1303959 (D84432) YqjH [Bacillus subtilis]
    Length = 414

Minus Strand HSPs:

Score = 104 (47.8 bits), Expect = 1.1e-15, Sum P(2) = 1.1e-15
Identities = 21/64 (32%), Positives = 37/64 (57%), Frame = -2

```
Query:  193 RGVVTTANYVARQLGIHSAMRSAEARRLAPDGIFLTPDFAKYKAISKQIHAVFRTITPKI 14
            +G+V T +Y AR  G+ + M  +A+R  P+ I L P+F +Y+ S+ +  +R  T  +
Sbjct:   43 KGIVVTCSYEARARGVKTTMPVWQAKRHCPELIVLPPNFDRYRNSSRAMFTILREYTDLV 102
```

FIG. 5B

BLASTX

Query=          Tor-M
         (256 letters)

Translating both strands of query sequence in all 6 reading frames

Database:  Non-redundant GenBank CDS
           translations+PDB+SwissProt+SPupdate+PIR
           221,464 sequences; 63,648,287 total letters.

```
                                                              Smallest
                                                                Sum
                                            Reading  High  Probability
Sequences producing High-scoring Segment Pairs:  Frame  Score   P(N)     N gi|1303959        (D84432) YqjH [Bacillus subtilis]    +1    93   0.00011   1
gi|984587         (D38582) DinP [Escherichia coli] ... +1    90   0.00034   1
``` gi|1303959 (D84432) YqjH [Bacillus subtilis]
           Length = 414

Plus Strand HSPs:

Score = 93 (42.8 bits), Expect = 0.00011, P = 0.00011
Identities = 19/50 (38%), Positives = 28/50 (56%), Frame = +1

Query:    22 IFLTPDFAKYKAISKQIHAVFRTITPKIEPVVIDEAYLDVTANALSGALL 171 (SEQ ID NO: 25)
             I L P+F +Y+ S+ + + R T +EPV IDE Y+D+T    S   L
Sbjct:    75 IVLPPNFDRYRNSSRAMFTILREYTDLVEPVSIDEGYMDMTDTPYSSRAL 124 (SEQ ID NO: 26)

gi|984587 (D38582) DinP [Escherichia coli] gi|1208981 (D83536) unknown
           [Escherichia coli] gi|1552799 (U70214) DinP [Escherichia coli]
           Length = 351

Plus Strand HSPs:

Score = 90 (41.4 bits), Expect = 0.00034, P = 0.00034
Identities = 18/35 (51%), Positives = 22/35 (62%), Frame = +1

Query:    40 FAKYKAISKQIHAVFRTITPKIEPVVIDEAYLDVT 144 (SEQ ID NO: 27)
             F YK S I +F  T +IEP+ +DEAYLDVT           (SEQ ID NO: 29)
Sbjct:    76 FDAYKEASNHIREIFSRYTSRIEPLSLDEAYLDVT 110 (SEQ ID NO: 28)

FIG. 6

BLASTX

Query=        # 3
        (248 letters)

Translating both strands of query sequence in all 6 reading frames

Database: Non-redundant GenBank CDS
          translations+PDB+SwissProt+SPupdate+PIR
          204,173 sequences; 58,078,033 total letters.

|  |  | Reading Frame | High Score | Smallest Sum Probability P(N) | N |
|---|---|---|---|---|---|
| Sequences producing High-scoring Segment Pairs: |  |  |  |  |  |
| gi\|984587 | (D38582) DinP [Escherichia coli] ... | +3 | 128 | 3.2e-14 | 2 |
| gi\|1303959 | (D84432) YqjH [Bacillus subtilis] | +3 | 121 | 1.9e-12 | 2 |
| pir\|\|H64239 | UV protection protein mucB homolo... | +3 | 88 | 6.5e-05 | 1 | gi|984587 (D38582) DinP [Escherichia coli] gi|1208981 (DS83536) unknown
    [Escherichia coli]
    Length = 351

Plus Strand HSPs:

Score = 128 (58.3 bits), Expect = 3.2e-14, Sum P(2) = 3.2e-14
  Identities = 28/69 (40%), Positives = 40/69 (57%), Frame = +3

Query:    39  SGAXLAAQLRHDIYKQXRLTSSVGVSYNKLLAKLGSXFNKPNGVTVITXENRLXFLXHXP  218
              S  +A ++R  I+ +  +LT+S GV+  K LAK+ S  NKPNG VIT    FL   P
Sbjct:   118  SATLIAQEIRQTIFNELQLTASAGVAPVKFLAKIASDMNKPNGQFVITPAEVPAFLQTLP  177

Query:   219  IGEFRGVGE  245   (SEQ ID NO: 30)
              + +  GVG+
Sbjct:   178  LAKIPGVGK  186   (SEQ ID NO: 31)

Score = 48 (21.8 bits), Expect = 3.2e-14, Sum P(2) = 3.2e-14
  Identities = 9/10 (90%), Positives = 10/10 (100%), Frames = +3

Query:     3  DEAYLDVTDN  32   (SEQ ID NO: 33)
              DEAYLDVTD+              (SEQ ID NO: 35)
Sbjct:   103  DEAYLDVTDS  112  (SEQ ID NO: 34)

gi|1303959 (D84432) YqjH [Bacillus subtilis]
    Length = 414

FIG. 7A

Plus Strand HSPs:

Score = 121 (55.1 bits), Expect = 1.9e-12, Sum P(2) = 1.9e-12
Identities = 24/65 (36%), Positives = 38/65 (58%), Frame = +3

Query:   54 AAQLRHDIYKQXRLTSSVGVSYNKLLAKLGSXFNKPNGVTVITXENRLXFLXHXPIGEFR 233
            A +++  + K+ L SS+G++ NK LAK+ S   KP G+T++        L  P+GE
Sbjct:  127 AKEIQSRLQKELLLPSSIGIAPNKFLAKMASDMKKPLGITILRKRQVPDILWPLPVGEMH 186

Query:  234 GVGEK 248 (SEQ ID NO: 36)
            GVG+K
Sbjct:  187 GVGKK 191 (SEQ ID NO: 37)

Score = 43 (19.6 bits), Expect = 1.9e-12, Sum P(2) = 1.9e-12
Identities = 8/17 (47%), Positives = 10/17 (58%), Frame = +3

Query:    3 DEAYLDVTDNALSGAXL 53 (SEQ ID NO: 38)
            DE Y+D+TD    S  L
Sbjct:  108 DEGYMDMTDTPYSSRAL 124 (SEQ ID NO: 39)

pir||H64239 UV protection protein mucB homolog - Mycoplasma genitalium
      (SGC3) gi|1046068 (U39720) UV protection protein [Mycoplasma
genitalium]
      Length = 411

Plus Strand HSPs:

Score = 88 (40.1 bits), Expect = 6.5e-05, P = 6.5e-05
Identities = 20/66 (30%), Positives = 39/66 (59%), Frame = +3

Query:   51 LAAQLRHDIYKQXRLTSSVGVSYNKLLAKLGSXFNKPNGVTVITXENRLXFLXHXPIGEF 230
            +A +++ +++  R+ S+G+S + L+AK+ S   KP G+   + ++   L  PI E
Sbjct:  136 IAKKIKNFVFQNLRIKISIGISDHFLIAKIFSNQAKPFGIKSCSVKDIKKKLWPLPITEI 195

Query:  231 RGVGEK 248 (SEQ ID NO: 40)
             G+GEK
Sbjct:  196 PGIGEK 201 (SEQ ID NO: 41)

sp|P18642|IMPB_SALTY IMPB PROTEIN. pir||JQ0661 impB protein -
      Salmonella typhimurium plasmid TP110 gi|47748 (X53528) impB gene
      product (AA 1-424) [Salmonella typhimurium]
      Length = 424

Plus Strand HSPs:

Score = 49 (22.3 bits), Expect = 0.00024, Sum P(3) = 0.00024
Identities = 12/37 (32%), Positives = 18/37 (48%), Frame = +3

FIG.7B

BLASTX

Query=    *1
          (388 letters)

Translating both strands of query sequence in all 6 reading frames

Database: Non-redundant GenBank CDS
          translations+PDB+SwissProt+SPupdate+PIR
          258,816 sequences; 73,256,548 total letters.
Searching.............................................done

```
                                                           Smallest
                                                             Sum
                                              Reading  High  Probability
Sequences producing High-scoring Segment Pairs: Frame  Score  P(N)    N gi|984587          (D38582) DinP [Escherichia coli] ... +3   115  9.8e-11  2
sp|P54545|YQJH_BACSU HYPOTHETICAL 47.0 KD PROTEIN IN G... +3 108  4.6e-08  2
gi|1706953         (U52110) Dbh [Sulfolobus solfator... +3   99   6.0e-06  2
sp|P54560|YQJW_BACSU HYPOTHETICAL 45.9 KD PROTEIN IN G... +3 101  4.3e-05  1
sp|P34409|YLW6_CAEEL HYPOTHETICAL 59.1 KD PROTEIN F22B... +3 82   0.0014   2
gnl|PID|e290932    (Z83866) unknown [Mycobacterium t... +3   84   0.0043   2
``` gi|984587 (D38582) DinP [Escherichia coli] gnl|PID|d1012651 (D3536)
    unknown [Escherichia coli] gi|1552799 (U70214) DinP [Escherichia
    coli] gi|1786425 (AE000131) hypothetical protein DinP [Escherichia
    coli]
    Length = 351

Plus Strand HSPs:

Score = 115 (52.9 bits), Expect = 2.9e-10, Sum P(2) = 2.9e-10
Identities = 26/61 (42%), Positives = 34/61 (55%), Frame = +3

Query:   3 QLGIHSAMRSAEARRLAPDGIFLTPDFAKYKAISKQIHAVFRTITPKIEAVALDEAYLDV 182
           + G+ SAM + A +L P    L F YK S I +F  T +IE ++LDEAYLDV
Sbjct:  50 KFGVRSAMPTGMALKLCPHLTLLPGRFDAYKEASNHIREIFSRYTSRIEPLSLDEAYLDV 109

Query: 183 T 185 (SEQ ID NO: 42)
           T
Sbjct: 110 T 110 (SEQ ID NO: 43)

Score = 47 (21.6 bits), Expect = 9.8e-11, Sum P(2) = 9.8e-11
Identities = 12/41 (29%), Positives = 20/41 (48%), Frame = +2

Query: 218 QLRHDIYIHTRLL*FGGCIVYHTISEVGI*FNKPNGVTVIT 340 (SEQ ID NO: 45)
           ++R I+  +L   G       +++   NKPNG VIT
Sbjct: 125 EIRQTIFNELQLTASAGVAPVKFLAKIASDMNKPNGQFVIT 165 (SEQ ID NO: 46)

Score = 47 (21.6 bits), Expect = 2.9e-10, Sum P(2) = 2.9e-10

FIG. 8A

Identities = 12/38 (31%), Positives = 18/38 (47%), Frame = +3

```
Query:  198 SGALLAHSYGMTFIYTHDYSSSVGVSYTILLAKLGSDL 311 (SEQ ID NO: 48)
              S L+A   T      ++S GV+    LAK+ SD+
Sbjct:  118 SATLIAQEIRQTIFNELQLTASAGVAPVKFLAKIASDM 155 (SEQ ID NO: 49)
``` sp|P54545|YQJH_BACSU HYPOTHETICAL 47.0 KD PROTEIN IN GLNQ-ANSR
    INTERGENIC REGION gnl|PID|d1013294 (084432) YqjH [Bacillus subtilis]
    Length = 414

Plus Strand HSPs:

Score = 108 (49.7 bits), Expect = 4.6e-08, Sum P(2) = 4.6e-08
Identities = 22/68 (32%), Positives = 38/68 (55%), Frames = +3

```
Query:    9 GIHSAMRSAEARRLAPDGIFLTPDFAKYKAISKQIHAVFRTITPKIEAVALDEAYLDVTA 188
              G+ + M   +A+R P+ I L P+F +Y+  S+ +  + R  T  +E V++DE Y+D+T
Sbjct:   57 GVKTTMPVWQAKRHCPELIVLPPNFDRYRNSSRAMFTILREYTDLVEPVSIDEGYMDMTD 116

Query:  189 NALSGALL 212 (SEQ ID NO: 50)
                S L
Sbjct:  117 TPYSSRAL 124 (SEQ ID NO: 51)
```

Score = 42 (19.3 bits), Expect = 4.6e-08, Sum P(2) = 4.6e-08
Identities = 8/18 (44%), Positives = 13/18 (72%), Frame = +3

```
Query:  258 SSVGVSYTILLAKLGSDL 311 (SEQ ID NO: 52)
              SS+G++    LAK+ SD+
Sbjct:  142 SSIGIAPNKFLAKMASDM 159 (SEQ ID NO: 53)
``` gi|1706953 (U52110) Dbh [Sulfolobus solfataricus]
    Length = 354

Plus Strand HSPs:

Score = 99 (45.5 bits), Expect = 6.0e-06, Sum P(2) = 6.0e-06
Identities = 22/61 (36%), Positives = 35/61 (57%), Frames = +3

```
Query:    3 QLGIHSAMRSAEARRLAPDGIFLTPDFAKYKAISKQIHAVFRTITPKIEAVALDEAYLDV 182
              +LG+ + M   +A ++AP I++       Y+A S +I      KIE ++DEAYLDV
Sbjct:   52 KLGVKAGMPIIKAMQIAPSAIYVPMRKPIYEAFSNRIMNLLNKHADKIEVASIDEAYLDV 111

Query:  183 T 185 (SEQ ID NO: 54)
              T
Sbjct:  112 T 112 (SEQ ID NO: 55)
```

Score = 37 (17.0 bits), Expext = 6.0e-06, Sum P(2) = 6.0e-06
Identities = 12/43 (27%), Positives = 20/43 (46%), Frame = +3

```
Query:  180 VTANALSGALLAHSYGMTFIYTHDYSSSVGVSYTILLAKLGSD 308 (SEQ ID NO: 57)
              V  N +G LA     +   + +VGV+   +LAK+ +D
Sbjct:  115 VEGNFENGIELARKIKQEILEKEKITVTGVAPNKILAKIIAD 157 (SEQ ID NO: 58)
```

FIG. 8B

BLASTX

Query= #2
(383 letters)

Translating both strands of query sequence in all 6 reading frames

Database: Non-redundant GenBank CDS
translations+PDB+SwissProt+SPupdate+PIR
258,816 sequences; 73,256,548 total letters.
Searching..............................................done

```
                                                              Smallest
                                                                Sum
                                             Reading  High  Probability
Sequences producing High-scoring Segment Pairs:  Frame  Score  P(N)      N sp|P54545|YQJH_BACSU HYPOTHETICAL 47.0 KD PROTEIN IN G...  +1   83   8.6e-07  2
gi|984587            (D38582) DinP [Escherichia coli] ...  +1   82   1.7e-05  2
``` sp|P54545|YQJH_BACSU HYPOTHETICAL 47.0 KD PROTEIN IN GLNQ-ANSR
INTERGENIC REGION gnl|PID|d1013294 (D84432) YqjH [Bacillus subtilis]
Length = 414

Plus Strand HSPs:

Score = 83 (38.2 bits), Expect = 8.6e-07, Sum P(2) = 8.6e-07
Identities = 16/41 (39%), Positives = 25/41 (60%), Frame = +1

Query:     61 IFLTPDFAKYKAISKQIHAVFRTITPKIEAVVIDEAYLDVT 183 (SEQ ID NO: 69)
              I L P+F +Y+ S+ +  + R T +E V IDE Y+D+T
Sbjct:     75 IVLPPNFDRYRNSSRAMFTILREYTDLVEPVSIDEGYMDMT 115 (SEQ ID NO: 70)

Score = 59 (27.1 bits), Expect = 8.6e-07, Sum P(2) = 8.6e-07
Identities = 11/20 (55%), Positives = 16/20 (80%), Frame = +1

Query:    247 LTSSVGVSYNKLLAKLGSDL 306 (SEQ ID NO: 59)
              L SS+G++ NK LAK+ SD+
Sbjct:    140 LPSSIGIAPNKFLAKMASDM 159 (SEQ ID NO: 60)

gi|984587 (D38582) DinP [Escherichia coli] gnl|PID|d1012651 (D83536)
unknown [Escherichia coli] gi|1552799 (U70214) DinP [Escherichia
coli] gi|1786425 (AE000131) hypothetical protein DinP [Escherichia
coli]
Length = 351

Plus Strand HSPs:

Score = 82 (37.7 bits), Expect = 1.7e-05, Sum P(2) = 1.7e-05

FIG. 9A

Identities = 17/35 (48%), Positives = 21/35 (60%), Frame = +1

Query:   79 FAKYKAISKQIHAVFRTITPKIEAVVIDEAYLDVT 183 (SEQ ID NO: 61)
            F YK  S  I  +F   T +IE +  +DEAYLDVT
Sbjct:   76 FDAYKEASNHIREIFSRYTSRIEPLSLDEAYLDVT 110 (SEQ ID NO: 62)

Score = 51 (23.5 bits), Expect = 1.7e-05, Sum P(2) = 1.7e-05
Identities = 11/20 (55%), Positives = 15/20 (75%), Frame = +1

Query:  247 LTSSVGVSYNKLLAKLGSDL 306 (SEQ ID NO: 64)
            LT+S GV+  K LAK+ SD+
Sbjct:  136 LTASAGVAPVKFLAKIASDM 155 (SEQ ID NO: 65)

Score = 40 (18.4 bits), Expect = 0.00079, Sum P(2) = 0.00079
Identities = 8/18 (44%), Positives = 12/18 (66%), Frame = +3

Query:  282 ISEVGI*FNKPNGVTVIT 335 (SEQ ID NO: 66)
            ++++    NKPNG VIT
Sbjct:  148 LAKIASDMNKPNGQFVIT 165 (SEQ ID NO: 67)

FIG. 9B

MULTIPLEX VGID

This application is a continuation-in-part of U.S. patent application Ser. No. 09/007,905 entitled "METHOD FOR IDENTIFYING GENES UNDERLYING DEFINED PHENOTYPES" filed Jan. 15, 1998, now U.S. Pat. No. 6,221,585 which is incorporated herein by reference in its entirety.

1. FIELD OF THE INVENTION
2. BACKGROUND OF THE INVENTION
   2.1. CHARACTERISTICS OF DISEASE AND OTHER PHENOTYPES
   2.2. GENE IDENTIFICATION BY POSITIONAL CLONING
      2.2.1. LINKAGE MAPPING
      2.2.2. CHROMOSOMAL LOCALIZATION
      2.2.3. FURTHER REFINEMENT
      2.2.4. FROM LOCUS TO GENE
   2.3. MISMATCH REPAIR
3. SUMMARY OF THE INVENTION
4. BRIEF DESCRIPTION OF THE DRAWINGS
5. DETAILED DESCRIPTION OF THE INVENTION
   5.1. GENETIC HETEROGENEITY
      5.1.1. GENETIC HETEROGENEITY IN CELL LINES
      5.1.2. GENETIC HETEROGENEITY IN TISSUES
   5.2. TWO APPROACHES FOR THE VGID[SM] METHOD
      5.2.1. FIRST APPROACH: CELL LINES OR SOLE TISSUE SAMPLE
      5.2.2. SECOND APPROACH: SAMPLES FROM ORGANISMS HAVING CONSANGUINITY
   5.3. MISCELLANEOUS METHODS USED IN CONJUNCTION WITH THE VGID[SM] METHOD
      5.3.1. DNA AMPLIFICATION
      5.3.2. ADJUSTING STRINGENCY
   5.4. PHENOTYPE SELECTION TO OPTIMIZE THE VGID[SM] METHOD
      5.4.1. TISSUE SAMPLE COLLECTION
      5.4.2. CELL CULTURE
   5.5. TROUBLESHOOTING THE VGID[SM] METHOD
   5.6. ASSAYS FOR PHENOTYPE SELECTION
   5.7. DISEASES, DISORDERS, AND OTHER PHENOTYPES
   5.8. LINKING OLIGONUCLEOTIDES TO SPECIFIC BINDING LIGANDS
   5.9. ANTIBODIES AND DERIVATIVES THEREOF
   5.10. ANTIBODY COLUMNS FOR SORTING NUCLEIC ACIDS
   5.11. DETECTION OF ANTIBODIES AGAINST PEPTIDE-LABELED OLIGONUCLEOTIDES
6. EXAMPLE: USE OF THE VGID[SM] METHOD TO IDENTIFY hDinP GENES
   6.1. INTRODUCTION
   6.2. MATERIALS AND METHODS
   6.3. RESULTS
   6.4. DISCUSSION
   6.5. APPLICATION OF THE VGID[SM] METHOD TO A COMPLEX, MULTISTAGE SYSTEM
      6.5.1. EXAMPLE OF A COMPLEX SYSTEM-BREAST CANCER
      6.5.2. ANALYSIS OF A COMPLEX SYSTEM USING MULTIPLEX VGID[SM]

1. FIELD OF THE INVENTION

The present invention relates generally to the field of genomics. More particularly, the present invention relates to a method for gene identification beginning with user-selected input phenotypes. The method is referred to generally as the ValiGene[SM] Gene Identification method, or the VGID[SM] method. The method employs nucleic acid mismatch binding protein chromatography to effect a molecular comparison of one phenotype with others. Genes are identified as having a specified function, or as causing or contributing to the cause or pathogenesis of a specified disease, or as associated with a specific phenotype, by virtue of their selection by the method. Identified genes may be used in development of reagents, drugs and/or combinations thereof useful in clinical or other settings for prognosis, diagnosis and/or treatment of diseases, disorders and/or conditions. The method is equally suited for gene identification for agricultural, bio-engineering, medical, veterinary, and many other applications. When more than two source populations of nucleic acids are simultaneously compared, the method may be referred to as multiplex VGID[SM].

2. BACKGROUND OF THE INVENTION

Identification of a particular genotype responsible for a given phenotype is an essential goal underlying gene-based medicine because it affords a rational departure point for the development of successful strategies for disease management, therapy and even cure. While, by one recent estimate, only two percent (2%) of the human genome has yet been sequenced, perhaps more than 50% of expressed human genes are at least partially represented in existing databases (Duboule, D., Oct. 24, 1997, Editorial: The Evolution Of Genomics, *Science* 278, 555). It is therefore quite clear that understanding functional interactions among the products of expressed genes represents the next great challenge in medicine and biology. This pursuit has been referred to as "functional genomics," although this term is perhaps too broad to have a clear meaning (Heiter, P. and Boguski, M., Oct. 24, 1997, Functional Genomics: It's All How You Read It, *Science* 278, 601–602). Nevertheless, it is the prevailing view that functional genomics generally describes " . . . a transition or expansion from the mapping and sequencing of genomes . . . to an emphasis on genome function." (Id.). Further, this new emphasis will require " . . . creative thinking in developing innovative technologies that make use of the vast resource of structural genomics information." Perhaps the best definition of functional genomics is " . . . the development and application of global (genome-wide or system-wide) experimental approaches to assess gene function by making use of the information provided by structural genomics." (Id., emphasis added).

One of the major advantages of the present invention is the circumvention of large-scale sequencing in determining functional relationships among genes. The VGID[SM] method of the present invention is a straightforward yet very powerful genetic comparison or subtraction technique. Functional information is obtained from global (i.e. genome-wide) expressed gene comparison of two or more user-defined phenotypes using mismatch binding protein chromatography. With the VGID[SM] method, disease genes may be identified over a time period of weeks, unlike the years required to succeed using positional cloning.

2.1. Characteristics of Disease and Other Phenotypes

Genetic diseases and other genetically-determined phenotypes, irrespective of mode of inheritance, can be due to single or multiple lesions (i.e. mutations) affecting one gene or more than one gene simultaneously. Genetic heterogeneity (i.e. a difference in DNA sequence), by definition, characterizes all diseases which have a genetic component. Genetic diseases can be further categorized among four broad genotypic groups, as described below.

A mono-allelic disease is characterized as having a mutation in a single allele of a single gene. This disease group is the simplest in terms of genetic analysis since mono-allelic diseases arise, by definition, from a unique lesion affecting a single gene. Mono-allelic diseases have also been described as displaying "molecular monomorphism," which is another way of saying that a single molecular defect in a single gene accounts for the disease phenotype. Since such genetic lesions are unique, they are invariably "causative" of the disease in question. For a mono-allelic disease, only a few affected individuals need to undergo genetic analysis to attribute a given mutation to a disease phenotype. That is, large familial studies are not required to identify the disease-causing gene. Only a few examples of such diseases are known. One example is sickle cell anemia, which is due to a single base substitution (i.e. A→T) in the gene encoding hemoglobin. This base substitution changes the respective codon from GAG to GTG, ultimately resulting in a glutamate-to-valine amino acid substitution at position six of the hemoglobin β chain molecule and the characteristic, devastating sickle-shaped erythrocyte.

A polyallelic disease is characterized as having several different mutations arising independently in a single gene. Here, each independent mutation event gives rise to a different disease allele. A significant proportion of all genetic disease is thought to result in this way. Because such de novo mutations are so frequent, polyallelism is a very common characteristic of genetic disease. Duchenne's muscular dystrophy (DMD), Becker's myopathy, and cystic fibrosis (CF) are well-known examples of polyallelic diseases (see e.g. McKusick, Mendelian Inheritance in Man, Catalog of Autosomal Dominant, Autosomal Recessive, and X-Linked Phenotypes, 10th Edition, 1992, The Johns Hopkins University Press, Baltimore, Md.). Polyallelism may arise in at least two ways. First, each new case of a disease may arise from an independent mutation event in the target gene. For example, in DMD, at least 30% of cases present novel mutations in the dystrophin gene which differ from all previously-characterized mutations. Second, selective fixation of different founder-effect mutations contributes to the occurrence of polyallelism. One example of this is the β-thallasemias in which the world population of affected individuals presents remarkably high polyallelism, but local populations are characterized by limited allelic heterogeneity.

Non-allelic genetic disease is characterized as having more than one candidate gene. Here, a genetic disease which is clinically well-defined may be due to a lesion (mutation) of any one gene among several candidate genes. For example, imperfect osteogenesis is caused by lesion of any one of five distinct type 1 collagen genes. However, the identification of candidate genes for a non-allelic genetic disease is made more difficult when the several candidate genes, unlike the collagen genes, are not related in sequence. For example, pituitary dwarfism is physiologically due to hyperfunction of the anterior pituitary gland. In a minority of pituitary dwarfism cases, the causative lesion has been traced to the gene complex elaborating growth hormone (Kaplan and Delpech, 1993, in Molecular Biology and Medicine, 2nd ed., Médecine-Sciences Flammarion, Paris, Chap. 12, pp. 307–308). In the vast majority of cases, however, these genes are perfectly normal and the causative disease loci are not even linked to the growth hormone complex (as demonstrated by polymorphism linkage studies, Id.). Therefore, other unidentified genes comprising alleles not related to growth hormone account for the majority of pituitary dwarfism cases. Such non-allelic diseases clearly require more than just linkage analysis to identify all of the involved genes. The VGID[SM] method of the present invention provides a rapid, rational way of approaching this problem.

A polygenic disease is characterized as having several abnormal genes acting concurrently to produce a pathologic phenotype. This group includes many genetic diseases often described as "multifactorial disorders." Examples include diabetes mellitus, hypertension, atherosclerosis, autoimmune disorders, and many others. For the majority of polygenic diseases, the metabolic complexities are so great that a rational basis on which candidate genes could be identified may not have existed before the invention set forth herein. In the few instances where a candidate gene has been suggested, this knowledge has still proven largely inadequate to identify susceptible individuals, or to explain pathogenesis.

The last two groups of genetic disorders described above (i.e. non-allelism and polygenism) represent the greatest challenge currently facing human and veterinary medicine. Because of an absence of sufficient biochemical and physiological data, credible candidate genes have largely gone unidentified. This absence of credible candidate genes has, in turn, ruled out the possibility of identifying susceptible individuals and attempting preventive intervention before symptoms appear. The invention set forth herein provides one way to overcome these limitations by identifying credible candidate genes.

2.2. Gene Identification by Positional Cloning

There are several known methods available to identify candidate disease genes, and to further select genes among identified candidates, which are systematically associated with a given pathology. These include various methods for differential expression analysis (e.g. differential display, serial analysis of gene expression or SAGE), and positional cloning methods. In the positional cloning approach, the initial steps are quite similar or identical; most often, it is only the final steps that differ (see e.g. Rommens et al., 1989, Science 245, 1059–1065; Duyk et al., 1990, Proc. Natl. Acad. Sci. U.S.A. 87, 8995–8999). The major drawbacks of positional cloning methods generally include: (a) the slow pace of discovery, often requiring several years for success; (b) the high complexity of the techniques involved, requiring highly-trained individuals who must pay painstaking attention to detail to get satisfactory results; (c) the labor-intensive nature of the techniques, often requiring enormous amounts of sequencing; and (d) the extreme expense associated with any slow, complex, labor-intensive effort. Positional cloning can be considered as four discrete steps which are well-known in the art. Each of these steps is briefly described below.

2.2.1. Linkage Mapping

The first step in using positional cloning for disease gene identification consists of a search for genetic linkage between a locus implicated in pathogenesis and a number of genotypic polymorphic markers. This step requires segregation analysis in affected families. Linkage mapping takes advantage of the fact that the closer two genetic loci are to each other, the smaller the chances of an independent recombination event in separating them. Therefore, the aim is to find a specific fragment of genomic DNA bordered by two known markers systematically present in all affected members of a family, but rarely present in the unaffected members. If such a genomic fragment can be identified, the pathogenic locus will be found located between the markers.

Linkage mapping presents difficulties that vary according to the mode of inheritance of a disease. In an ideal linkage map, all bearers of an abnormal gene will be identified. In the case of an autosomal dominant disease, this is only theoretically possible if: (a) all bearers show the diseased phenotype (i.e. penetrance is complete); and (b) disease manifestation is precocious. In the case of autosomal recessive disorders, it is only possible to detect the homozygotes (all affected) and the obligate heterozygotes (the parents). It is therefore essential to have access to families where there are at least two living, homozygous affected siblings when mapping an autosomal recessive disorder.

In a few lucky cases of linkage map construction and analysis, specific chromosomes can be easily ruled out as carrying the diseased gene of interest. In these rare instances, the gene search quickly becomes more focused. For example, DMD is a recessive disorder which is very rare in females. As a result, the search for the DMD gene could safely be limited to the X chromosome. However, in the majority of cases, such a simplified approach is not at all available. A case in point is CF, where it took five years of intensive effort just to identify the chromosome associated with the disease.

2.2.2. Chromosomal Localization

The genomic fragment identified in the preceding step is often very large (i.e. several million bases) and entirely unknown in terms of the number and identity of genes it encodes. Therefore, it is often essential to localize the genomic fragment to a specific chromosome in order to take advantage of other known markers which may not yet be associated with the fragment. Chromosomal localization may be carried out by utilization of polymorphic markers (e.g. microsatellites) identified on genomic DNA or large genomic fragments cloned into yeast artificial chromosomes (YACS) that have been assigned to specific human chromosomes. Chromosomal localization may also be effected by fluorescently labeling a large (e.g. 100 kilobase) identified genomic fragment for hybridization and karyotype analysis (Dauwerse et al., 1992, Hum. Mol. Genet. 1, 593–598).

2.2.3. Further Refinement

Once the identified genomic fragment has been localized to a specific chromosome, the largest possible number of polymorphic markers is used to bracket the smallest possible region (i.e. locus) encoding the gene of interest. This step can yield genomic fragments that are still very large, i.e. one-half to one million bases long. Since the average length of a gene is on the order of seventy thousand bases, such a region is very likely to encode many different genes. Furthermore, this approach does not allow one to distinguish between monogenic and polygenic disorders. If an apparent lack of genetic heterogeneity cannot be clinically determined, then the actual degree of heterogeneity must be assessed by systematic comparison of different families. In this very-frequent case, the results from each family must be analyzed separately to determine whether they are consistent with a "single locus" hypothesis. This is a complex problem since genetic heterogeneity may be clinically undetectable (e.g. pituitary dwarfism, see above). Alternatively, apparent clinical heterogeneity may lead to the erroneous conclusion that different genes are involved when, in fact, different allelic forms of the same gene are involved (e.g. DMD and Becker's myopathy, see above).

2.2.4. From Locus to Gene

Having defined a genetic locus for a disease-associated gene using the above methods, there is much work left to be done before the gene itself is ultimately identified. The identification problem encompasses two major difficulties. First, it is necessary to generate new markers for further map refinement. The new markers must be located as close as possible to, and ultimately in, the gene concerned. Second, it is necessary to demonstrate that the identified gene is actually responsible for the disease. These two tasks require the utilization, in parallel, of a wide variety of methods. Two of the most commonly followed approaches are briefly described below.

Exon trapping involves the cloning of short fragments generated from an entire identified locus into retroviral vectors which have been engineered to reveal the presence of exons (i.e. coding sequences) within a short fragment. Any positive clones (i.e. clones containing an exon) function as new markers and must next be sequenced and mapped back to the locus in order to define the relative position of each. The exon trapping approach is enormously labor-intensive in that it requires massive amounts of DNA sequencing and produces a substantial number of false positives and false negatives. Of course, the exon map generated includes exons from any gene within the locus and is not specific to exons from the disease gene of interest. Accordingly, further work is required.

Complementary DNA (cDNA) subtraction assays utilize cDNA libraries constructed from cells of an affected individual and from cells of a healthy individual. The procedure has two successive phases. In phase one, the cDNA inserts from the healthy individual are immobilized on a membrane and used to trap (subtract) the homologous cDNA inserts present in the affected individual's library. In phase two, the procedure is inverted: i.e. the cDNA inserts from the library of the affected individual are immobilized and used to subtract homologous inserts from the healthy cDNA library. Therefore, these two phases yield cDNA fragments that are entirely unique to the affected or to the healthy individual, respectively. Any fragment homologous (similar but not identical) to a sequence present in the immobilized library remains trapped. Accordingly, this approach often results in a complete loss of the gene of interest.

Clones obtained by the exon trapping or cDNA subtraction approaches are then used for direct hybridization to: (a) yeast artificial chromosome overlapping segments (YAC contigs) covering the locus of interest; (b) mRNA preparations obtained from affected and healthy individuals; and/or (c) enriched genomic libraries obtained from the same affected and healthy individuals. Any positive hybridization signals are then further analyzed by sequencing.

At the last step in positional cloning, i.e. gene identification, one is often confronted with results that cannot precisely pinpoint the relevant gene. In this instance, the only approach remaining is to entirely sequence and analyze the smallest genomic region of the defined locus, which may still range from 300 to 700 kilobases. The problematic nature of positional cloning for disease gene identification is further highlighted below in noting a few of the realities associated with the approach.

Positional cloning projects are so labor intensive that they have been undertaken, in most instances, only by large consortia of international research groups comprising at least three laboratories per consortium. Each laboratory of such a consortium, in turn, is typically composed of five or more researchers devoting essentially all of their time and effort to the project. For example, identification of the CF gene took a total of eight years, finding the gene for polycystic kidney disease type 1 (PKD1) took six years, and finding the ataxia-telangiectasia gene took over five years. Many other examples could be recited, and many positional cloning efforts have yet to identify the target gene. Notably, these are all monogeneic diseases, i.e. only one gene is responsible for the disease and it is the same gene in all cases of the disease.

The difficulties are amplified in the context of polygenic or multifactorial disorders. Here, very little progress has been made in gene identification. For example, after over fifteen years of intensive searching by a considerable number of research teams, the genetic causes of diabetes mellitus (type I and type II) remain largely unknown. The same can be said for chronic renal failure (CRF), multiple sclerosis (MS), atherosclerosis, and many others. This list names only a few of the most prevalent polygenic or multifactorial disorders.

One of the major reasons for this state of affairs is that, in the absence of any information allowing the testing of likely candidate genes, it is necessary to first map the loci associated with the disorder to specific chromosomal regions before having a chance of isolating the genes concerned by positional cloning (see above). Of course, it would be considerably simpler to forego mapping entirely and work from mRNA transcripts of genes expressed in affected tissues. However, this approach has proven virtually impossible using past methods. This is due, at least in part, to the fact that tissues and cells express a great many genes. Furthermore, genes associated with pathologies are often expressed at very low levels. Therefore, the few relevant disease mRNA transcripts may be lost among an enormous number of other transcripts. Still further adding to the identification problem, the disease transcripts may differ widely among affected individuals. These intrinsic shortcomings of past positional and subtraction methodologies are such that very small quantities of mRNA cannot be used.

The VGID$^{SM}$ method for gene identification set forth herein provides a simple solution to this enormous problem. It allows one to identify phenotype-associated genes, in monogenic as well as polygenic contexts, in a matter of weeks rather than years and at greatly reduced expense.

2.3. Mismatch Repair

DNA mismatch repair genes comprise one of several mechanisms by which high fidelity DNA replication is maintained in cells under physiologic conditions. Many investigators over the years have manipulated one or more of these genes to achieve various ends. First described in bacteria, the mismatch repair system comes into play when the product of the MutS gene recognizes and binds to a mispaired base pair (see Cox, E. C., 1997, MutS, Proofreading And Cancer, *Genetics* 146, 443–446). MutS works in concert with the products of the MutH and MutL genes; these three proteins together form the so-called MutHLS mismatch repair system. A recent review has provided a detailed description of this system in eukaryotes (see Kolodner, R., 1996, Biochemistry And Genetics Of Eukaryotic Mismatch Repair, *Genes Dev.* 10, 1433–1442).

Hereditary nonpolyposis colon cancer (HNPCC) arises from mutations in the hMSH2 gene, the human homolog of the bacterial MutS gene, as shown by two laboratories in 1993 (see Fishel, R. et al., 1993, The Human Mutator Gene Homolog MSH2 And Its Association With Hereditary Nonpolyposis Colon Cancer, *Cell* 75, 1027–1038; Leach, F. S. et al., 1993, Mutations Of A MutS Homolog In Hereditary Nonpolyposis Colorectal Cancer, *Cell* 75, 1215–1225). The human MSH2 protein also functions via binding to DNA mismatches (Fishel, R. et al., 1994, Binding Of Mismatched Microsatellite DNA Sequences By The Human MSH2 Protein, *Science* 266, 1403–1405; Fishel, R. et al., 1994, Purified Human MSH2 Protein Binds To DNA Containing Mismatched Nucleotides, *Cancer Res.* 54, 5539–5542). Another human homolog of bacterial MutS has recently been linked to cancer susceptibility (Edelman, W. et al., Nov. 14, 1997, Mutation In The Mismatch Repair Gene Msh6 Causes Cancer Susceptibility, *Cell* 91, 467–477).

Traditionally, manipulation of the mismatch repair system has been employed in a variety of ways. For example, a method for in vitro recombination of mismatches has been described which takes advantage of MutS-deficient *E. coli* (Resnick, M. A. and Radman, M., Aug. 2, 1994, System For Isolating And Producing New Genes, Gene Products And DNA Sequences, U.S. Pat. No. 5,334,522). Others have described using the MutS protein to detect DNA mismatches in vitro with antibodies (Wagner, R. E., Jr. and Radman, M., Apr. 2, 1997, Method For Detection Of Mutations, European Patent EP 0 596 028 B1). Still others have used the inability of the system to repair loops of five nucleotides or greater in vivo to design a system capable of detecting a single mismatch in a DNA fragment as large as 10 kilobases (see Faham, M. and Cox, D. R., 1997, A Novel in vivo Method To Detect DNA Sequence Variation, *Genome Research* 5, 474–482).

3. SUMMARY OF THE INVENTION

This invention provides a method for identifying a gene or allele, or several genes or alleles, underlying a phenotype-of-interest. In this regard, genes or alleles are identified as having a specified function, or as causing or contributing to the cause or pathogenesis of a specified disease, or as associated with a specific phenotype, by virtue of their selection by the method.

This invention is based, at least in part, on the recognition that comparison of a population of nucleic acid molecules with one or more other populations of nucleic acid molecules, so as to isolate genes underlying specific phenotypic traits, is greatly facilitated by first taking steps to insure internal homogenization of one or more of the populations to be compared before performing the external comparison of two or more populations. In this regard, internal homogenization is effected by a first round of hybridization and sorting of matched from mismatched DNA duplexes. Similarly, external comparison is effected by a second round of hybridization and sorting of matched from mismatched DNA duplexes, as described in detail hereinbelow.

This invention provides a method for identifying one or more genes underlying a defined phenotype comprising the following steps in the order stated: (a) removing mismatched duplex nucleic acid molecules formed from hybridization within each of two source populations of nucleic acids; and (b) retaining mismatched duplex nucleic acid molecules formed from hybridization between the two source populations, the retained molecules in step (b) comprising the one or more genes underlying the defined phenotype.

Further, this invention provides a method for identifying one or more genes underlying a defined phenotype comprising the following steps in the order stated: (a) removing mismatched duplex nucleic acid molecules formed from hybridization within a first source population of nucleic acids; and (b) retaining mismatched duplex nucleic acid molecules formed from hybridization between the first source population and a second source population of nucleic acids, the retained molecules in step (b) comprising the one or more genes underlying the defined phenotype.

Nucleic acid sample populations may be derived from many different sources. In one embodiment, the first and second source populations each are nucleic acid populations derived from at least two individuals having consanguinity. In another embodiment, the first and second source populations each are nucleic acid populations derived from more than two individuals having consanguinity. In one embodiment, the first and second source populations each are nucleic acid populations derived from two to six individuals having consanguinity. In another embodiment, the first and second source populations each are nucleic acid populations derived from three individuals having consanguinity. In still another embodiment, each source population is a cell line.

Further, nucleic acid sample populations may be manipulated in various ways so as to facilitate gene identification. In one embodiment, the source populations are normalized cDNA libraries to facilitate identification of rare transcripts. In another embodiment, the source populations are linearized cDNA libraries to facilitate hybridization. In still another embodiment, the source populations are normalized and linearized.

Still further, nucleic acid sample populations may be manipulated in various ways so as to facilitate removal of undesired cDNAs. In one embodiment, the two source populations are of DNA, the DNA of a source population is labeled, and the hybridization in step (b) is carried out using an excess of labeled DNA. In another embodiment, the excess of labeled DNA is a three-fold excess.

Genes underlying virtually any defined phenotype may be identified using the method of the invention. In a preferred embodiment, the defined phenotype is selected from the group consisting of a plant resistance phenotype, a microorganism resistance phenotype, cancer, osteoporosis, obesity, type II diabetes, and a prion-related disease. Additional examples of preferred defined phenotypes follow immediately below.

Defined plant phenotypes include but are not limited to resistance to herbicides, resistance to insect predators, resistance to fungal infections, increased yields, resistance to frost, resistance to dehydration, enhanced stem strength, and many others.

Defined microorganism phenotypes include but are not limited to susceptibility or resistance to antibiotics, detoxification of liquids, soils, solids, and/or gases contaminated by pollutants or toxic compounds (e.g. dioxin, nitrous oxides, carbon monoxide, sulfur dioxide, free radicals, and so on).

Defined animal and/or veterinary phenotypes include but are not limited to resistance to neurological disorders such as prion-related diseases, infectious disorders (e.g. porcine plague), foot-and-mouth disease, and many others.

Defined human phenotypes include but are not limited to susceptibility to cancer, autoimmune diseases, neurological disorders, metabolic disorders (e.g. diabetes, obesity), systemic diseases (e.g. osteoporosis), and many others.

This invention provides a method for identifying one or more genes underlying a defined phenotype displayed by a cell or individual from which a first cDNA library is derived, but not displayed by a cell or individual from which a second cDNA library is derived. The method comprises the steps of (a) hybridizing insert DNA from the first cDNA library with itself, (b) hybridizing insert DNA from the second cDNA library with itself, (c) contacting the DNA hybridized in step (a) with a first immobilized mismatch binding protein, (d) contacting the DNA hybridized in step (b) with a second immobilized mismatch binding protein, (e) separating unbound DNA from bound DNA contacted in step (c), (f) separating unbound DNA from bound DNA contacted in step (d), (g) labeling unbound DNA separated in step (f) with a label capable of binding a partner molecule or agent immobilized on a substrate, (h) hybridizing labeled DNA with unbound DNA separated in step (e), (i) contacting DNA hybridized in step (h) with a third immobilized mismatch binding protein, (j) separating unbound DNA from bound DNA contacted in step (i), (k) contacting unbound DNA separated in step (j) with the partner molecule or agent immobilized on the substrate capable of binding the label, and (l) separating unbound DNA from bound DNA contacted in step (k), which unbound DNA separated in step (l) encodes one or more identified genes underlying the defined phenotype.

Further, this invention provides a method for identifying one or more genes underlying a defined phenotype from organisms having consanguinity. The method comprises the steps of (a) hybridizing insert DNA from a first collection of cDNA libraries derived from organisms having the defined phenotype with itself, (b) contacting DNA hybridized in step (a) with a first immobilized mismatch binding protein, (c) separating unbound DNA from bound DNA contacted in step (b), (d) labeling unbound DNA separated in step (c) with a label capable of binding a partner molecule or agent immobilized on a substrate, (e) hybridizing DNA labeled in step (d) with insert DNA from a second collection of cDNA libraries derived from organisms not having the defined phenotype, (f) contacting DNA hybridized in step (e) with a second immobilized mismatch binding protein, (g) separating unbound DNA from bound DNA contacted in step (f), (h) contacting unbound DNA separated in step (g) with the partner molecule or agent immobilized on the substrate capable of binding the label, and (i) separating unbound DNA from bound DNA contacted in step (h), which unbound DNA separated in step (i) encodes identified genes underlying the defined phenotype. This paragraph sets forth a preferred embodiment in which the DNA labeled in step (d) corresponds to undesired material labeled for removal.

Still further, this invention provides a method for identifying one or more alleles underlying a defined phenotype displayed by a cell or individual from which a first cDNA library is derived, but not displayed by a cell or individual from which a second cDNA library is derived. The method comprises the steps of (a) hybridizing insert DNA from the first cDNA library with itself, (b) hybridizing insert DNA from the second cDNA library with itself, (c) contacting the DNA hybridized in step (a) with a first immobilized mismatch binding protein, (d) contacting the DNA hybridized in step (b) with a second immobilized mismatch binding protein, (e) separating unbound DNA from bound DNA contacted in step (c), (f) separating unbound DNA from bound DNA contacted in step (d), (g) labeling unbound DNA separated in step (f) with a label capable of binding a partner molecule or agent immobilized on a substrate, (h) hybridizing DNA labeled in step (g) with unbound DNA separated in step (e), (i) contacting DNA hybridized in step (h) with a third immobilized mismatch binding protein, (j) separating unbound DNA from bound DNA contacted in step (i), (k) releasing bound DNA separated in step (j) from the third immobilized mismatch binding protein, (l) contacting DNA released in step (k) with the partner molecule or agent immobilized on the substrate capable of binding the label, (m) denaturing DNA contacted in step (l), and (n) separating unbound DNA from bound DNA denatured in step (m), which unbound DNA separated in step (n) encodes one or more identified alleles underlying the defined phenotype.

Yet still further, this invention provides a method for identifying one or more alleles underlying a defined phenotype from organisms having consanguinity. The method comprises the steps of (a) hybridizing insert DNA from a first collection of cDNA libraries derived from organisms having the defined phenotype with itself, (b) contacting DNA hybridized in step (a) with a first immobilized mismatch binding protein, (c) separating unbound DNA from bound DNA contacted in step (b), (d) labeling unbound DNA separated in step (c) with a label capable of binding a partner molecule or agent immobilized on a substrate, (e) hybridizing DNA labeled in step (d) with insert DNA from a second collection of cDNA libraries derived from organisms not having the defined phenotype, (f) contacting DNA hybridized in step (e) with a second immobilized mismatch binding protein, (g) separating unbound DNA from bound DNA contacted in step (f), (h) releasing bound DNA separated in step (g) from the second immobilized mismatch binding protein, (i) contacting DNA released in step (h) with the partner molecule or agent immobilized on the substrate capable of binding the label, (j) denaturing DNA contacted in step (i), and (k) separating bound DNA from unbound DNA denatured in step (j), which bound DNA separated in step (k) encodes one or more identified alleles underlying the defined phenotype.

The cDNA library collections will vary according to the specific attributes of the sample source. In one embodiment, the first and second cDNA library collections each are nucleic acid populations derived from at least two individuals having consanguinity. In another embodiment, the first and second cDNA library collections each are nucleic acid populations derived from more than two individuals having consanguinity. In one embodiment, the first and second cDNA library collections each are nucleic acid populations derived from two to six individuals having consanguinity. In another embodiment, the first and second cDNA library collections each are nucleic acid populations derived from three individuals having consanguinity.

A nucleic acid sample population may be left unlabeled or labeled with a unique label in various ways. In one embodiment, labeling is effected by polymerase chain reaction using a 5'-biotinylated primer. In another embodiment, labeling is effected by polymerase chain reaction using a 5'-peptide-labeled primer. In a preferred embodiment, labeling using a 5'-biotinylated primer is performed when using one unlabeled sample population and one labeled sample population. In another preferred embodiment, labeling using a 5'-peptide-labeled primer is performed when multiplexing, i.e. when using three or more nucleic acid sample populations.

A labeled nucleic acid sample population may be sorted in various ways. In one embodiment, the substrate for binding the biotin label is streptavidin. In another embodiment, the substrate for binding the peptide label is an antibody. In still another embodiment, the antibody is an anti-peptide antibody. In yet still another embodiment, the anti-peptide antibody is monoclonal.

A variety of wild-type and recombinant, engineered mismatch binding proteins may be used to effect sorting (i.e. binding and release) of DNA duplexes containing mismatches. In one embodiment, the mismatch binding protein is *E. coli* MutS. In another embodiment, the mismatch binding protein is hMSH2. In still another embodiment, the mismatch binding protein is an hMSH2-hMSH6 protein complex.

This invention provides a method for identifying one or more genes underlying a defined phenotype displayed by a cell or individual from which a first cDNA library is derived, but not displayed by a cell or individual from which a second cDNA library is derived. The method comprises the steps of (a) amplifying insert DNA from the first cDNA library by polymerase chain reaction, (b) amplifying insert DNA from the second cDNA library by polymerase chain reaction, (c) hybridizing DNA amplified in step (a) with itself, (d) hybridizing DNA amplified in step (b) with itself, (e) contacting DNA hybridized in step (c) with a first immobilized MutS, (f) contacting DNA hybridized in step (d) with a second immobilized MutS, (g) separating unbound DNA from bound DNA contacted in step (e), (h) separating unbound DNA from bound DNA contacted in step (f), (i) amplifying unbound DNA separated in step (g) by polymerase chain reaction using unlabeled primers, (j) amplifying and labeling unbound DNA separated in step (h) by polymerase chain reaction using 5'-biotinylated primers, (k) hybridizing DNA amplified and labeled in step (j) with DNA amplified in step (i), (l) contacting DNA hybridized in step (k) with a third immobilized MutS, (m) separating unbound DNA from bound DNA contacted in step (l), (n) contacting unbound DNA separated in step (m) with immobilized streptavidin, and (o) separating unbound DNA from bound DNA contacted in step (n), which unbound DNA separated in step (o) encodes one or more identified genes underlying the defined phenotype.

Further, this invention provides a method for identifying one or more genes underlying a disease phenotype from healthy and affected individuals having consanguinity. The method comprises the steps of (a) amplifying insert DNA from a first collection of cDNA libraries derived from affected individuals by polymerase chain reaction, (b) hybridizing DNA amplified in step (a) with itself, (c) contacting DNA hybridized in step (b) with a first immobilized MutS, (d) separating unbound DNA from bound DNA contacted in step (c), (e) amplifying and labeling unbound DNA separated in step (d) by polymerase chain reaction using 5'-biotinylated primers, (f) amplifying insert DNA from a second collection of cDNA libraries derived from healthy individuals by polymerase chain reaction, (g) hybridizing DNA amplified and labeled in step (e) with DNA amplified in step (f), (h) contacting DNA hybridized in step (g) with a second immobilized MutS, (i) separating unbound DNA from bound DNA contacted in step (h), (j) contacting unbound DNA separated in step (i) with immobilized streptavidin, and (k) separating unbound DNA from bound DNA contacted in step (j), which unbound DNA separated in step (k) encodes one or more identified genes underlying the disease phenotype.

Still further, this invention provides a method for identifying one or more alleles underlying a defined phenotype displayed by a cell or individual from which a first cDNA library is derived, but not displayed by a cell or individual from which a second cDNA library is derived. The method comprises the steps of (a) amplifying insert DNA from the first cDNA library by polymerase chain reaction, (b) amplifying insert DNA from the second cDNA library by polymerase chain reaction, (c) hybridizing DNA amplified in step (a) with itself, (d) hybridizing DNA amplified in step (b) with itself, (e) contacting DNA hybridized in step (c) with a first immobilized MutS, (f) contacting DNA hybridized in step (d) with a second immobilized MutS, (g) separating unbound DNA from bound DNA contacted in step (e), (h) separating unbound DNA from bound DNA contacted in step (f), (i) amplifying unbound DNA separated in step (g) by polymerase chain reaction using unlabeled primers, (j) amplifying and labeling unbound DNA separated in step (h) by polymerase chain reaction using 5'-biotinylated primers, (k) hybridizing DNA amplified and labeled in step (j) with DNA amplified in step (i), (l) contacting DNA hybridized in step (k) with a third immobilized MutS, (m) separating unbound DNA from bound DNA contacted in step (l), (n) releasing bound DNA separated in step (m) from the third immobilized MutS, (o) contacting DNA released in step (n) with immobilized streptavidin, (p) denaturing DNA contacted in step (o), and (q) separating unbound DNA from bound DNA denatured in step (p), which unbound DNA separated in step (q) encodes one or more identified alleles underlying the defined phenotype. In one embodiment, releasing bound DNA from the third immobilized MutS in step (n) is carried out using ATP or proteinase K.

Yet still further, this invention provides a method for identifying one or more affected alleles underlying a disease phenotype from healthy and affected individuals having consanguinity. The method comprises the steps of (a) amplifying insert DNA from a first collection of cDNA libraries derived from affected individuals by polymerase chain reaction, (b) hybridizing DNA amplified in step (a) with itself, (c) contacting DNA hybridized in step (b) with a first immobilized MutS, (d) separating unbound DNA from bound DNA contacted in step (c), (e) amplifying and labeling unbound DNA separated in step (d) by polymerase chain reaction using 5'-biotinylated primers, (f) amplifying insert DNA from a second collection of cDNA libraries derived from healthy individuals by polymerase chain reaction, (g) hybridizing DNA amplified and labeled in step (e) with DNA amplified in step (f), (h) contacting DNA hybridized in step (g) with a second immobilized MutS, (i) separating unbound DNA from bound DNA contacted in step (h), (j) releasing bound DNA separated in step (i) from the second immobilized MutS, (k) contacting DNA released in step (j) with immobilized streptavidin, (l) denaturing DNA contacted in step (k), and (m) separating bound DNA from unbound DNA denatured in step (l), which bound DNA separated in step (m) encodes one or more identified affected alleles underlying the disease phenotype. In one embodiment, releasing bound DNA from the second immobilized MutS in step (j) is carried out using ATP or proteinase K.

Yet still further, this invention provides a method for identifying one or more genes underlying a defined phenotype displayed by a cell or individual from which a first cDNA library is derived, but not displayed by a cell or individual from which a plurality of additional cDNA libraries is derived. The method comprises the steps of (a) hybridizing insert DNA from each cDNA library with itself, (b) contacting each separate population of DNA hybridized in step (a) individually with an immobilized mismatch binding protein, (c) separating unbound DNA from bound DNA contacted individually in step (b), (d) labeling each separate population of unbound DNA separated in step (c) with a different label capable of binding a partner molecule immobilized on a substrate, (e) hybridizing DNA separately labeled in step (d), (f) contacting DNA hybridized in step (e) with an immobilized mismatch binding protein, and (g) separating unbound DNA from bound DNA contacted in step (f).

Still further, this invention provides a method for identifying one or more genes underlying a defined phenotype displayed by a cell or individual from which a first cDNA library is derived, but not displayed by a cell or individual from which a plurality of additional cDNA libraries is derived. The method comprises the steps of (a) amplifying insert DNA from a second collection of cDNA libraries by polymerase chain reaction, (b) hybridizing each separate population of DNA amplified in step (a) with itself, (c) contacting each separate population of DNA hybridized in step (b) individually with immobilized MutS, (d) separating unbound DNA from bound DNA contacted in step (c), (e) labeling each separate population of unbound DNA separated in step (d) by polymerase chain reaction using a distinct 5'-peptide-labeled primer capable of binding a partner molecule immobilized on a substrate, (f) hybridizing DNA labeled in step (e), (g) contacting DNA hybridized in step (f) with immobilized MutS, and (h) separating unbound DNA from bound DNA contacted in step (g).

Further, this invention provides a method for identifying one or more alleles underlying a defined phenotype displayed by a cell or individual from which a first cDNA library is derived, but not displayed by a cell or individual from which a plurality of additional cDNA libraries is derived. The method comprises the steps of (a) hybridizing insert DNA from each cDNA library with itself, (b) contacting each separate population of DNA hybridized in step (a) individually with an immobilized mismatch binding protein, (c) separating unbound DNA from bound DNA contacted in step (b), (d) labeling each separate population of unbound DNA separated in step (c) with a distinct label capable of binding a partner molecule immobilized on a substrate, (e) hybridizing DNA labeled in step (d), (f) contacting DNA hybridized in step (e) with an immobilized mismatch binding protein, and (g) separating unbound DNA from bound DNA contacted in step (f).

Still further, this invention provides a method for identifying one or more alleles underlying a defined phenotype displayed by a cell or individual from which a first cDNA library is derived, but not displayed by a cell or individual from which a plurality of additional cDNA libraries is derived. The method comprises the steps of (a) amplifying insert DNA from each cDNA library by polymerase chain reaction, (b) hybridizing DNA amplified from each library in step (a) with itself, (c) contacting DNA from each library hybridized in step (b) individually with an immobilized mismatch binding protein, (d) separating unbound DNA from bound DNA contacted in step (c), (e) amplifying and labeling each separate population of unbound DNA separated in step (d) by polymerase chain reaction using a distinct 5'-peptide-labeled primer, (f) hybridizing DNA amplified and labeled in step (e), (g) contacting DNA hybridized in step (f) with an immobilized mismatch binding protein, (h) separating unbound DNA from bound DNA contacted in step (g), (i) releasing bound DNA separated in step (h), and (j) separating DNA released in step (i) into single strands.

Still further, this invention provides a method for identifying one or more alleles underlying a defined phenotype comprising the following steps in the order stated: (a) removing mismatched duplex nucleic acid molecules formed from hybridization within each of a plurality of source populations of nucleic acids; (b) retaining mismatched duplex nucleic acid molecules formed from hybridization among the plurality of source populations; (c) separating mismatched strands retained in step (b), which separated strands comprise one or more alleles underlying the defined phenotype.

This invention provides a method for identifying one or more genes underlying a defined phenotype. The method comprises the steps of (a) removing mismatched duplex nucleic acid molecules formed from hybridization within each of a plurality of source populations of nucleic acids, and (b) retaining mismatched duplex nucleic acid molecules formed from hybridization among the plurality of source populations, the retained molecules in step (b) comprising the one or more genes underlying the defined phenotype. In one embodiment, the plurality of source populations comprises at least one normalized cDNA library. In another embodiment, the plurality of source populations comprises at least one linearized cDNA library. In yet another embodiment, the plurality of source populations consists of DNA, the DNA of each of the source populations being labeled with a different label, and the hybridization in step (b) is carried out using an excess of labeled DNA from one or more source populations. In one embodiment, the excess of labeled DNA is a three-fold excess. Yet in another embodiment, each of the source populations is derived from a cell line.

This invention also provides a method for identifying one or more genes underlying a defined phenotype displayed by a cell or individual from which a first cDNA library is derived, but not displayed by a cell or individual from which a plurality of additional cDNA libraries is derived. The method comprises the steps of (a) hybridizing insert DNA from the first cDNA library with itself, (b) hybridizing insert DNA from each library of the plurality of additional cDNA libraries with itself, (c) contacting the DNA hybridized in step (a) with an immobilized mismatch binding protein, (d) contacting each separate population of DNAs hybridized in step (b) individually with an immobilized mismatch binding protein, (e) separating unbound DNA from bound DNA contacted in step (c), (f) separating unbound DNA from bound DNA contacted individually in step (d), (g) labeling each separate population of the unbound DNA separated in step (f) with a distinguishable label capable of binding a partner molecule immobilized on a substrate, (h) hybridizing DNA separately labeled in step (g) with unbound DNA separated in step (e), (i) contacting DNA hybridized in step (h) with an immobilized mismatch binding protein, (j) separating unbound DNA from bound DNA contacted in step (i), (k) contacting unbound DNA separated in step (j) with the partner molecule of each different label, and (l) separating unbound DNA from bound DNA contacted in step (k), which unbound DNA separated in step (l) encodes one or more identified genes underlying the defined phenotype. In one embodiment, one or more of the cDNA libraries is normalized. In another embodiment, one or more of the cDNA libraries is linearized. In yet another embodiment, labeling is carried out by polymerase chain reaction using a 5'-peptide labeled primer. In yet another embodiment, at least one partner molecule immobilized is an antibody. In still another embodiment, the antibody is an anti-peptide antibody. In yet another embodiment, the hybridization in step (h) is carried out using an excess of labeled DNA. In yet another embodiment, the excess of labeled DNA is a three-fold excess. In yet another embodiment, an immobilized mismatch binding protein is MutS. In one embodiment, the defined phenotype is selected from the group consisting of a plant phenotype, a microorganism phenotype, and a pathologic phenotype. In another embodiment, the defined phenotype is a pathologic phenotype that is selected from the group consisting of cancer, osteoporosis, obesity, type II diabetes, and a prion-related disease.

This invention further provides a method for identifying one or more genes underlying a defined phenotype displayed by a cell or individual from which a first cDNA library is derived, but not displayed by a cell or individual from which a plurality of additional cDNA libraries is derived. The method comprises the steps of (a) amplifying insert DNA from the first cDNA library by polymerase chain reaction, (b) amplifying insert DNA from each of the plurality of additional cDNA libraries by polymerase chain reaction, (c) hybridizing DNA amplified in step (a) with itself, (d) hybridizing each separate population of DNA amplified in step (b) with itself, (e) contacting DNA hybridized in step (c) with immobilized MutS, (f) contacting each separate population of DNA hybridized in step (d) individually with immobilized MutS, (g) separating unbound DNA from bound DNA contacted in step (e), (h) separating unbound DNA from bound DNA contacted in step (f), (i) labeling unbound DNA separated in step (g) by polymerase chain reaction using unlabeled primers, (j) labeling each separate population of unbound DNA separated in step (h) by polymerase chain reaction using a primer having a distinguishable 5'-peptide-label capable of binding a partner molecule immobilized on a substrate, (k) hybridizing DNA labeled in step (i) with DNA labeled in step (j), (l) contacting DNA hybridized in step (k) with immobilized MutS, (m) separating unbound DNA from bound DNA contacted in step (l), (n) contacting unbound DNA separated in step (m) with one or more partner molecules capable of binding the distinguishable 5'-peptide-labeled primers, and (o) separating unbound DNA from bound DNA contacted in step (n), which unbound DNA separated in step (o) encodes one or more identified genes underlying the defined phenotype.

This invention provides a method for identifying one or more alleles underlying a defined phenotype displayed by a cell or individual from which a first cDNA library is derived, but not displayed by a cell or individual from which a plurality of additional cDNA libraries is derived. The method comprises the steps of (a) hybridizing insert DNA from the first cDNA library with itself, (b) hybridizing insert DNA from each of the plurality of additional cDNA libraries with itself, (c) contacting DNA hybridized in step (a) with an immobilized mismatch binding protein, (d) contacting each separate population of DNA hybridized in step (b) individually with an immobilized mismatch binding protein, (e) separating unbound DNA from bound DNA contacted in step (c), (f) separating unbound DNA from bound DNA contacted in step (d), (g) labeling each separate population of unbound DNA separated in step (f) with a distinguishable label capable of binding a partner molecule immobilized on a substrate, (h) hybridizing DNA labeled in step (g) with unbound DNA separated in step (e), (i) contacting DNA hybridized in step (h) with an immobilized mismatch binding protein, (j) separating unbound DNA from bound DNA contacted in step (i), (k) releasing bound DNA separated in step (j) from the immobilized mismatch binding protein, (l) contacting DNA released in step (k) with one or more partner molecules capable of binding the distinct labels, (m) denaturing DNA contacted in step (l), and (n) separating unbound DNA from bound DNA denatured in step (m), which unbound DNA separated in step (n) encodes one or more identified alleles underlying the defined phenotype. In one embodiment, at least one cDNA library is normalized. In another embodiment, at least one cDNA library is linearized. In one embodiment, labeling is carried out by polymerase chain reaction using 5'-peptide labeled primers. In another embodiment, at least one immobilized partner molecule is an antibody. In another embodiment, the antibody is an anti-peptide antibody. In another embodiment, the hybridization in step (h) is carried out using an excess of labeled DNA. In another embodiment, the excess of labeled DNA is a three-fold excess. In another embodiment, at least one of the immobilized mismatch binding proteins is MutS.

This invention provides a method for identifying one or more alleles underlying a defined phenotype displayed by a cell or individual from which a first cDNA library is derived, but not displayed by a cell or individual from which a plurality of additional cDNA libraries is derived. The method comprises the steps of (a) amplifying insert DNA from the first cDNA library by polymerase chain reaction, (b) amplifying insert DNA from each of the plurality of additional cDNA libraries by polymerase chain reaction, (c) hybridizing DNA amplified in step (a) with itself, (d) hybridizing DNA amplified from each library in step (b) with itself, (e) contacting DNA hybridized in step (c) with immobilized MutS, (f) contacting each population of DNA hybridized in step (d) individually with immobilized MutS, (g) separating unbound DNA from bound DNA contacted in step (e), (h) separating unbound DNA from bound DNA contacted in step (f), (i) amplifying unbound DNA separated in step (g) by polymerase chain reaction using unlabeled primers, (j) amplifying and labeling each population of unbound DNA separated in step (h) by polymerase chain reaction using a distinguishable 5'-peptide-labeled primer, (k) hybridizing DNA amplified and labeled in step (j) with DNA amplified in step (i), (l) contacting DNA hybridized in step (k) with immobilized MutS, (m) separating unbound DNA from bound DNA contacted in step (l), (n) releasing bound DNA separated in step (m) from immobilized MutS, (o) contacting DNA released in step (n) with one or more immobilized antibodies specific for each distinguishable 5'-peptide-labeled primer, (p) denaturing DNA contacted in step (o), and (q) separating unbound DNA from bound DNA denatured in step (p), which unbound DNA separated in step (q) encodes one or more identified alleles underlying the defined phenotype. In one embodiment, releasing bound DNA from immobilized MutS in step (n) is carried out using ATP or proteinase K. In another embodiment, the method further comprises a step of using the one or more genes or alleles identified to carry out a prognosis or a diagnosis. In one embodiment, the one or more genes or alleles identified, or an encoded protein thereof, is a target for drug intervention. In another embodiment, the plurality of source populations is in the range of three to twelve source populations. In yet another embodiment, the plurality of source populations is in the range of three to six source populations. In another embodiment, the plurality of source populations consists of four source populations.

This invention provides a method for identifying one or more genes underlying a defined phenotype displayed by a cell or individual from which a first cDNA library is derived, but not displayed by a cell or individual from which a plurality of additional cDNA libraries is derived. The method comprises the steps of (a) hybridizing insert DNA from each cDNA library with itself, (b) contacting each separate population of DNA hybridized in step (a) individually with an immobilized mismatch binding protein, (c) separating unbound DNA from bound DNA contacted individually in step (b), (d) labeling each separate population of unbound DNA separated in step (c) with a distinguishable label capable of binding a partner molecule immobilized on a substrate, (e) hybridizing DNA separately labeled in step (d), (f) contacting DNA hybridized in step (e) with an immobilized mismatch binding protein, and (g) separating unbound DNA from bound DNA contacted in step (f).

This invention provides a method for identifying one or more genes underlying a defined phenotype displayed by a cell or individual from which a first cDNA library is derived, but not displayed by a cell or individual from which a plurality of additional cDNA libraries is derived. The method comprises the steps of (a) amplifying insert DNA from each cDNA library by polymerase chain reaction, (b) hybridizing each separate population of DNA amplified in step (a) with itself, (c) contacting each separate population of DNA hybridized in step (b) individually with immobilized MutS, (d) separating unbound DNA from bound DNA contacted in step (c), (e) labeling each separate population of unbound DNA separated in step (d) by polymerase chain reaction using a primer having a distinguishable 5'-peptide-label capable of binding a partner molecule immobilized on a substrate, (f) hybridizing DNA labeled in step (e), (g) contacting DNA hybridized in step (f) with immobilized MutS, and (h) separating unbound DNA from bound DNA contacted in step (g).

This invention provides a method for identifying one or more alleles underlying a defined phenotype displayed by a cell or individual from which a first cDNA library is derived, but not displayed by a cell or individual from which a plurality of additional cDNA libraries is derived. The method comprises the steps of (a) hybridizing insert DNA from each cDNA library with itself, (b) contacting each separate population of DNA hybridized in step (a) individually with an immobilized mismatch binding protein, (c) separating unbound DNA from bound DNA contacted in step (b), (d) labeling each separate population of unbound DNA separated in step (c) with a distinguishable label capable of binding a partner molecule immobilized on a substrate, (e) hybridizing DNA labeled in step (d), (f) contacting DNA hybridized in step (e) with an immobilized mismatch binding protein, and (g) separating unbound DNA from bound DNA contacted in step (f).

This invention provides a method for identifying one or more alleles underlying a defined phenotype displayed by a cell or individual from which a first cDNA library is derived, but not displayed by a cell or individual from which a plurality of additional cDNA libraries is derived. The method comprises the steps of (a) amplifying insert DNA from each cDNA library by polymerase chain reaction, (b) hybridizing DNA amplified from each library in step (a) with itself, (c) contacting DNA from each library hybridized in step (b) individually with an immobilized mismatch binding protein, (d) separating unbound DNA from bound DNA contacted in step (c), (e) amplifying and labeling each separate population of unbound DNA separated in step (d) by polymerase chain reaction using a distinct 5'-peptide-labeled primer, (f) hybridizing DNA amplified and labeled in step (e), (g) contacting DNA hybridized in step (f) with an immobilized mismatch binding protein, (h) separating unbound DNA from bound DNA contacted in step (g), (i) releasing bound DNA separated in step (h), and (j) separating DNA released in step (i) into single strands.

This invention provides a method for identifying one or more alleles underlying a defined phenotype. The method comprises the steps of (a) removing mismatched duplex nucleic acid molecules formed from hybridization within each of a plurality of source populations of nucleic acids, (b) retaining mismatched duplex nucleic acid molecules formed from hybridization among the plurality of source populations, and (c) separating mismatched strands retained in step (b), which separated strands comprise one or more alleles underlying the defined phenotype.

4. BRIEF DESCRIPTION OF THE DRAWINGS

Figure 4:
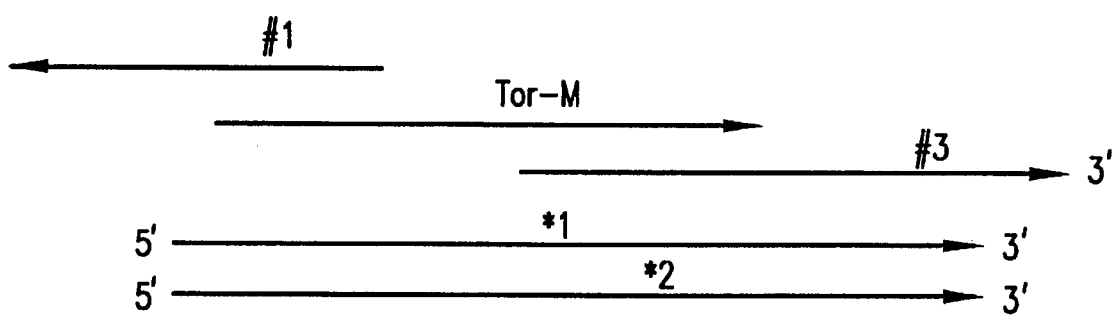

FIG. 4 is a schematic map of five hDinP clones isolated using the VGID[SM] method and cell line samples as input phenotypes. The VGID[SM] approach employed is that illustrated in FIG. 1. A lymphoblast cell line was chosen as cell line # 1 because it expresses a specific alteration in a DNA repair pathway (i.e. "with phenotype" in FIG. 1); a hepatocyte cell line was chosen as cell line # 2 (i.e. "without phenotype" in FIG. 1).

FIGS. 5A–B shows BLASTX search results and computer analysis for the hDinP clone listed in SEQ ID NO:1 (#1).

FIG. 6 shows BLASTX search results and computer analysis for the hDinP clone listed in SEQ ID NO:2 (Tor-M).

FIGS. 7A–B shows BLASTX search results and computer analysis for the hDinP clone listed in SEQ ID NO:3 (#3).

FIGS. 8A–B shows BLASTX search results and computer analysis for the hDinP clone listed in SEQ ID NO:4 (*1).

FIGS. 9A–B shows BLASTX search results and computer analysis for the hDinP clone listed in SEQ ID NO:5 (*2).

5. DETAILED DESCRIPTION OF THE INVENTION

The present invention provides a method, referred to generally as the ValiGene[SM] Gene Identification method, or the VGID[SM] method, for identification of a gene or multiple genes linked to a user-specified phenotype. In this regard, genes linked to a phenotype include genes which cause the phenotype-of-interest, genes which merely contribute to a phenotype which is partly due to genetic factors and partly due to environmental factors, as well as structurally altered genes arising as an effect of a phenotype. The methodology comprising VGID[SM] can be used to perform a function-based analysis of the protein-coding genome of any organism irrespective of biological kingdom. Further, the VGID[SM] method can simultaneously identify multiple alleles of the gene of interest which are associated with multiple phenotypes, including disease phenotypes. Accordingly, phenotype-specific diagnostic tools are provided by genes identified using the VGID[SM] method. In particular, such diagnostic tools may be used as an indication of the presence of the phenotype-of-interest. Further, phenotype-specific prognostic tools are provided by genes identified using the VGID[SM] method; such prognostic tools may be used to indicate or predict a disease course and/or outcome for various disease phenotypes.

The VGID[SM] methodology is based on a constant underlying principle, i.e. the ability to specifically trap and subsequently release mismatched artificial cDNA hybrids formed by annealing interactions between cDNA's originating from phenotypically-distinct sources. Thus, the VGID[SM] methodology is a powerful molecular comparison tool which does not require global sequence information. Instead, a comparison among phenotypic groups is accomplished using cDNA annealing interactions and subsequent sorting of matched from mismatched hybrids.

The details of the VGID[SM] method vary depending upon the precise "comparison" to be made. This is due to the fact that mRNA transcripts derived from different sources will vary in their "complexity" (i.e. genetic heterogeneity) and therefore should undergo slightly different processing approaches, as described in detail below. In one embodiment, the VGID[SM] method is used to isolate transcripts that are identical among phenotypically-distinct groups. In another embodiment, the VGID[SM] method is used to isolate transcripts that are different among such groups. The VGID[SM] method is broadly applicable for identifying the genes underlying specific functions. Common input phenotypes for use with the VGID[SM] method are healthy (normal) and affected (disease) phenotypes. Other common input phenotypes are susceptible and resistant phenotypes (e.g. viruses susceptible and resistant to antiviral agents, microbes susceptible and resistant to antibiotics, plants susceptible and resistant to herbicides, insects susceptible and resistant to insecticides). In this regard, one skilled in the art will recognize that the VGID[SM] method may be applied virtually anywhere two or more input phenotypes are identified, regardless of biological kingdom. Guidelines for input phenotype selection are provided in Section 5.4 hereinbelow.

The VGID[SM] method utilizes nucleic acids obtained or derived from at least two source groups as starting material. In a preferred embodiment, the nucleic acid is cDNA made from messenger RNA (mRNA), preferably total poly A RNA from the source groups. Small quantities of mRNA are sufficient for using the VGID[SM] method. This flexibility in input amount permits a meaningful genetic analysis of rare disease tissue samples, for example. The lower limit amount of source nucleic acid required is the minimal amount sufficient for construction of a cDNA library (i.e. about 1 ng to 1 µg per source with most cDNA library construction techniques).

At its most basic level, the VGID[SM] method may be thought of as an expressed gene subtraction technique. The VGID[SM] method is based upon two rounds of highly efficient mismatch binding protein chromatography for trapping (e.g. by binding to immobilized MutS) of: (a) internally heterologous nucleic acids (round one; see upper columns in FIGS. 1 and 2); and (b) externally heterologous nucleic acids (round two; see lower columns in FIGS. 1 and 2), as described below. In this regard, internally heterologous nucleic acids refers to heterologous nucleic acids (i.e. nucleic acids that do not have identical counterparts) within each of two or more source groups, and externally heterologous nucleic acids refers to heterologous nucleic acids between the source groups. In the first round, it is generally the untrapped material from input phenotypes which is of primary interest (such untrapped material is said to be "homogenized"). By contrast, in the second round, the material of interest is often the trapped material. This trapped material must necessarily be an artificially-formed, hybrid duplex of similar, yet non-identical cDNA strands, one strand originating from material left untrapped in the first round subtraction step. For use in the VGID[SM] method, nucleic acids are obtained from at least two sources. Best results are obtained where most of the nucleic acids are structurally identical between different sources since this will result in the most effective subtraction in the second round. This situation is most likely to arise where the input source groups are phenotypically identical but for the phenotype-of-interest. Accordingly, the choice of input sources ultimately determines whether the expressed gene-of-interest is identified. Often, the most appropriate samples are obtained from large families containing several affected and unaffected individuals. In the context of positional cloning, the reasons behind this were explained above. In the VGID[SM] method, families (particularly families where consanguinity, i.e. relationship by a common ancestor, is known to exist) may also provide the most appropriate samples, but for entirely different reasons.

Consanguinity gives rise to the direct, non-recombined inheritance of genetic elements which, alone or in association with other factors, can have pathogenic effects. This property of consanguinity can be turned into a considerable advantage in the search for genes directly associated with pathologies. In the presence of consanguinity, it would be expected that all diseased individuals taken from three generations within the same disease-transmitting family (or otherwise inbred) will carry the same disease-causing locus, and hence be identical-by-descent at this locus.

5.1. Genetic Heterogeneity

The various cell lines which are available for a given cell type (e.g. hepatocytes) are characterized by functional similarities and differences (i.e. phenotype) as well as by structural genomic similarities and differences (i.e. genotype). In each cell line, the phenotype arises from a unique source, i.e. the expressed genes of that cell line. Samples of a given tissue originating from different individuals are also characterized by phenotype and genotype. However, in tissue samples, the phenotype arises from the aggregate contributions of the expressed genes of several different cell types and these contributions cannot be individually isolated.

The consequences of the above for gene identification according to the present invention are two-fold. First, tissues are most useful for isolating genes linked to a broadly-defined phenotype, such as the presence of a disorder affecting individual A but not individual B. Tissue samples are less useful for isolation of unknown genes associated with a narrowly-defined phenotype. Second, cell lines are most useful for isolating genes linked to a very clearly-defined molecular function (e.g. a particular form of DNA repair such as that performed by hDinP; see below). The specific methods described below to isolate unknown genes from tissues and cell lines are therefore different.

To elaborate further, it is useful to compare function and genetic makeup in tissues and cell lines.

With regard to function, note that all cells of a cell line population are clonal in origin. That is, they not only descend from a single unique cell, they are actual copies of the ancestor cell. All cells of a cell line are therefore functionally identical. By contrast, a tissue sample is composed of many different cell types carrying out different functions, and each given cell type population is made up of groups of functionally similar cells having different lineages.

With regard to genetic makeup, different cell lines are of completely different origin. That is, the ancestor cells which gave rise to different cell lines came from different individuals. Cell lines therefore carry entirely different genomes. By contrast, the various cell types comprising a given tissue all share the same genome, irrespective of the functional differences among the cell types within the tissue.

Members of a given cell line population initially present very high internal consanguinity and very high functional identity. However, due to fast growth rate in artificial conditions, little or no selective pressures and no possibility to eradicate aberrant cells (i.e. no immune system), members are free to accumulate mutations and transmit them to their direct progeny (so long as these mutations do not compromise basic metabolism). Therefore, a cell line population potentially carries a wide variety of newly-acquired mutations. This not only reduces the structural genomic homogeneity of the population, but also allows different members of the population to express different forms of a given gene (i.e. mutant alleles), as well as genes that are not expressed at all by other members of the cell line population (since a mutation in one gene may affect the expression of other genes). These effects can result in the presence of a wider spectrum of transcripts than might initially be expected from a homogeneous cell population. Awareness of these effects allows for a measure of control by, e.g., careful attention to growth conditions and cell passage number.

These effects are exacerbated when functionally different cell lines are concurrently utilized. The original allelic forms and distribution of genes in the genome of a first cell line will be different from that found in a second cell line, but neither cell line will be subject to enforced internal genomic homogeneity. Furthermore, since the two cell lines are functionally different, the spectrum of expressed transcripts in one population will be different from that present in the other population.

On the other hand, tissue samples comprising many cell types present very high internal consanguinity but very high functional diversity. In tissue samples, unlike cell lines, genomic homogeneity is maintained by the immune system of the individual since most aberrant cells are immediately eradicated. This enforcement of genomic homogeneity by the immune system works to reduce the spectrum of transcripts found in tissues. However, the wide variety of cell types within a given tissue generally more than makes up for this effect. For example, different cell types often express different isoforms of a gene family represented by multiple gene copies in the genome (a phenomenon known as differentiation-specific expression). The net result is the presence of an increasing spectrum of different transcripts expressed in tissues as the number of cell types increases. The final expression complexity level is therefore much higher in tissues than in cell lines.

5.1.1. Genetic Heterogeneity in Cell Lines

When starting with cell line samples, the genes-of-interest to be identified may already be well defined in terms of their precise molecular function (for an example, see Section 6 hereinbelow). The sources of genetic heterogeneity in cell lines are quite different than in tissues. First, there is heterogeneity associated with the genetic differences internal to each cell line. Second, there is heterogeneity associated with the functional characteristics of each cell line. Third, there is heterogeneity associated with the genetic differences between cell lines.

Figure 1:
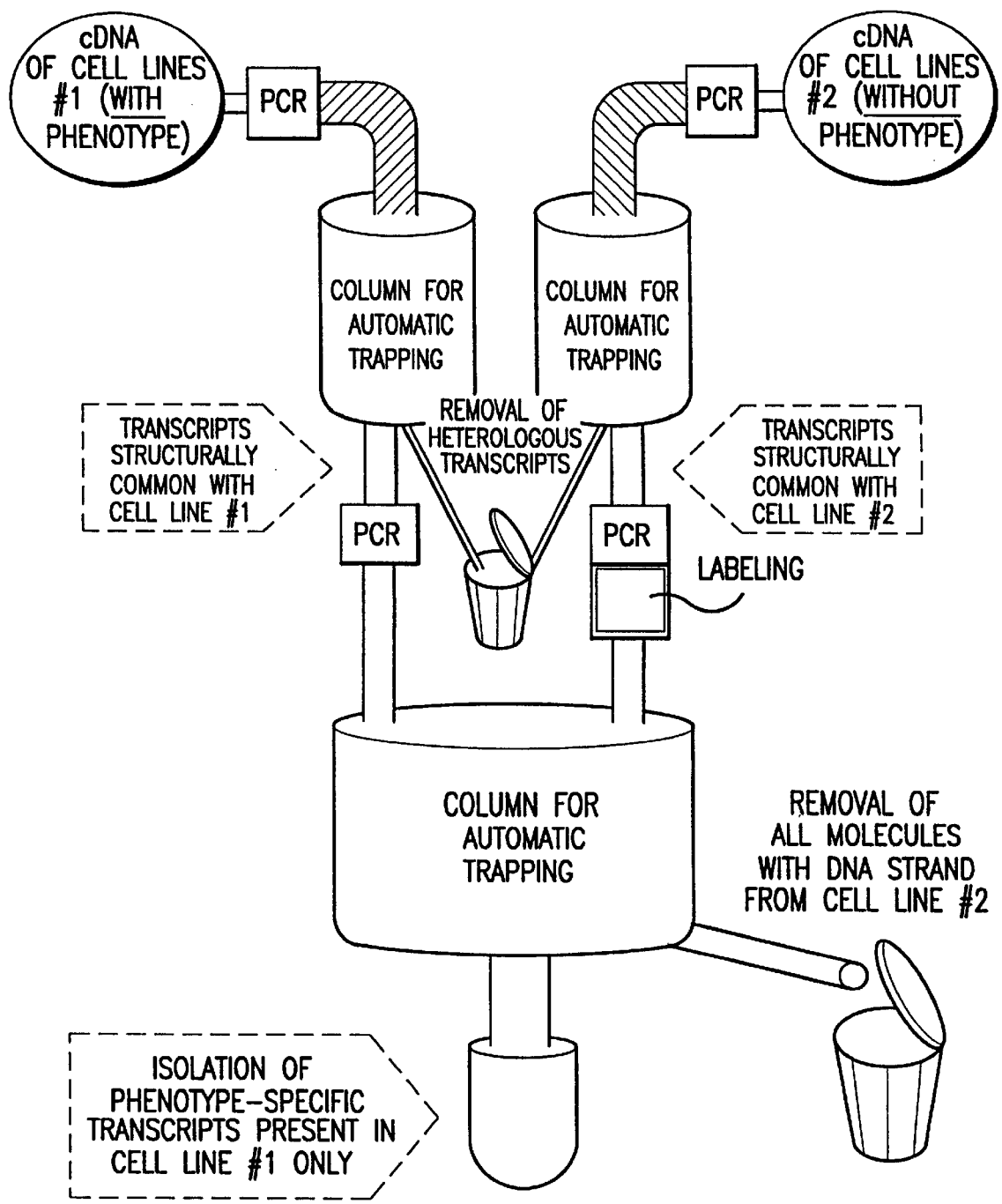
FIG. 1 is a schematic representation of a VGID$^{SM}$ approach for phenotype samples obtained from sources without at least one common ancestor (e.g. cell line samples; healthy and diseased nodes within an individual tissue sample). PCR is polymerase chain reaction.

It is the solution (i.e. removal) of the internal sources of heterogeneity in the first step of the VGID$^{SM}$ method together with the complete retention and utilization of the other two sources of heterogeneity in the second step which leads to the direct isolation of the target genes of interest under the VGID$^{SM}$ approach outlined in FIG. 1. That is, by first retaining only transcripts structurally identical within each cell line, one removes internal heterogeneity. By next removing all transcripts identical between the two cell lines, one is left only with transcripts specific to the key functions associated with the cell line expressing the phenotype-of-interest. The choice of appropriate cell lines is therefore crucial.

The practical aspects of unknown gene isolation from cell line samples are thus entirely defined, as described in detail below in Section 5.2.1. The first step in the approach used for cell lines separately isolates from each cell line nucleic acids (e.g. transcripts) that are structurally identical internally. The second step uses the nucleic acids (e.g. transcripts) from the unspecialized cell line (i.e. "without phenotype" in FIG. 1) to subtract their homologues (i.e. structurally identical externally) from the specialized cell line (i.e. "with phenotype" of interest, see FIG. 1). The second step utilizes MutS, together with another trapping system (e.g. streptavidin-coated beads, see below), to recognize only material originating from the unspecialized cell line (i.e. hybrid as well as native duplexes). The material remaining at the end of the operation corresponds to those few nucleic acids (i.e. transcripts) which are entirely specific (i.e. differentiation-specific) to the specialized cell line.

5.1.2. Genetic Heterogeneity in Tissues

When starting with tissue samples, unlike with cell lines, the genes of interest will usually be defined only in terms of their phenotypic effects (i.e. presence or absence of a disease or trait). Furthermore, there is no complete assurance that, in genetically different individuals, the same phenotypic trait does not have entirely different causes. To further complicate matters, the material utilized (e.g. mRNA) according to the second approach of the VGID$^{SM}$ method comes from a complex source (as explained in detail above) in that: (a) tissue are made of different cell types that cannot be separated; and (b) tissue samples are provided by different individuals.

For tissue samples, three sources of genetic heterogeneity exist to contend with in the isolation of the genes of interest, including disease (affected) genes. First, there is heterogeneity associated with a target tissue comprised of multiple cell types. Second, there is heterogeneity associated with phenotypic differences among normal and affected individuals which do not give rise to disease. Third, there is heterogeneity associated with the genetic differences among normal and affected individuals which gives rise to the disease.

Figure 2:
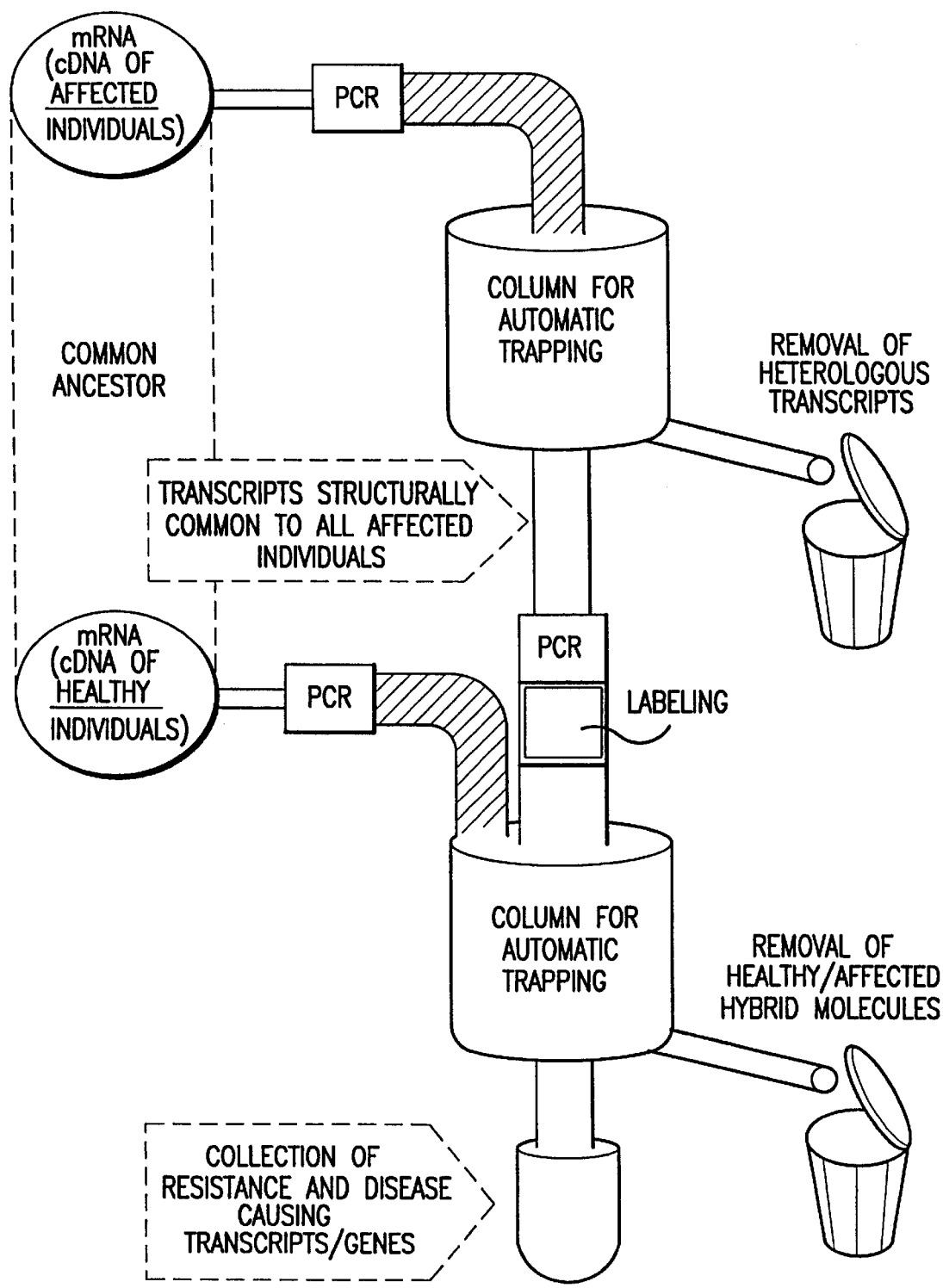
FIG. 2 is a schematic representation of a VGID$^{SM}$ approach for phenotype samples obtained from sources having at least one common ancestor (e.g. tissue samples from healthy and disease-affected siblings).

It is the solution (i.e. removal) of the first and second sources of heterogeneity which directly leads to isolation of disease genes using the VGID$^{SM}$ approach outlined in FIG. 2. By selecting as tissue donors several affected and several healthy members of the same genetic group (i.e. consanguineous donors) and then pooling the tissue extracts into only two groups, three things are accomplished. First, genetic differences between affected and unaffected individuals are considerably reduced; second, phenotypic homogeneity among the affected individuals is vastly increased; and third, genetic heterogeneities within each sample group are homogenized.

The practical aspects of unknown gene isolation from tissue samples are thus entirely defined, as described in detail below in Section 5.2.2. The first step utilizes mismatch binding chromatography to isolate transcripts which are structurally identical among affected individuals (i.e. column flow through, see upper column in FIG. 2). These structurally identical transcripts are then used to isolate their structurally different counterparts from the unaffected pool in a second round of mismatch binding chromatography (see lower column in FIG. 2). In this way, none of the transcripts structurally identical between affected and unaffected pools will be trapped by mismatch binding and none of the transcripts structurally different within the unaffected (healthy) pool will be selectively recovered from the material released from binding.

5.2. Two Approaches for the VGID$^{SM}$ Method

The VGID$^{SM}$ method is designed to identify genes by isolating nucleic acids derived from transcripts that are associated with a given phenotype in the complete absence of pertinent molecular information. In this context, a phenotype corresponds to a detectable biological difference between otherwise-comparable tissues or cell population samples. Biological differences may range from narrow, well-defined metabolic functions (e.g. DNA repair) to broad, less-well-defined clinical observations (e.g. schizophrenia or Alzheimer's disease). As opposed to other expressed transcript isolation methods (e.g. cDNA subtraction technologies), the VGID$^{SM}$ process does not require subtraction steps based upon known sequences. Moreover, the VGID$^{SM}$ process does not require any molecular choices to be made by the user. Instead, the VGID$^{SM}$ user need only select the input phenotypes for comparison.

The operating principle of the VGID$^{SM}$ process makes use of the fact that any detectable biological difference existing between two or more otherwise-similar samples almost always depends, at least in part, from the presence of concomitant transcriptional differences between these samples. In order to isolate transcripts associated with a phenotype-of-interest using the VGID$^{SM}$ method, one does not speculate regarding possible structures that need to be isolated or discarded. Instead, one merely chooses the input phenotypes for use in the VGID$^{SM}$ comparison assay.

While the VGID$^{SM}$ method does not allow one to directly identify (i.e. by mismatch binding) promoter-associated mutations contained in non-transcribed portions of genes, any transcripts that are over- or under-expressed as a result of such mutations can be identified (e.g. see the first approach described in Section 5.3.1 and the Example in Section 6 hereinbelow). In summary, the VGID$^{SM}$ process allows isolation and identification of overexpressed, underexpressed or mutated transcripts that specifically differ between two (or more) transcript source populations.

The VGID$^{SM}$ method may be applied to any two or more nucleic acid source populations. Nucleic acid source populations used in the VGID$^{SM}$ method are derived from transcript sources (i.e. messenger RNA from cellular sources) preferably by converting the mRNA to double-stranded cDNA. Transcript sources include, but are not limited to, animals, plants, and microorganisms, including viruses. For example, the VGID$^{SM}$ method may be applied for the isolation of microbial genes conferring resistance to toxic compounds or metabolites. As another example, the VGID$^{SM}$ method may be applied to isolate plant genes conferring desirable traits for crop production. For tissues and cell lines, transcript sources may include, but are not limited to: (a) tissue nodes within an individual tissue sample (first approach); (b) cell line samples (first approach); and (c) tissues samples originating from familial clusters having consanguinity (second approach). The first and second VGID$^{SM}$ approaches that can be most commonly used for these various transcript sources are described in detail below.

5.2.1. First Approach: Cell Lines or Sole Tissue Sample

This approach is particularly well suited to the study of genes associated with specific metabolic functions (e.g. in a cell line displaying the phenotype-of-interest) or with disease processes where affected tissue samples are limited and where control tissue from healthy individuals cannot be obtained. This approach also allows comparative study of sporadic versus familial forms of a given pathology.

Three different yet complementary transcript isolations may be performed using the first VGID$^{SM}$ approach, as follows: (i) isolation of transcripts overexpressed (or unilaterally expressed) in the presence of the phenotype-of-interest; (ii) isolation of transcripts underexpressed (or unilaterally repressed) in the presence of the phenotype-of-interest; and (iii) isolation of transcript variants (i.e. mutants) associated with the phenotype-of-interest.

The overall experimental scheme for using the VGID$^{SM}$ method under the first approach is illustrated in FIG. 1. The first approach identifies a gene or genes underlying a defined phenotype in two steps by, first, removing mismatched duplex nucleic acid molecules formed from hybridization within each of two source populations and, second, retaining mismatched duplex nucleic acid molecules formed from hybridization between the two populations. What follows is a preferred embodiment of the first approach; various modifications that can be made will be apparent to one of skill in the art (e.g. see Section 5.3 hereinbelow).

Selection of input phenotypes is performed by the user, and can be carried out as desired. Nevertheless, preferred guidelines for phenotype selection (choosing transcript sources) are provided hereinbelow in Section 5.4. Following phenotype selection, an independent (i.e. separate) cDNA library is generated for each of two or more transcript sources which differ in the phenotype-of-interest. Cell lines may be used as transcript sources. Alternatively, a single tissue sample from an affected (i.e. disease) individual may also be used. In the latter instance, different cellular nodes are isolated from within the single tissue sample, each node representing a different pathological stage or phenotypic state.

In one embodiment, samples from transcript sources are processed in pairs, each member of a pair representing a different phenotype. In another embodiment, samples are processed in groups of three or more (a.k.a. multiplex VGID$^{SM}$ methodology). The two steps of the method can be further subdivided into several parts for clarity of illustration. For example, in the preferred embodiment described below, the first step comprises parts 1–3 and the second step comprises parts 4–6, as follows.

Part 1. Each cDNA library originating from each independent source (e.g. cell line or tissue node) is subjected to a limited PCR amplification (15–20 cycles) in order to linearize the cDNA inserts.

Part 2. The PCR products obtained from each source are independently (i.e. without yet combining materials from different sources) denatured and reannealed.

Following parts 1 and 2, transcripts that present structural differences within each source population will give rise to mismatched heteroduplex molecules. The heterologous transcripts in these heteroduplex molecules arise from random mutations not associated with the phenotype-of-interest. This heteroduplex formation occurs since the random mutations encountered should be common to only a portion of, and not to all, individual cells within each source population.

Part 3. The reannealed PCR products originating from each source are exposed independently to a first round of mismatch column chromatography (see the top two columns in FIG. 1; e.g. columns may be packed with MutS-coated glass beads for "automatic trapping" of the mismatch-containing heteroduplexes).

In part 3, mismatched heteroduplexes become trapped in the column. After several cycles of denaturation and random reannealing followed by trapping, the column flow through contains primarily transcripts that are structurally common to all cells within the source. That is, any heterologous transcripts within the source are largely removed from the material being analyzed during part 3 (see upper waste bin in FIG. 1 labeled "removal of heterologous transcripts").

Part 4. The cDNA inserts present in the flow-through obtained from each cell line are independently PCR amplified and labeled.

In part 4, PCR amplification serves two purposes. First, this PCR increases the number of copies of the remaining individual cDNA inserts which originated from each source population. Second, and more importantly, PCR allows independent labeling of inserts originating from each source population. In this way, one is able to selectively remove or retrieve inserts originating from a given source population. For example, FIG. 1 illustrates using two cell lines as source populations, with cell line # 1 displaying the phenotype-of-interest ("with phenotype" in FIG. 1). Here, inserts that will not be part of the final analysis are labeled for removal (i.e. transcripts not associated with the phenomenon of interest; see lower right waste bin "removal of all molecules with DNA strand from cell line # 2"; see also hereinbelow).

The labels used in part 4 are attached to the primers utilized in the relevant PCR reaction. Suitable labels include molecules that can be specifically bound and subsequently removed from solution together with their attached PCR products. For example, such labels may be: (a) biotin molecules recognized by streptavidin coated onto solid supports; or (b) short peptides recognized by specific monoclonal antibodies attached to solid supports. The solid supports used may be beads, resins, nitrocellulose paper, or others well known to those skilled in the art.

Part 5. The PCR amplified DNA, obtained from independent sources and subjected to parts 1–4, are now combined, denatured and reannealed.

Part 6. The reannealed PCR products are then exposed to a second round of mismatch column chromatography (see the lower column in FIG. 1).

In the FIG. 1 approach, the material trapped in the lower column is primarily mismatched heteroduplexes composed of one non-labeled strand originating from cell line # 1 and one labeled strand originating from cell line # 2. This material therefore represents transcripts expressed by both cell lines but carrying cell line-specific mutations, and may either be discarded (see lower right waste bin in FIG. 1) or recovered, cloned, and analyzed. It is to be well noted that if parts 2 and 3 have not first been carried out, any material trapped by the source combination in parts 5 and 6 would not be worth recovering since it would be heavily contaminated by random heterologies present in each source cell line.

Recovery of trapped heteroduplexes from a MutS mismatch binding column can be performed in at least two ways. First, the column may be filled with an ATP-containing buffer. The presence of ATP allows the ATPase activity of MutS to release trapped heteroduplexes. The concentration range of ATP suitable for effecting release is from about 1 mM to about 6 mM ATP; the optimal concentration of ATP for effecting release is about 3 mM (see e.g. Allen et al., 1997, EMBO J. 16, 4467–4476). Recovery of trapped heteroduplexes using ATP has the added advantage of regenerating the column for subsequent use. Second, recovery may be effected using a protease (with the caveat that certain proteases may not be suitable for use with certain short peptide labels). For example, the column may be treated with a protease-containing buffer (e.g. proteinase K), resulting in the destruction of the MutS protein molecules immobilized in the column and the subsequent release of the trapped heteroduplexes.

Trapped material from the lower column in the example of FIG. 1 is composed of one labeled and one non-labeled strand. This material may be discarded if one is only interested in transcripts from cell line # 1 (see lower right waste bin in FIG. 1). Alternatively, this material may be specifically recovered (e.g. using streptavidin or antibody-coated beads, depending upon the label used at part 4 above), for an examination of the genetic differences in transcripts expressed by both input cell lines. If this specific recovery is desired, the isolated material is PCR amplified over a few cycles for production of clonable fragments having non-labeled 5' ends. It is noteworthy that recovery here preserves the original structures specific to each cell line since, in the PCR reaction, each strand of the original mismatched heteroduplex independently gives rise to a perfectly matched homoduplex. It is also possible to separately clone the transcripts arising from each cell line source.

This is accomplished by denaturing the heteroduplexes released from the column and subsequently bound to the label-binder (e.g. streptavidin beads), separating the pellet (containing labeled strands) from the supernatant (containing unlabeled strands), and performing two PCR reactions using material in the pellet and the supernatant as separate templates.

The material untrapped by the lower column in the schematic of FIG. 1 (i.e. column flow-through) potentially contains three types of mismatch-free duplex DNA molecules, as follows. First, it can contain unlabeled homoduplexes which primarily represent transcripts that are overexpressed or unilaterally expressed by the "non-labeled" cell line (i.e. transcripts that have no, or very few, counterparts in the "labeled" cell line). Second, it can contain homoduplexes labeled on both strands which primarily represent transcripts that are overexpressed or unilaterally expressed by the "labeled" cell line (i.e. transcripts that have no, or very few, counterparts in the "non-labeled" cell line). Third, it can contain hybrid homoduplexes labeled on one strand only which represent transcripts common to both cell lines expressed at comparable levels.

As in the case of the mismatched material, singly-labeled homoduplex hybrids as well as doubly labeled homoduplexes can be specifically removed from solution, leaving behind transcripts originating from the non-labeled cell line that have no counterparts in the labeled cell line. It should be noted that transcripts specific to the labeled cell line (i.e. doubly-labeled homoduplexes) cannot be isolated from transcripts common to both cell lines (i.e. singly-labeled homoduplex hybrids) under the scheme illustrated in FIG. 1. In order to isolate these transcripts, the labeling strategy is reversed and the experiment repeated. Alternatively, a different labeling strategy altogether (i.e. two-label strategy) may be employed in which transcripts originating from cell line #1 are not left unlabeled. Here, the "labelling" step diagrammed in FIG. 1 is performed on both upper column flow throughs, using a distinct label for each column.

Thus, in the single experiment outlined above, transcripts specific to one cell line (or tissue node) can be isolated from transcripts that bear cell line-specific (or node-specific) mutations. It is to be further noted that, by using two or more different labeling agents (e.g. biotin and one or more short peptides), the approach can be multiplexed. That is, using multiple labels, several different cell lines or tissue nodes can be analyzed concurrently and the transcripts specific to each component individually isolated. Multiplexing is limited only by the number of available labels and the user's imagination in choosing input phenotypes.

5.2.2. Second Approach: Samples from Organisms Having Consanguinity

The second approach for using the VGID$^{SM}$ method is particularly appropriate for the isolation of founder effect mutations from population samples having consanguinity, i.e. at least one recent common ancestor. What follows are preferred embodiments of the second approach; various modifications that can be made will be apparent to one of skill in the art (e.g. see Section 5.3 hereinbelow). In one preferred embodiment, individuals of a population have a common parent or grandparent. In another embodiment, individuals of a population share a common ancestor within three generations (i.e. great grandparent). In still another embodiment, individuals of a population share a common ancestor within ten generations. Here, obtaining control tissue samples from healthy relatives is an absolute requirement. While the overall procedure, which is illustrated in FIG. 2, is similar to the first approach in that it utilizes mismatch binding, there are important differences under the second approach, as described below.

First, as just mentioned, affected and healthy individuals contributing tissue samples must all share at least one recent common ancestor (i.e. consanguineous individuals). Of course, the population labels "affected" (or "diseased") and "healthy" (or "control") are arbitrary in that two input populations differing in a phenotype-of-interest (and not necessarily a disease) are all that is required, so long as all individuals contributing to the input populations have consanguinity.

Second, at least two (2) affected and two (2) healthy relatives should be sampled for optimum results. For best results, samples should be collected from five to six diseased individuals and an equal number of healthy individuals. Individuals need not all come from the same nuclear family (defined herein as having a common mother or father) and they need not be age-matched.

Third, the cDNA libraries constructed from each tissue sample should be normalized in order to reduce the chances of missing rare transcripts. Library normalization techniques include any of those known to one skilled in the art, such as those described in Section 5.3. hereinbelow.

Fourth, a homogenization step is performed on the samples obtained from affected individuals. Homogenization is carried out as follows: A sample is obtained from each affected individual and is used to construct an independent (i.e. separate) cDNA library; each library is then PCR amplified and the resultant products from all affected individuals are mixed together. Denaturation, reannealing and trapping of mismatched duplexes over an immobilized MutS column is performed (see upper column in FIG. 2). Although this homogenization step will result in a 50% reduction in frequency of heterozygous mutant transcripts in the flow-through material, the step is preferable to insure the isolation of transcripts structurally common to all affected individuals (see upper column flow through in FIG. 2). The material recovered in the upper column flow through is then PCR-labeled as described above.

Fifth, a homogenization step like that performed on affected samples is not applied to healthy (i.e. control) samples. Instead, PCR material obtained from each control cDNA library is mixed together and then directly added to the affected, PCR-labeled products obtained from the upper column flow through illustrated in FIG. 2. This complex mixture is then denatured and randomly reannealed before exposure to the lower MutS column illustrated in FIG. 2. The major reason behind this step is to provide an efficient counterbalance to the effects of consanguinity. The more closely related affected individuals are, the greater the number of structurally identical loci they hold in common. As a result, the pool of transcripts remaining after the homogenization step may be quite large, but only a few of these are likely to be relevant to the disorder. Furthermore, familial genetic disorders are often associated with specific mutations that are frequent among affected members of the disease-transmitting family. However, this does not mean that unaffected individuals are mutation-free at the loci concerned. It simply means that unaffected individuals have inherited polymorphisms other than those associated with the disease, and there could be many such silent polymorphisms.

The net result of the above considerations is that while affected individuals within a disease-transmitting family are very likely to share the same mutations, healthy members of the family do not necessarily have the same "healthy" alleles. Therefore, in order to identify the mutant loci associated with a familial disorder (together with healthy allelic forms), it is highly advisable to first isolate transcripts structurally common to all affected individuals (i.e. to reduce the complexity by homogenization). At the same time, it is highly advisable to maintain as much diversity as possible within control samples in order to maximize chances of isolating all healthy allelic variants.

Accordingly, in approach 2, mismatched heteroduplexes that are trapped by the second column (i.e. lower column in FIG. 2) have potentially two sources: (a) unlabeled heteroduplexes with both strands originating from healthy individuals; and (b) hybrid heteroduplexes labeled on one strand originating from affected individuals and representing transcripts structurally common to all affected individuals which are also present in their healthy relatives with a sequence difference. Thus, any mutant alleles associated with disease, as well as their "healthy" counterparts, will be found in the trapped material. Following release of the trapped material with either ATP or proteinase K (as described above) the labeled strand can be specifically removed from solution.

The flow through material of the second (lower) column in FIG. 2 potentially contains: (a) singly-labeled mismatch-free duplexes representing transcripts structurally common to affected and unaffected relatives; (b) doubly-labeled mismatch-free duplexes representing transcripts structurally common to affected relatives only; and (c) unlabeled mismatch-free duplexes representing transcripts present in unaffected relatives only. These can be specifically recovered by removing from solution all labeled, mismatch-free duplexes using a label binder (e.g. streptavidin-coated beads).

It is to be noted that transcripts specific to affected individuals only (i.e. doubly labeled mismatch-free duplexes) cannot be directly recovered from the lower (second) column of FIG. 2 using this approach. To isolate such transcripts, it would be necessary to reverse the labeling strategy and repeat the experiment (i.e. label during the lower left "PCR" diagrammed in FIG. 2). When labeling only healthy individuals, however, mutations associated with disease cannot be isolated from mismatched heteroduplexes trapped in the lower MutS column (singly-labeled mismatched hybrids); further, the vast majority of trapped material will originate from the healthy individuals alone due to the absence of selective recovery of transcripts structurally common to all healthy individuals (i.e. homogenization). Furthermore, a selective recovery step (i.e. a parallel first column) to homogenize the nucleic acid population cannot be carried out on healthy relatives without a serious risk of losing the relevant alleles through the presence of silent polymorphisms which will generate numerous mismatched heteroduplexes at the denaturation-reannealing step and that would remain trapped (upper waste bin of FIG. 2) in the first round of MutS chromatography. Alternatively of course, as described for the first approach in Section 5.3.1. above, more than one label may be used.

It should be well noted that the higher the inbreeding levels in the families contributing normal and disease samples, the fewer the number of mismatched loci ultimately obtained. Although all mismatched loci identified in this way will serve as markers to differentiate healthy from diseased individuals, it should also be noted that silent genetic polymorphisms (i.e. harmless, non-disease-associated changes in DNA) will be identified as well. Accordingly, best results in identifying disease genes will be obtained using highly inbred populations since inbreeding reduces the number of silent genetic polymorphisms between input sources to a minimum.

The genetic loci identified by the above procedure can be used as probes in population studies carried out by the standard immobilized MutS genotyping approach on genomic DNA obtained from affected individuals and healthy individuals (see Wagner et al., 1995, Nucl. Acids Res. 23, 3944–3948). Subsequent statistical analysis, well known to those skilled in the art, will then easily identify the loci and the alleles associated with susceptibility and resistance to the disease.

In summary, the second VGID$^{SM}$ approach provides numerous advantages in the search for disease-causing genes from consanguineous sample populations. First, the approach turns highly inbred populations into an asset as opposed to a liability. Second, the approach allows rapid gene identification in cases where the lack of physiological and/or biochemical information is such that there is no basis on which possible candidate genes could be proposed. Third, the approach allows rapid identification of genes and all alleles directly and indirectly associated with susceptibility and resistance to a disease. Fourth, the approach can be applied to any consanguineous population, in many contexts, ranging from the search for susceptibility or resistance genes associated with multifactorial diseases, to the search for rare genes conferring desirable monogenic traits.

The number of clones sequenced from the output obtained under either approach to the VGID$^{SM}$ method is as desired by the user. Optionally, one or more (e.g. five or six) clones among those initially identified are sequenced to sample the results. Nucleic acid sequences are then computer analyzed for open reading frames, and used to drive a protein database search to determine whether any portions correspond to portions of known proteins. It is preferable to perform such a search by translating the nucleotide sequence into all six possible reading frames (3 in each direction) in order to detect any proteins existing in the database. Of course, the VGID$^{SM}$ method will also identify genes not yet represented in any database. In this instance, gene function may be inferred from the observed functional differences between the input phenotypes.

5.3. Miscellaneous Methods Used in Conjunction with the VGID$^{SM}$ Method

Nucleic acid (e.g. mRNA) extraction and cDNA synthesis are performed using techniques well known to those skilled in the art. For example, Gibco-BRL Trizol kits may be used for mRNA preparation and Promega Universal Riboclone kits may be used for cDNA synthesis, both according to the manufacturers' protocols. The synthesized cDNA may be size-selected by any of the techniques well known to those skilled in the art. For example, agarose gel electrophoresis, sucrose density gradient chromatography, molecular sieve chromatography or high performance liquid chromatography may be used. The cDNA fragments subsequently cloned may range from below 100 bases up to 10 kilobases or more. However, it should be recognized that the optimum size for error-free PCR is about 600 bases. It should further be recognized that the optimum size for error-free reverse transcription is about 400 bases. A suitable viral reverse transcriptase is that obtained from Maloney murine leukemia virus (MMLV). If cDNA is fractionated by agarose gel electrophoresis, it may be recovered from gel slices using a variety of techniques well known in the art. For example, fragments may be collected by overnight diffusion into a small liquid volume, or by using one of many commercially-available kits, such as Gel-Clean (Promega) or QiaQuick (Qiagen).

There are no special considerations when choosing a vector for cDNA library construction. The VGID$^{SM}$ method will work independently of the specific library vector employed. Often, the best vector will be the one which the user is most familiar with. Of course, the most important consideration for best results will be to ensure that the libraries constructed represent rare as well as abundant transcripts, e.g. by normalizing the libraries.

Library inserts are PCR amplified using oligonucleotide primers (oligonucleotides) specific to the cloning vector. Labeled oligonucleotides are used as suitable for the particular experimental design being used. For example, in the first VGID$^{SM}$ approach (see FIG. 1), the oligonucleotides used for the cell line #2 library are labeled with biotin (see Example in Section 6). Any heat stable polymerase may be used, but those with the lowest error rate available are preferred to reduce the number of mismatches created during the PCR. Examples of suitable enzymes are Taq DNA polymerase and Pfu DNA polymerase. It is important to remember that large numbers of cycles are not required since the goal is simply to produce linearized (and, where needed, labeled) fragments from the library. The PCR products are column purified, heat-denatured, annealed, and cooled to room temperature.

Subtraction of heteroduplex DNA is performed on renatured, cooled PCR products using mismatch-binding chromatography. This may be conveniently performed in a variety of formats including a test tube format, a column format, or any other format selected by the user which permits heteroduplex DNA to bind to immobilized mismatch binding protein. For example, DNA in a reaction buffer (e.g. 350 ng in 100 μl) may be placed into a vessel (e.g. 0.5 ml Eppendorf tube) containing MutS (e.g. 10 μg) adsorbed onto glass beads (e.g. 100 μm diameter, acid washed, from Sigma Chemical Co.). The incubation phase is performed for a time sufficient to allow mismatch binding to occur (e.g. 15–55 min). The incubation time may vary according to measures taken to increase the contact surface area between the immobilized mismatch binding protein and the reannealed cDNA. Such measures may include slowly rotating the vessel or placing the vessel in a horizontal position. The unbound, reannealed PCR products left free in solution may be recovered as column flow through (in a column format) or as supernatant following centrifugation (in a test tube format).

It is often advantageous to repeat the mismatch binding protein mediated trapping operation using fresh immobilized protein a total of two to four times to insure removal of all mismatched heteroduplexes. The optimum number of repetitions required will depend primarily on the relative amounts of mismatched heteroduplexes to be trapped and the quantity of protein available for trapping in each round.

It will be advantageous, in some instances, to use an excess of DNA from one source over the other when performing a subtraction. For example, prior to performing the second round of trapping using the approach illustrated in FIG. 1, an excess of DNA from the source without the phenotype-of-interest (i.e. cell line # 2) may be used over DNA from the source with the phenotype-of-interest (i.e. cell line # 1) in order to insure the complete removal of all transcripts which are identical between the two sources. In this regard, the source without the phenotype-of-interest may be thought of as a molecular mop for removal of undesired transcripts. The ratio of excess DNA may vary over a wide range, i.e. from 1.01:1.0 to 100:1. It will often range from 1.1:1.0 to 10:1. It will most often range from 1.5:1 to 6:1. A recommended starting ratio is 3:1.

For best results in obtaining cDNAs which represent rare transcripts encoding the phenotype-of-interest, preparation of normalized cDNA libraries from each input mRNA source is performed. A portion of each input library should be preserved in non-normalized form for further analysis, if desired. Normalization techniques known in the art include, but are not limited to, those described in the following: Soares and Efstratiadis, Jun. 10, 1997, Normalized cDNA libraries, U.S. Pat. No. 5,637,685; Sankhavaram et al., March 1991, Construction of a uniform-abundance (normalized) cDNA library, *Proc. Natl. Acad. Sci. USA* 88, 1943–1947; and Ko, 1990, An equalized cDNA library by the reassociation of short double-stranded cDNAs, *Nucl. Acids Res.* 18, 5709.

Suitable mismatch binding proteins that can be used have been previously described (see e.g. Wagner, May 11, 1995, Immobilized mismatch binding protein for detection or purification of mutations or polymorphisms, International Publication Number WO 95/12689). A preferred mismatch binding protein is characterized by its ability to bind DNA-DNA duplexes containing mispaired or unpaired bases (Id. at 13). For example, in addition to *E. coli* MutS, the mismatch binding protein may be human MSH2 (Fishel et al., 1994, Science 266, 1403–1405; Fishel et al., 1994, Cancer Res. 54, 5539–5542; Mello et al., 1996, Chem. Biol. 3, 579–589), an hMSH2-hMSH6 protein complex (Acharya et al., 1996, Proc. Natl. Acad. Sci. U.S.A. 93, 13629–13634; Gradia et al., 1997, Cell 91, 995–1005), or homologues from various other organisms such as yeast (Miret et al., 1993, J. Biol. Chem. 268, 3507–3513).

Suitable conditions for annealing (i.e. hybridization) reactions have been well described, for example, by Sambrook et al., 1989, in *Molecular Cloning, A Laboratory Manual*, 2d Edition, Cold Spring Harbor Laboratory Press, Cold Spring Harbor, N.Y.

Separation of labeled strands from unlabeled strands or from differently-labeled strands is performed using standard techniques. For example, biotin-labeled strands bound to streptavidin-coated beads may be placed into a first container or vessel for heat denaturation into single strands. After denaturation, the supernatant is removed from the first container and transferred to a second container, resulting in separation of labeled strands from unlabeled or differently-labeled strands. Each set of strands can now be independently PCR amplified (for a few cycles), cloned and sequenced.

Suitable nucleic acid labels and their partner molecules or agents (i.e. binding partners) include, but are not limited to, biotin and streptavidin, and short peptide labels and monoclonal antibodies. These are discussed in Section 5.8 and 5.9 infra. Suitable methods of linearizing inserts in a cDNA library include, but are not limited to, PCR and digestion with restriction enzyme(s). Suitable methods of amplifying cDNA include, but are not limited to, PCR and propagation in bacteria.

5.3.1. DNA Amplification

The polymerase chain reaction (PCR) may be used in connection with the invention to amplify a desired sequence from a source (e.g., a tissue sample, a genomic or cDNA library). oligonucleotide primers representing known sequences can be used as primers in PCR. PCR is typically carried out by use of a thermal cycler (e.g., from Perkin-Elmer Cetus) and a thermostable polymerase (e.g., Gene Amp™ brand of Taq polymerase). The nucleic acid template to be amplified may include but is not limited to mRNA, cDNA or genomic DNA from any species. The PCR amplification method is well known in the art (see, e.g., U.S. Pat. Nos. 4,683,202, 4,683,195 and 4,889,818; Gyllenstein et al., 1988, Proc. Nat'l. Acad. Sci. U.S.A. 85, 7652–7656;

Ochman et al., 1988, Genetics 120, 621–623; Loh et al., 1989, Science 243, 217–220).

Any prokaryotic cell, eukaryotic cell, or virus, can serve as the nucleic acid source. For example, nucleic acid sequences may be obtained from the following sources: human, porcine, bovine, feline, avian, equine, canine, insect (e.g., Drosophila), invertebrate (e.g., *C. elegans*), plant, etc. The DNA may be obtained by standard procedures known in the art (see, e.g., Sambrook et al., 1989, Molecular Cloning, A Laboratory Manual, 2d Ed., Cold Spring Harbor Laboratory Press, Cold Spring Harbor, N.Y.; Glover (ed.), 1985, DNA Cloning: A Practical Approach, MRL Press, Ltd., Oxford, U.K. Vol. I, II).

5.3.2. Adjusting Stringency

Other methods available for use in connection with the methods of this invention include nucleic acid hybridization under low, moderate, or high stringency conditions (e.g., Northern and Southern blotting). Methods for adjustment of hybridization stringency are well known in the art (see, e.g., Sambrook et al., 1989, Molecular Cloning, A Laboratory Manual, 2d Ed., Cold Spring Harbor Laboratory Press, Cold Spring Harbor, N.Y.; see, also, Ausubel et al., eds., in the Current Protocols in Molecular Biology series of laboratory technique manuals, 1987–1994 Current Protocols, 1994–1997 John Wiley and Sons, Inc.; see, especially, Dyson, N.J., 1991, Immobilization of nucleic acids and hybridization analysis, In: Essential Molecular Biology: A Practical Approach, Vol. 2, T. A. Brown, ed., pp. 111–156, IRL Press at Oxford University Press, Oxford, U.K.; each of which is incorporated by reference herein in its entirety). Salt concentration, melting temperature, the absence or presence of denaturants, and the type and length of nucleic acid to be hybridized (e.g., DNA, RNA, PNA) are some of the variables considered when adjusting the stringency of a particular hybridization reaction according to methods known in the art.

Conditions of low stringency, by way of example and not limitation, may be as follows (see, also, Shilo and Weinberg, 1981, Proc. Natl. Acad. Sci. U.S.A. 78, 6789–6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film.

Conditions of high stringency, by way of example and not limitation, may be as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography.

5.3.3. Oligonucleotide Analogs

Oligonucleotides used in conjunction with the invention are often ranging from 10 to about 50 nucleotides in length. In specific aspects, an oligonucleotide is 10 nucleotides, 15 nucleotides, 20 nucleotides or 50 nucleotides in length. An oligonucleotide can be DNA or RNA or chimeric mixtures or derivatives or modified versions thereof, or single-stranded or double-stranded, or partially double-stranded. An oligonucleotide can be modified at the base moiety, sugar moiety, or phosphate backbone, or a combination thereof. An oligonucleotide may include other appending groups, such as biotin, fluorophores, or peptides.

An oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and 2,6-diaminopurine.

An oligonucleotide may comprise at least one modified phosphate backbone selected from the group including but not limited to a phosphorothioate, a phosphorodithioate, a phosphoramidothioate, a phosphoramidate, a phosphordiamidate, a methylphosphonate, an alkyl phosphotriester, and a formacetal or analog thereof.

An oligonucleotide or derivative thereof used in conjunction with the methods of this invention may be synthesized using any method known in the art, e.g., by use of an automated DNA synthesizer (such as are commercially available from Biosearch, Applied Biosystems, etc.). As examples, phosphorothioate oligonucleotides may be synthesized by the method of Stein et al. (Stein et al., 1988, Nucl. Acids Res. 16, 3209), methylphosphonate oligonucleotides can be prepared by use of controlled pore glass polymer supports (Sarin et al., 1988, Proc. Natl Acad. Sci. U.S.A. 85, 7448–7451), etc. An oligonucleotide may be an α-anomeric oligonucleotide. An α-anomeric oligonucleotide forms specific double-stranded hybrids with complementary RNA in which, contrary to the usual β-units, the strands run parallel to each other (see Gautier et al., 1987, Nucl. Acids Res. 15, 6625–6641).

Oligonucleotides may be synthesized using any method known in the art (e.g., standard phosphoramidite chemistry on an Applied Biosystems 392/394 DNA synthesizer). Further, reagents for synthesis may be obtained from any one of many commercial suppliers.

Spacer phosphoramidite molecules may be used during oligonucleotide synthesis, e.g., to bridge sections of oligonucleotides where base pairing is undesired or to position labels or tags away from an oligonucleotide portion undergoing base pairing. The spacer length can be varied by consecutive additions of spacer phosphoramidites. Spacer phosphoramidite molecules may be used as 5'- or 3'-oligonucleotide modifiers. Such spacers include Spacer Phosphoramidite 9 (i.e., 9-O-Dimethoxytrityl-triethyleneglycol, 1-[(2-cyanoethyl)-(N,N-diisopropyl)]-phosphoramidite, and Spacer Phosphoramidite 18 (i.e., 18-O-Dimethoxytrityl-hexaethyleneglycol, 1-[(2-cyanoethyl)-(N,N-diisopropyl)]-phosphoramidite), both available from Glen Research (Sterling, Va.).

Other spacers are available for use in standard oligonucleotide synthesis. For example, Spacer Phosphoramidite C3 and dspacer Phosphoramidite can be used to destabilize undesirable self-hybridization events within capture oligonucleotides or to destabilize false hybridization events between incorrectly-matched template/probe complexes. Such spacers, when positioned at the 3' end of an oligonucleotide, will also prevent incorrect extension products from being generated when included in a PCR reaction mixture.

One spacer available from Glen Research, Spacer Phosphoramidite C3 (i.e., 3-O-Dimethoxytrityl-propyl-1-[(2-cyanoethyl)-(N,N-diisopropyl)]-phosphoramidite), can be added to substitute for an unknown base within an oligonucleotide sequence.

A branching spacer may be used as one method to increase label incorporation into an oligonucleotide. Such a branching spacer may also be used to increase a detectable signal by hybridization through multiply branched capture probes or PCR primers. Branching spacers are available commercially, e.g., from Glen Research.

Biotinylated oligonucleotides are well known in the art. An oligonucleotide may be biotinylated using a biotin-NHS ester procedure. Alternatively, biotin may be attached during oligonucleotide synthesis using a biotin phosphoramidite (Cocuzza, 1989, Tetrahed. Lett. 30, 6287–6290). One such biotin phosphoramidite available from Glen Research is 1-Dimethoxytrityloxy-2-(N-biotinyl-4-aminobutyl)-propyl-3-O-(2-cyanoethyl)-(N,N-diisopropyl)-phosphoramidite. This compound also has a branch point to allow further additions. The branched spacer used in this biotin phosphoramidite has been described by Nelson et al. (Nelson et al., 1992, Nucl. Acids Res. 20, 6253–6259).

Another 5'-biotin phosphoramidite, namely [1-N-(4,4'-Dimethoxytrityl)-biotinyl-6-aminohexyl]-2-cyanoethyl-(N,N-diisopropyl)-phosphoramidite, may be used to biotinylate an oligonucleotide. This compound is sold by Glen Research under license from Zeneca PLC.

Fluorescent dyes may also be incorporated into an oligonucleotide using dye-labeled phosphoramidites. Two such labels are 5'-Hexachloro-Fluorescein Phosphoramidite (HEX), and 5'-Tetrachloro-Fluorescein Phosphoramidite (TET), both available from Glen Research.

5.4. Phenotype Selection to Optimize the VGID$^{SM}$ Method

Figure 3:
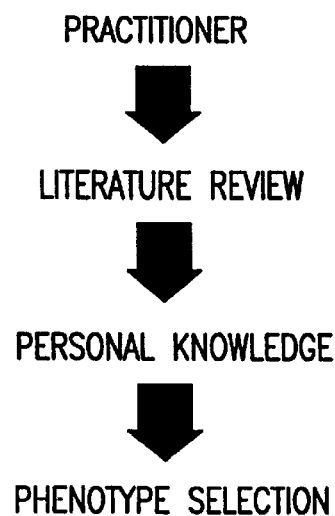
FIG. 3 is a flow chart representation of the phenotype selection process to be employed prior to using the VGID[SM] method of the invention.

Best results are obtained with the VGID$^{SM}$ method when phenotype selection is first given careful consideration by the practitioner (see FIG. 3). What follows is a preferred, but not limiting, phenotype selection method.

The phenotype selection process generally begins with a literature review. This involves reviewing biological literature, medical literature, chemical literature, published bioassays and clinical data in connection with a phenotype-of-interest and with any phenotypes to be compared with (i.e. subtracted from) the phenotype-of-interest.

In this regard, reference to the most current edition of a catalog of known genetic disease may be made to initiate the literature review. For example, one catalog of human phenotypes is McKusick, Victor A., Mendelian Inheritance in Man, Catalog of Autosomal Dominant, Autosomal Recessive, and X-Linked Phenotypes (10th Edition, 1992, The Johns Hopkins University Press, Baltimore, Md.) (hereinafter "MIM™"). MIM™ is also available in a continuously-updated, online version (hereinafter "OMIM™"), which may be accessed at no charge by contacting OMIM™ User Support, Welch Memorial Library, 1830 East Monument Street, Third Floor, Baltimore, Md. 21205, or via e-mail to omimhelp@welch.jhu.edu. In general, MIM™ and OMIM™ comprise a catalog with one entry per human gene locus, whether or not the gene has been associated with any particular disease. Each entry, usually one or two paragraphs, provides information having the following components (when the information is available): (a) title, including any synonyms in parentheses; (b) a description of the phenotype or gene product; (c) the nature of the basic defect in any associated disorder; (d) a description of diagnosis and management of the disorder, where applicable; (e) genetics, including mapping information; (f) allelic variants; and (g) references. Finding aids in MIM™ include an author index and a title index. The content of OMIM™, in addition to being the most current data available in these catalogs, is fully computer searchable. There were nearly 6,000 entries in the Tenth Edition of MIM™ (1992). Therefore, if one makes the usual assumption that perhaps 100,000 human genes exist, this catalog is only 6% complete. Accordingly, the vast majority of genes identified using the VGID™ method will not be represented. Nevertheless, existing entries may comprise related phenotypes and/or references which provide insight into the genetic nature of the phenotype-of-interest.

Other useful information sources include computer-indexed journal collections such as Medline®. For disease phenotypes, internal medicine handbooks may also be consulted (see Isselbacher et al., eds., Harrison's Principles of Internal Medicine, 13th Edition, McGraw-Hill, Inc., New York). The practitioner skilled in the relevant art generally knows which literature sources to review.

Of course, it is not required that a phenotype be recognized in the literature as having a genetic component in order for the VGID$^{SM}$ method to identify genes associated with the phenotype. Indeed, it may even be the absence of such a published recognition or understanding which leads the practitioner to ask what genes are identified using the VGID™ method. In this regard, the practitioner's personal knowledge or belief is an important factor to be considered in phenotype selection. A given phenotype-of-interest can be quite complex and will often be polygenic (see discussion in Section 2.1 hereinabove). In one embodiment, the VGID$^{SM}$ method may involve one or a combination of the two approaches set forth previously herein. Recall that one approach, schematically set forth in FIG. 1, involves performing the VGID$^{SM}$ method using phenotypic groups defined by sources not known to share a common ancestor (e.g. most cell line samples). The other approach, schematically set forth in FIG. 2, involves performing the VGID$^{SM}$ method using phenotypic groups defined by samples obtained from sources known to share at least one common ancestor (i.e. consanguineous sources).

An overview of the phenotype selection process is set forth in FIG. 3. In this figure, PRACTITIONER represents an individual skilled in the relevant biological art (e.g. geneticist, microbiologist, virologist, endocrinologist, plant molecular biologist, pathologist, physiologist, surgeon, post-doctoral fellow, graduate student, research technician); LITERATURE SEARCH represents a review of the relevant literature performed by the practitioner; PERSONAL KNOWLEDGE represents the knowledge, understanding and belief in the relevant biological art provided by the practitioner; and PHENOTYPE SELECTION represents the identification of the appropriate biological samples by the practitioner after having considered the literature search and the practitioner's personal knowledge.

5.4.1. Tissue Sample Collection

Tissue samples are typically collected using methods well known to those of skill in the relevant art. For example, to identify genes involved in colon cancer, the gastroenterologist or endoscopist may collect healthy and diseased biopsy samples using an endoscope. Common sense is the guiding principle here. The VGID$^{SM}$ method will provide best results where normal and diseased samples are systematically and thoroughly defined using objective criteria.

5.4.2. Cell Culture

When using the VGID$^{SM}$ method with cell lines as input phenotypes, utmost care is advised. The specific conditions used for culturing will profoundly influence gene expression in virtually all cell lines. For example, the steroid hormone aldosterone influences the expression of genes important for salt absorption by epithelia, such as the A6 cell line derived from *Xenopus laevis*. The concentration of hormones and growth factors may vary over a broad range in media supplements commonly used (e.g. fetal calf serum or newborn calf serum). Therefore, careful attention should be paid to the control of such variables. If problems arise, consideration should be given to the reservation of specific lots for all ingredients used. Further, chemical analyses of specific components may also be required as part of the standardization process. This concern over control of growth conditions is not limited to hormones and growth factors. Gene expression may be influenced by such basic parameters as length of time between passage, incubation temperature, pH, and the like.

Accordingly, gene identification with the VGID$^{SM}$ method using cell lines as input sources will be optimized and enhanced by careful attention to defining, and maintaining constant, the cell culture conditions associated with the phenotype-of-interest. This is equally true for the phenotype or phenotypes to be compared (i.e. subtracted). The culture of animal cells has been well described by numerous references in the literature. The literature search conducted in choosing input phenotypes should be focused, in part, on defining the optimum cell culture conditions. For a broad overview of cell culture techniques and other relevant considerations, see Freshney, R. I., 1994, Culture of Animal Cells, A Manual of Basic Technique, 3d Edition, John Wiley & Sons, Inc., New York, N.Y.

5.5. Troubleshooting the VGID$^{SM}$ Method

If a given phenotype-of-interest is initially resistant to the above-described approaches for using the VGID$^{SM}$ method to identify a gene-of-interest, the following troubleshooting discussion may be helpful. A resistant phenotype-of-interest may be indicated by the identification of no genes, or the identification of too many genes (e.g. over 100), in the appropriate pool under the experimental design chosen. Consider a case where an initial screen does not identify a genetic component associated with a given phenotype-of-interest. In this instance, careful attention should be paid to redefining the nucleic acid populations defined by the input phenotypes. For example, a synergistic effect between one or more genes and an environmental factor may be required for manifestation of the phenotype-of-interest. In this instance, it is desirable to identify and control any environmental factor present. In this way, a weak genetic determinant for a given phenotype-of-interest may be strengthened by careful modification of the criteria for inclusion in a phenotypic group.

A variety of biological assays may also be used to further define a phenotypic group. Examples of such assays are set forth in the Section immediately below.

5.6. Assays for Phenotype Selection

Enzymatic and receptor-based biological assays may be used to further define a phenotype which is initially resistant to gene identification with the VGID™ method. Such definition is directed toward exclusion of individuals from a population which may not contribute to the genotype and which, therefore, would be beneficial to exclude from the gene identification assay. The eventual therapeutic use(s) resulting from the gene identification may serve as a guide to selection of relevant biological assays known in the art. For example, the bioassays selected for further definition of the phenotype of schizophrenia might involve a panel of central nervous system receptors implicated in that disease. There are many sources available which describe enzymatic or receptor assays. One example is the Methods in *Enzymology* series published by Academic Press. One skilled in the art would know what assays are most appropriate for defining the input phenotype.

For example, for using the VGID™ method on a neurological disorder with a genetic component, relevant bioassays might include assays for activity of adrenergic receptors, cholinergic receptors, dopamine receptors, GABA receptors, glutamate receptors, monoamine oxidase, nitric oxide synthetase, opiate receptors, or serotonin receptors. For cardiovascular disorders, appropriate assays may include adenosine $A_1$ receptors, adrenergic receptors (including $\alpha_1$, $\alpha_2$, $\beta_1$), angiotensin I inhibition, platelet aggregation, ion channel blockade (e.g. calcium channels, chloride channels), cardiac arrhythmia measurement, blood pressure, heart rate, contractility or hypoxia. For a metabolic disorder the following bioassays may be used: serum cholesterol, serum HDL, serum HDL/cholesterol ratio, HDL/LDL ratios, serum glucose, kaluresis, saluresis, or urine volume change. For an allergic or inflammation disorder the following bioassays may be used: Arthur's reaction, passive cutaneous anaphylaxis, bradykinin $B_2$, tracheal contractility, histamine $H_1$ antagonism, carrageenan affects on macrophage migration, leukotriene $D_4$ antagonism, neurokinin $NK_1$ antagonism, or cytokine assays (e.g. the interleukins or macrophage inhibitory proteins). For gastrointestinal disorders the following bioassays may be used: cholecystokinin $CCK_A$ antagonism, cholinergic antagonism, gastric acidity, or serotonin 5-$HT_3$ antagonism. The above listings merely provide exemplary assays. One skilled in the art would be able to choose a relevant bioassay or collection of bioassays for use in defining a phenotype.

5.7. Diseases, Disorders, and Other Phenotypes

The various phenotypes for which genes may be identified using the VGID™ method include, but are not limited to, any of the following disorders, diseases and phenotypes. Examples of disease states include the following: acquired immunodeficiency syndrome (AIDS), angina, arteriosclerosis, arthritis, asthma, high or low blood pressure, bronchitis, cancer, cholesterol imbalance, cerebral circulatory, clotting disorder, disturbance, cirrhosis, depression, dermatologic disease, diabetes, diarrhea, diuresis, dysmenorrhea, dyspepsia, emphysema, gastrointestinal distress, hemorrhoids, hepatitis, hypertension, hyperprolactinemia, immunomodulation, resistance to bacterial infection, resistance to viral infection, inflammation, insomnia, lactation, lipidemia, migraine, pain prevention or management, peripheral vascular disease, platelet aggregation, premenstrual syndrome, prostatic disorder, elevated triglycerides, respiratory tract infection, retinopathy, sinusitis, rheumatic disease, impaired wound healing, tinnitus, urinary tract infection and venous insufficiency.

Other phenotypes include, but are not limited to, cardiovascular disorders, nervous system disorders, enhancing memory, hypercholesterolemia, immune system stimulation, anti-inflammatory, antipyretic, analgesic, slowing the aging process, accelerated convalescence, anemia, indigestion, impotence and menstrual disorders.

Preferred phenotypes include, but are not limited to, plant resistance phenotypes (e.g. resistance to herbicides or insect predators), microorganism resistance phenotypes (e.g. resistance to antibiotics), cancer (e.g. breast, prostate), osteoporosis, obesity, type II diabetes, and prion-related diseases (e.g. bovine spongiform encephalitis, Creutzfeldt-Jakob disease).

5.8. Linking Oligonucleotides to Specific Binding Ligands

The present invention embodies a method for the use of identification tags (i.e. specific binding ligands which are recognized by specific receptors) to facilitate the identification and isolation of sequences of interest from a complex mixture. In order to sort unknown sequences specific to a cell or a given phenotype from a mixture of sequences of different origins, it is important to be able to identify sequences from various sources. One method to label each different source of cDNA with a unique identification tag is accomplished by using labeled PCR oligos.

The PCR oligonucleotide primers utilized to generate the raw material used in the VGID$^{SM}$ assays are labeled with a specific binding ligand. The labeling involves attaching the ligand to the oligonucleotide in a stable manner. In a preferred embodiment, the ligand is attached to the primer via covalent bonding. Methods for attaching the primer to the ligand are well known in the art. Various oligonucleotide labels include biotin, avidin or streptavidin and their derivatives, lectin, carbohydrate, peptide, hapten, or immunological material.

Oligonucleotides may be labeled with a wide variety of labels for use in the various embodiments of the invention. For example, European Patent Publication No. EP 0370 694 A2, entitled, "Diagnostic Kit and Method Using a Solid Phase Capture Means For Detecting Nucleic Acid", by Burdick and Oakes, publication date May 30, 1990, discloses methods of linking labels to oligonucleotides.

In a preferred embodiment, the oligonulceotides are labeled with peptides. Methods of attaching peptides to oligonucleotides are well known to those with ordinary skill in the art, e.g., see, 1) Preparation and characterization of antisense oligonucleotide-peptide hybrids containing viral fusion peptides. Soukchareun et al., 1995, Bioconjug. Chem. 6(1), 43–53; 2) Preparation of oligonucleotide-peptide conjugates. Tung, et al., 1991, Bioconjug. Chem. 2(6), 464–465; 3) Template-directed ligation of peptides to oligonucleotides. Bruick et al., 1996, Chem. Biol. 3(1), 49–56; 4) Dual-specificity interaction of HIV-1 TAR RNA with Tat peptide-oligonucleotide conjugates. Tung et al., 1995, Bioconjug. Chem. 6(3), 292–295; 5) Synthesis and Enzymatic Stability of Phosphodiester-Linked Peptide-Olignonucleotide Hybrids. Robles et al., 1997, Bioconjug. Chem. 8(6), 785–788; and 6) Covalent Protein-oligonucleotide Conjugates for Efficient Delivery of Antisense Molecules. Rajur et al., 1997, Bioconjug. Chem. 8(6), 935–940.

Oligonucleotides linked to various peptides for use in the methods of this invention may be obtained for example, from Cybergene S. A. (11 rue Claude Bernard, z1 nord, 35400, Saint Mallo, France) and Glen Research (22825 Davis Drive, Sterling, Va. 20164). Further information from Glen Research can be obtained through their web site (www.glenres.com).

One specific method for linking a peptide to an oligonucleotide recommended by Glen Research is as follows (see also, www.glenres.com). A heterobifunctional crosslinking reagent is used to link a synthetic peptide having an N-terminal lysine residue to a 5'-thiol-modified oligonucleotide. Such a crosslinking reagent is N-maleimido-6-aminocaproyl-(2'-nitro, 4'-sulfonic acid) phenyl ester (mal-sac-HNSA). The sodium salt of mal-sac-HNSA is available from Bachem Bioscience. Conveniently, reaction of the mal-sac-HNSA crosslinker with an amino group releases a dianion phenolate (i.e. 1-hydroxy-2-nitro-4-benzene sulfonic acid). This dianion phenolate is also a yellow chromophore. The chromophore feature provides (i) a means for quantifying the extent of completion of the coupling reaction (where greater yellow color intensity corresponds to a more complete coupling reaction), and (ii) an aid in monitoring the extent of separation of an activated peptide (i.e. a peptide crosslinked to mal-sac-HNSA and ready for contacting with a 5'-thiol-modified oligonucleotide) from free crosslinking reagent during gel filtration.

The specific steps employed when using a mal-sac-HNSA crosslinker may be as follows. First, a peptide is synthesized having an N-terminal lysine. Alternatively, a peptide having an internal lysine may be used since the lysine epsilon amino group is actually more reactive than the lysine alpha amino group. Second, an oligonucleotide is synthesized having a 5'-thiol group using methods known in the art. Third, the peptide is reacted with an excess of mal-sac-HNSA in a sodium phosphate buffer (pH 7.1). Fourth, the peptide-mal-sac conjugate is separated from free crosslinker and the buffer is exchanged to sodium phosphate (pH 6) using a gel filtration column (e.g. NAP-5, Pharmacia, Uppsala, Sweden). Fifth, a thiol-modified oligonucleotide is activated, desalted and buffer-exchanged to sodium phosphate (pH 6) on a gel filtration column. Sixth, the activated peptide is reacted with the thiol-modified oligonucleotide. Finally, the peptide-oligonucleotide conjugate is purified by ion exchange chromatography (e.g. Nucleogen DEAE-500-10 or equivalent). The elution order from the ion exchange column is as follows: free peptide first, peptide-labeled oligonucleotide next, and free oligonucleotide last.

In a preferred embodiment, the peptide labeled oligonucleotides are recognized by specific receptors, such as antibodies, to sort and isolate particular nucleic acids from a complex mixture. Given that a peptide-labeled oligonucleotide primer may be subjected to high temperatures during PCR, in a preferred embodiment, the peptide is sufficiently short (i.e. no more than five amino acids) to resist irreversible denaturation. In addition, the peptides can be made resistant to different classes of proteases by avoiding the inclusion of protease-sensitive peptide links such as those that involve serine and/or threonine. A number of procedures have been used to add a single primary aliphatic amino group to oligonucleotides. See e.g. Agrawal et al., 1986, Nucleic Acids Res. 14, 6227–6245; Chollet et al., 1985, Nucleic Acids Res. 13, 1529–1541; Wachter et al., 1986, Nucleic Acids Res. 14, 7985–7994; Sproat et al., 1987, Nucleic Acids Res. 15, 6181–6196; Li et al., 1987, Nucleic Acids Res. 15, 5275–5286; and Smith et al., 1985, Nucleic Acids Res. 13, 2439–2502. Various methods may be used to synthesize oligonucleotides containing multiple amino groups attached to the oligonucleotide through a linker arm. Haralambidis et al., 1990, Nucleic Acids Res. 18, 493–499; Haralambidis et al., 1987, Nucleic Acids Res. 15, 4857–4876; Ruth et al., 1985, DNA 4, 93; Ruth, 1984, DNA 3, 123; Draper, 1984, Nucleic Acids Res. 12, 989–1002. Attachment of a ligand such as biotin to the oligonucleotide is described in Kempe et al., 1985, Nucleic Acids Res. 13, 45–57. The use of an alkylating intercalation moiety as an attachment is described in U.S. Pat. No. 4,582,789. Other standard peptide coupling methods and derivatized oligonucleotide methods can also be used (see e.g. EPA 0 370 694).

These standard procedures from the above references are incorporated herein by reference in their entireties.

5.9. Antibodies and Derivatives Thereof

In a preferred embodiment antibodies may be used to specifically recognize one or more peptide-labeled oligonucleotides used to label a plurality of nucleic acid populations (e.g. cDNA libraries). Such antibodies include but are not limited to polyclonal, monoclonal, humanized or chimeric antibodies, single chain antibodies, Fab fragments and F(ab')$_2$ fragments, fragments produced by a Fab expression library, anti-idiotypic (anti-Id) antibodies, and epitope-binding fragments of any of the above. Such antibodies may be used as ligands in one of the screening steps in the present invention.

Polyclonal antibodies which may be used in the methods of the invention are heterogeneous populations of antibody molecules derived from the sera of immunized animals. Various procedures well known in the art may be used for the production of polyclonal antibodies to an antigen-of-interest. For example, the production of polyclonal antibodies, various host animals can be immunized by injection with an antigen of interest or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies which may be used in the methods of the invention are homogeneous populations of antibodies to a particular antigen. A monoclonal antibody (mAb) to an antigen-of-interest can be prepared by using any technique known in the art which provides for the production of antibody molecules by continuous cell lines in culture. These include but are not limited to the hybridoma technique originally described by Kohler and Milstein, 1975, Nature 256, 495–497, and the more recent human B cell hybridoma technique (Kozbor et al., 1983, Immunology Today 4, 72), and the EBV-hybridoma technique (Cole et al., 1985, Monoclonal Antibodies and Cancer Therapy, Alan R. Liss, Inc., pp. 77–96). Such antibodies may be of any immunoglobulin class including IgG, IgM, IgE, IgA, IgD and any subclass thereof. The hybridoma producing the mAbs of use in this invention may be cultivated in vitro or in vivo.

The monoclonal antibodies which may be used in the methods of the invention include but are not limited to human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80, 7308–7312; Kozbor et al., 1983, Immunology Today 4, 72–79; Olsson et al., 1982, Meth. Enzymol. 92, 3–16).

Further, humanized monoclonal antibodies may be used. Briefly, humanized antibodies are antibody molecules from non-human species having one or more complementarily determining regions (CDRs) from the non-human species and a framework region from a human immunoglobulin molecule. Various techniques have been developed for the production of humanized antibodies (see e.g., Queen, U.S. Pat. No. 5,585,089, which is incorporated herein by reference in its entirety). An immunoglobulin light or heavy chain variable region consists of a "framework" region interrupted by three hypervariable regions, referred to as complementarily determining regions (CDRs). The extent of the framework region and CDRs have been precisely defined (see, Kabat et al., 1983, "Sequences of Proteins of Immunological Interest", U.S. Department of Health and Human Services).

A chimeric antibody is a molecule in which different portions are derived from different animal species, such as those having a variable region derived from a murine mAb and a human immunoglobulin constant region. Techniques have been developed for the production of "chimeric antibodies" (Morrison et al., 1984, Proc. Natl. Acad. Sci. U.S.A. 81, 6851–6855; Neuberger et al., 1984, Nature, 312, 604–608; Takeda et al., 1985, Nature, 314, 452–454) by splicing the genes from a mouse antibody molecule of appropriate antigen specificity together with genes from a human antibody molecule of appropriate biological activity.

Alternatively, techniques described for the production of single chain antibodies (U.S. Pat. No. 4,946,778; Bird, 1988, Science 242, 423–426; Huston et al., 1988, Proc. Natl. Acad. Sci. USA 85, 5879–5883; and Ward et al., 1989, Nature 334, 544–546) can be adapted to produce single chain antibodies against the peptide portion of the peptide-labeled oligonucleotide nucleotides useful in the methods of the invention. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246, 1275–1281) to allow rapid and easy identification of monoclonal Fab fragments with the desired specificity.

Antibodies to the peptide portion of a peptide-labeled oligonucleotide can, in turn, be utilized to generate anti-idiotype antibodies that "mimic" the peptide, using techniques well known to those skilled in the art. (See, e.g., Greenspan & Bona, 1993, FASEB J 7(5), 437–444; and Nissinoff, 1991, J. Immunol. 147(8), 2429–2438). For example, antibodies which bind to the peptide and competitively inhibit the binding of peptide to its receptor can be used to generate anti-idiotypes that "mimic" the peptide receptor and, therefore, bind the peptide.

A molecular clone of an antibody to an antigen-of-interest can be prepared by many well known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by many well known techniques, e.g., immunoabsorption or immunoaffinity chromatography, chromatographic methods such as HPLC (high performance liquid chromatography), or a combination thereof, etc.

The methods of antibody production and use employed herein can, for example, be such as those described in Harlow and Lane (Harlow, E. and Lane, D., 1988, Antibodies: A Laboratory Manual, Cold Spring Harbor Laboratory Press, Cold Spring Harbor, N.Y.), which is incorporated herein by reference in its entirety.

The single-letter amino acid codes which correspond to the three-letter amino acid codes of the Sequence Listing are set forth hereinbelow: A, Ala; R, Arg; N, Asn; D, Asp; B, Asx; C, Cys; Q, Gln; E, Glu; Z, Glx; G, Gly; H, His; I, Ile; L, Leu; K, Lys; M, Met; F, Phe; P, Pro; S, Ser; T, Thr; W, Trp; Y, Tyr; and V, Val.

Suitable antibodies for use with the methods of this invention include the following, available from Affinity Bioreagents, Inc., 79, rue des Morillons, 75015, Paris, France.

1) Catalog No. PA 1-047 (affinity-purified rabbit IgG). The corresponding peptide recognized by this antibody is KFSREKKAAKT (SEQ ID NO:71).

2) Catalog No. PA 1-039 (affinity-purified rabbit immunogobins). The corresponding peptide recognized by this antibody is DQKRYHEDIFG (SEQ ID NO:72).

3) Catalog No. PA 1-036 (purified rabbit IgG). The corresponding peptide recognized by the antibody is DLKEEKDINNNVKKT (SEQ ID NO:73).

4) Catalog No. PA 1-014 (purified rabbit antibody). The corresponding peptide recognized by this antibody is CTGEEDTSE (SEQ ID NO: 74).

5) Catalog No. PA 3-013 (affinity purified IgG). The corresponding peptide recognized by this antibody is PEETQTQDQPM (SEQ ID NO:75).

6) Catalog No. PA 1-815 (rabbit anti-serum). The corresponding peptide recognized by this antibody is QKSDQGVEGPGAT (SEQ ID NO:76).

7) Catalog No. PA 3-034 (rabbit polyclonal serum IgG). The corresponding peptide recognized by this antibody is DIGQSIKKFSKV (SEQ ID NO:77). This polyclonal antibody will also recognize QRADSLSSHL (SEQ ID No:78).

In addition, antibodies for use with the methods of this invention may be obtained from Medical & Biological Laboratories Co., Ltd., 440 Arsenal Street, Watertown, Mass. 02171, U.S.A.

These include the following:

1) Code No. 561 (Rabbit IgG from anti-serum). The corresponding peptide recognized by this antibody is YPYDVPDYA (SEQ ID NO:79).

2) Code No. 562 (Rabbit IgG from anti-serum). The corresponding peptide recognized by this antibody is EQKLISEEDL (SEQ ID NO:80).

3) Code No. 563 (Rabbit IgG from anti-serum). The corresponding peptide recognized by this antibody is YTDIEMNKLGK (SEQ ID NO:81).

5.10. Antibody Columns for Sorting Nucleic Acids

An antibody specific to a given peptide label which is used to identify nucleic acids arising from different sources may be bound to a solid phase support or carrier material to facilitate separation using various techniques well known in the art.

Here, the "solid phase support or carrier" can be any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble or insoluble for the purposes of the present invention. The solid phase support or carrier material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

For example, the solid phase support or carrier material can be beads, polymeric particles, or other materials, so long as the coupled molecule is capable of binding to an antigen or antibody. Such solid phase supports are readily apparent to one of ordinary skill in the art. Particularly useful solid phase support or carrier materials are polymeric beads having an average particle size of from 0.1 to 10 µmeters.

Antibodies against specific peptides can be bound to any of the above described solid phase support or carrier material in different ways. Two of the most preferred attachments are adsorption and covalent attachment.

The methods for making and using the antibody columns employed herein can, for example, be such as those described in Harlow and Lane (Harlow and Lane, 1988, Antibodies: A Laboratory Manual, Cold Spring Harbor Laboratory Press, Cold Spring Harbor, N.Y.), which is incorporated herein by reference in its entirety.

Further, examples of suitable antibodies and peptide labels may be found, for example, in U.S. application Ser. No. 09/174,328, entitled "METHODS FOR MANIPULATING COMPLEX NUCLEIC ACID POPULATIONS USING PEPTIDE-LABELED OLIGONUCLEOTIDES", by Iris and Pourny (Attorney Docket No. 9408-025), filed Oct. 16, 1998, which is incorporated by reference herein in its entirety.

5.11. Detection of Antibodies Against Peptide-labeled Oligonucleotides

Antibodies which recognizes peptide-labeled oligonucleotides may also be detectably labeled using any method known to one skilled in the art. Many such methods are known. For example, one of the ways in which an anti-peptide antibody can be detectably labeled is by linking the same to an enzyme and use in an enzyme immunoassay (EIA), "The Enzyme Linked Immunosorbent Assay (ELISA)" Voller, 1978, Diagnostic Horizons 2, 1–7; Voller et al., 1978, J. Clin. Pathol. 31, 507–520; Butler, 1981, Meth. Enzymol. 73, 482–523; Maggio, 1980, Enzyme Immunoassay, CRC Press, Boca Raton, Fla.; Ishikawa et al., 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect peptide portion of the peptide-labeled oligonucleotide through the use of a radioimmunoassay (RIA) (see, for example, Weintraub, 1986, Principles of Radioimmunoassays, Seventh Training Course on Radioligand Assay Techniques, The Endocrine Society, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are green fluorescent protein, luciferin, luciferase and aequorin.

6. EXAMPLE: USE OF THE VGID$^{SM}$ METHOD TO IDENTIFY hDinP GENES

6.1. Introduction

Two human DinP (hDinP) genes have been identified using the VGID$^{SM}$ method applied to cell line sources, as described hereinbelow. The VGID$^{SM}$ approach employed was that described hereinabove for cell line samples (see FIG. 1). The aim of this example was to isolate any human homologue(s) of the bacterial DinP gene. In bacteria and yeast, the product of the DinP gene (i.e. DinP) is central to the inducible DNA damage repair pathway known as the "SOS repair system." Although this DNA repair pathway is known to exist in man, inducibility has never been demonstrated. The components of this pathway are known to be directly involved in the appearance of secondary cancers following radiation therapy or chemotherapy in humans. Nevertheless, the human genes encoding the components of the pathway have not been previously identified. The VGID$^{SM}$ example described below isolated, in less than three weeks, a total of five independent human cDNA clones. The clones were analyzed by DNA sequencing, translation into all six reading frames, and protein database search (BLASTX). Translations of all five clones displayed high amino acid sequence homology to the bacterial DinP protein, thereby confirming the identification of human homologues of bacterial DinP. It should be well noted that low stringency hybridization of a bacterial DinP probe to a human library would not have identified these clones since the nucleic acid sequence homology is too low to permit this type of screen.

6.2. Materials and Methods

Cell lines (phenotype selection). For isolation of hDinP transcripts by MutS-mediated selective subtraction, two input cell lines differing in their capacity to effect DNA repair were utilized. The phenotype-of-interest (i.e. human DinP activity) was provided by presumed "high expresser" cells from a defined lymphoblastoid clonal line (lymphoblasts) (i.e. cell line #1 in FIG. 1). These cells were harvested at a time corresponding to the apex of their in vitro growth curve (i.e. 84 hours after initiation of the growth phase). The competitor-cDNA providers (i.e. cell line #2 in FIG. 1) were hepatocytes grown in standard medium for 60 hours before harvesting. These two cell lines originated from different sources and therefore have a very low probability of consanguinity (i.e. of having a common ancestor). However, the fast growth rate of these cell lines is associated with the possibility of substantial levels of mutation acquisition.

mRNA extraction and cDNA synthesis. These procedures were performed using Gibco-BRL "Trizol" kits (mRNA preparation) and Promega "Universal Riboclone" kits (cDNA synthesis) according to manufacturers' protocols. Synthesized cDNA was size-fractionated by electrophoresis in an agarose gel (0.8%); fragments ranging from 300 to 600 base pairs were excised from the gel. The cDNA was extracted from the gel slices using Promega Gel-Clean kits according to the manufacturer's protocol.

cDNA libraries. A library for each cell line was constructed by blunt-end ligation of the size-selected cDNA into the QuanTox™ Blunt (Quantum Biotechnologies) plasmid vector. Ligation products were transformed into DH5α competent E. coli cells. These cells were grown overnight in ampicillin-containing liquid medium. Cells were next harvested and the insert-containing plasmid vectors were recovered using Qiagen plasmid purification kits.

Amplification of cDNA inserts. The inserts present in the cDNA library obtained from the lymphoblasts were PCR amplified using oligonucleotide primers specific to the vector's cloning-cassette. The polymerase enzymes used were Pfu DNA polymerase (1.5 U/100 μl reaction) and the Stoffel fragment of DNA polymerase I (0.5 U/100 μl reaction). The cycling protocol used was: 97° C., 3 min; 58° C., 5 sec; 70° C., 1 min; then 93° C., 30 sec; 58° C., 5 sec; 70° C., 1 min for 15 cycles. PCR products were purified over Qiagen columns. The purified PCR products were heat-denatured at 98° C. for 5 min, incubated at 65° C. for 20 min and cooled to room-temperature.

The renatured and cooled PCR products (350 ng in 90 μl) were equilibrated in an equal volume of "2×reaction buffer" (40 mM Tris-HCl, pH 7.6; 0.02 mM EDTA; 10 mM MgCl$_2$; 0.2 mM DTT) and exposed for 35 min to MutS adsorbed onto glass beads packed into a 0.5 ml Eppendorf tube perforated by a small hole at the bottom of the tube. During the incubation phase, the Eppendorf tubes were placed in a horizontal position to increase the contact surface area between the beads and reannealed cDNA. The unbound reannealed PCR products left free in solution were recovered in the supernatant following centrifugation to pellet the beads (8000×g; 30 sec). This MutS-mediated trapping step was repeated twice more with fresh beads; the supernatant recovered at the end of this operation and stored at 4° C. until used. This supernatant contains only the transcripts structurally identical among all lymphoblasts in the phenotype-of-interest cell line.

The procedure followed for isolation of transcripts structurally common to all hepatocytes was identical to that described above, except that the primers used for the PCR amplification (corresponding to vector sequences encoding T3 and T7 promoters) were biotinylated at the 5' end. The final supernatant was also stored at 4° C. until used.

Isolation of cDNA encoding hDinP. An aliquot of the stored supernatant from hepatocytes was then mixed with an aliquot of the stored supernatant from lymphoblasts in a 3:1 ratio (hepatocyte:lymphoblast). This mixture was denatured, reannealed, and exposed to MutS-coated beads, as above, to remove all mismatched heteroduplexes.

The supernatant from this mixture was next exposed to streptavidin-coated beads (Dynabeads M-180, Dynal, used according to the manufacturer's protocol) in order to trap all non-mismatched homoduplex hybrids formed from one hepatocyte strand and one lymphoblast strand (i.e. transcripts structurally identical in hepatocytes and lymphoblasts), as well as all remaining hepatocyte-specific transcripts. This trapping step was performed by incubating the supernatant recovered after the MutS binding reaction (150 µl) with 150 µl of dry streptavidin beads.

Following recovery of the streptavidin bead supernatant, the beads were rinsed twice in 1×reaction buffer to recover all unbound material. The washings were recovered by centrifugation, pooled with the streptavidin bead supernatant, and saved at 4° C. The pooled streptavidin bead supernatant, theoretically containing only lymphoblast-specific transcripts structurally identical in all lymphoblast cells, was then desalted and concentrated using Qiaex II DNA purification kits (Qiagen) as per the manufacturer's protocol.

The purified material was blunt-ended by 3' extension (DNA tailing kit, Boehringer-Mannheim), purified over Quiagen columns as above, and cloned into the QuanTox™ Blunt vector as previously described. The twelve recombinant colonies obtained were then individually tested for the presence of inserts by: (i) PCR amplification; and (ii) hybridization at various stringencies with a PCR-generated, labeled fragment of the *E. coli* DinP gene. Under low stringency hybridization conditions (i.e. 40° C. overnight in 3×SSC, 1×Denhardt's solution, 20 mM sodium phosphate (pH 6.5), 10% dextran sulfate, 100 µg/ml salmon sperm DNA; 3 washes in 3×SSC and 1% SDS at 40° C. for 15 min each), signals from all twelve clones were obtained, but the signals were slightly stronger for the five clones later identified by sequencing and computer analysis to be derived from two hDinP genes (see below). By contrast, under medium stringency hybridization conditions (i.e. 50° C. overnight in same buffer used for low stringency plus 25% deionized formamide; 3 washes in 2×SSC and 1% SDS at 50° C. for 15 min each), weak signals from all twelve clones were obtained without apparent differences in signal intensities. Finally, under high stringency hybridization conditions (i.e. 60° C. overnight in the same buffer used for medium stringency conditions; 3 washes in 1×SSC and 1% SDS at 60° C. for 15 min each), a complete absence of signal from all twelve clones resulted. These hybridization results suggest that at least five of the twelve clones isolated contain inserts. The results further suggest that one would not isolate any hDinP clones by simply screening a human library directly with a labeled fragment of the *E. coli* DinP gene; the hybridization signal in such a library screen would be indistinguishable from background.

Of the twelve clones isolated by the method of the invention, five were sequenced which displayed the slightly stronger signal under high stringency conditions relative to the other seven. These five clones were next used as query sequences in individual BLASTX protein database searches after translation into all six reading frames (FIGS. 5–9). The single-letter amino acid codes appearing in the computer analyses provided by the BLASTX searches (see FIGS. 5–9) which correspond to the three-letter amino acid codes of the Sequence Listing are set forth in Section 5.9 Supra.

6.3. Results

This VGID[SM] example isolated a total of five overlapping human cDNA inserts (see FIG. 4 for a map of overlapping regions) which appear in the Sequence Listing as SEQ ID NOs:1–5. BLASTX protein database search and a computer analysis was performed on each of the five identified sequences after translation into all six reading frames (see FIGS. 5–9 for BLASTX results). The results revealed high amino acid sequence homology exclusively with the bacterial DinP protein and it's close relatives such as UV protection protein mucB (see FIG. 5A). On the basis of overlapping sequences, these five inserts were assigned to two separate, homologous hDinP genes, as described below.

Three of the five overlapping inserts (SEQ ID NOs:1–3) cover about half of the predicted length for a full-length hDinP transcript after assembly into a composite sequence (SEQ ID NO:6). The other two inserts (SEQ ID NOs:4–5), which correspond to a cumulative length of 386 bases, also overlap with each other and with the composite sequence of SEQ ID NO:6. However, these two inserts provide evidence for the existence of two hDinP genes, as further described below. This result is in agreement with other characterized human DNA repair genes, which are all known to be encoded by multiple genes. That SEQ ID NOs:4–5 represent transcripts derived from different genes encoding isoforms of hDinP is suggested by limited internal sequence divergence at positions 237–252 and 274–279.

6.4. Discussion

The two novel hDinP genes identified above represent a significant advance in our understanding of human genes involved in DNA repair. Moreover, the new genes will be useful in the development of various prognostic tests, diagnostic tests, and therapeutic interventions for treatment of disease, especially cancer. This is true, in part, because DNA repair pathways have been so strongly connected to cancer-causing mechanisms (see e.g. Fishel et al., 1993, Cell 75(5), 1027–1038).

The protein sequences encoded by the five human clones and their corresponding bacterial relatives are set forth in SEQ ID NOs:7–70. The search analyses for the five clones listed in SEQ ID NOs:1–5 are set forth in FIGS. 5–9, respectively. It is noteworthy that all five independent clones encode a protein homologous to *E. coli* DinP; i.e. mainly hDinP clones (five of twelve) were identified by the VGID[SM] method in this experiment. This result dramatically demonstrates the high specificity for gene identification obtainable with the VGID[SM] method. This specificity is directly correlated with the well defined input phenotypes employed. Protein translation results for SEQ ID NO:1 (# 1) are listed in SEQ ID NOs:7–24. Protein translation results for SEQ ID NO:2 (Tor-M) are listed in SEQ ID NOs:25–29. Protein translation results for SEQ ID NO:3 (# 3) are listed in SEQ ID NOs:30–41. Protein translation results for SEQ ID NO:4 (*1) are listed in SEQ ID NOs:42–58. Protein translation results for SEQ ID NO:5 (*2) are listed in SEQ ID NOs:59–70.

6.5. Application of the VGID[SM] Method to a Complex, Multistage System—Multiplex VGID[SM] (VGGT[SM])

The VGID[SM] method may be applied to complex, multistage systems, such as cancer. In cancer, several stages having different phenotypes can coexist, e.g., within a single biopsy specimen, or within primary cell cultures propagated therefrom. When applied to such a system, however, the VGID$^{SM}$ method requires performance of a large number of assays (i.e. one unlabeled cDNA library and one biotin-lableled cDNA library for pairwise comparison of each stage with all other stages). Multiplex VGID$^{SM}$, also known as ValiGene Gene Trapping (VGGT$^{SM}$), offers an alternative approach for analysis of complex, multistage systems.

VGGT$^{SM}$ does not require performance of a large number of pairwise comparisons. By contrast, the number of assays performed is considerably reduced, thus saving the user time and money. VGGT$^{SM}$ (Multiplex VGID$^{SM}$) permits the simultaneous analysis of more than two phenotypes (represented by more than two cDNA libraries) by PCR labeling inserts from each library using primers having a unique label. In a preferred embodiment, the unique label is a peptide label. In another preferred embodiment, the unique peptide label is recognized by an antibody specific for the label.

In this way, cDNA fragments derived from each of any number of libraries subjected to a Multiplex VGID$^{SM}$ analysis can be specifically identified and retrieved as desired by the user. Further, such identification and retrieval can be at any point in the Multiplex VGID$^{SM}$ analysis by virtue of the unique library labels. For example, fragments from any number of cDNA libraries can be mixed, denatured, reannealed, and subjected to one or more rounds of MutS chromatography and/or antibody affinity chromatography, all without losing track of the phenotypic source (i.e. cDNA library) from which any particular fragment-of-interest originated.

In a typical Multiplex VGID$^{SM}$ assay, reannealing occurs in the presence of high complexity (i.e. labeled fragments from more than two cDNA libraries are mixed, denatured and reannealed). After reannealing, sorting of the various cDNAs is carried out using MutS chromatography and/or antibody affinity chromatography as desired by the user. The labeling scheme permits the user to isolate any desired cDNA fragment for cloning, probe use, or further sorting as desired.

In summary, peptide-labeled oligonucleotide PCR primers are used for differential labeling of cDNA fragments originating from different libraries. The labels allow one to identify sequences common to more than two libraries and to isolate sequences specific to each library through chromatography. Further, the labels allow one to retrieve cDNA fragments-of-interest from a mixture of nucleic acids of different origins. Overall, the Multiplex VGID$^{SM}$ process allows one to differentially label, sort and isolate expressed nucleotide sequences representing defined phenotypes present in complex mixtures.

6.5.1. Example of a Complex System—Breast Cancer

One example of a complex system which may be subjected to the Multiplex VGID$^{SM}$ method of the invention is breast cancer. In this example, congenic cell lines obtained from the same individual (HBL 100, HH9, MCF-7 and MCF-7 ras) may be used to represent four different cancer stages (i.e. four different phenotypes), as follows:

(a) HBL 100 (pre-cancer stage);

(b) HH9 (pre-metastatic stage, hormone-sensitive);

(c) MCF-7 (metastatic stage, hormone-dependent); and (d) MCF-7 ras (aggressively metastatic stage, hormone-sensitive).

Analysis of this system by VGID$^{SM}$, comparing two phenotypes at a time, would require six different experiments. That is, one would compare (a) with (b), (a) with (c), (a) with (d), (b) with (c), (b) with (d), and (c) with (d). Further, in order to gain knowledge of metabolic pathways that might distinguish each stage, and to identify key elements (such as optimal intervention points) within a pathway-of-interest, cell growth of each cancer stage should be analyzed under different conditions. For example, four suitable conditions may be as follows:

(a) Standard growth conditions (e.g., cell culture medium containing fetal calf serum);

(b) Non-steroid conditions (e.g. serum-free conditions; or serum-containing conditions where the serum has been treated to remove all steroids);

(c) Estradiol conditions (e.g. non-steroid conditions where a defined concentration of estradiol has been added back as the only steroid present); and (d) Estradiol plus tamoxifen conditions (e.g. estradiol conditions where a defined concentration of tamoxifen has also been added).

For a complete analysis of this system using VGID$^{SM}$, where complete is defined as comparing four different phenotypes to each other under four different conditions, one would perform a total of twenty-four VGID$^{SM}$ assays.

6.5.2. Analysis of a Complex System Using Multiplex VGID$^{SM}$

Each pairwise VGID$^{SM}$ assay just described would provide a readout of the expressed genes distinguishing the two samples being analyzed. Twenty-four such pairwise comparisons could then be further compared among themselves. The efficiency of phenotype comparison in this way is thus hindered by the large number of independent VGID$^{SM}$ assays that needs to be performed.

An alternative approach is Multiplex VGID$^{SM}$. In the above example, HBL 100, HH9, MCF-7 and MCF-7 ras would each be labeled with a different peptide label.

It will be understood that, in the Multiplex VGID$^{SM}$ process, the labels serve not only to identify the library-of-origin of a particular cDNA insert, but also to provide a means of specific retrieval. Using this approach in the above example, retrieval of cDNA fragments that characterize each cancer stage relative to the others and relative to the applied environmental conditions (i.e. cell culture growth conditions) would require many fewer assays. For example, four assays may be performed in which cDNA fragments from each of the four cell lines are compared (i.e. mixed, denatured, reannealed, and sorted by chromatography on MutS and/or antibody columns) under each of the four growth conditions set forth above. Thus, a full analysis of the system may be performed in just four assays instead of the twenty-four required under the pairwise analysis approach.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various publications and patents are cited. Their contents are hereby incorporated by reference into the present application in their entireties.

We claim:

1. A method for identifying one or more genes underlying a defined phenotype comprising the following steps in the order stated:

(a) removing mismatched duplex nucleic acid molecules formed from hybridization within each of a plurality of source populations of cDNAs; and (b) retaining mismatched duplex nucleic acid molecules formed from hybridization among the plurality of source populations, the retained molecules in step (b) comprising the one or more genes underlying the defined phenotype that differ among source populations.

2. The method of claim 1, wherein the plurality of source populations comprises at least one normalized cDNA library.

3. The method of claim 1, wherein the plurality of source populations comprises at least one linearized cDNA library.

4. The method of claim 1, wherein the plurality of source populations comprises two or more cDNA libraries each labeled with a distinguishable label and the hybridization in step (b) is carried out using an excess of labeled DNA from one or more source populations.

5. The method of claim 4, wherein the excess of labeled DNA is a three-fold excess.

6. The method of claim 1, wherein each of the source populations is derived from a cell line.

7. A method for identifying one or more genes underlying a defined phenotype displayed by a cell or individual from which a first cDNA library is derived, but not displayed by a cell or individual from which a plurality of additional cDNA libraries is derived, comprising:

(a) hybridizing insert DNA from the first cDNA library with itself;

(b) hybridizing insert DNA from each library of the plurality of additional cDNA libraries with itself;

(c) contacting the DNA hybridized in step (a) with a first immobilized mismatch binding protein;

(d) contacting each separate population of DNAs hybridized in step (b) individually with a second immobilized mismatch binding protein;

(e) separating unbound DNA from bound DNA contacted in step (c);

(f) separating unbound DNA from bound DNA contacted individually in step (d);

(g) labeling each separate population of the unbound DNA separated in step (f) with a distinguishable label capable of binding a partner molecule immobilized on a substrate;

(h) hybridizing DNA separately labeled in step (g) with unbound DNA separated in step (e);

(i) contacting DNA hybridized in step (h) with a third immobilized mismatch binding protein;

(j) separating unbound DNA from bound DNA contacted in step (i);

(k) contacting unbound DNA separated in step (j) with the partner molecule of each distinguishable label; and (l) separating unbound DNA from bound DNA contacted in step (k), which unbound DNA separated in step (l) encodes one or more identified genes underlying the defined phenotype.

8. The method of claim 7, wherein one or more of the cDNA libraries is normalized.

9. The method of claim 7, wherein one or more of the cDNA libraries is linearized.

10. The method of claim 7, wherein labeling is carried out by polymerase chain reaction using a 5'-peptide labeled primer.

11. The method of claim 7, wherein at least one immobilized partner molecule is an antibody.

12. The method of claim 11, wherein the antibody is an anti-peptide antibody.

13. The method of claim 7, wherein the hybridization in step (h) is carried out using an excess of labeled DNA.

14. The method of claim 13, wherein the excess of labeled DNA is a three-fold excess.

15. The method of claim 7, wherein the first, second, or third immobilized mismatch binding protein is MutS.

16. The method of claim 1, wherein the defined phenotype is selected from the group consisting of a plant phenotype, a microorganism phenotype, and a pathologic phenotype.

17. The method of claim 16, wherein the defined phenotype is a pathologic phenotype that is selected from the group consisting of cancer, osteoporosis, obesity, type II diabetes, and a prion-related disease.

18. A method for identifying one or more genes underlying a defined phenotype displayed by a cell or individual from which a first cDNA library is derived, but not displayed by a cell or individual from which a plurality of additional cDNA libraries is derived, comprising:

(a) amplifying insert DNA from the first cDNA library by polymerase chain reaction;

(b) amplifying insert DNA from each of the plurality of additional cDNA libraries by polymerase chain reaction;

(c) hybridizing DNA amplified in step (a) with itself;

(d) hybridizing each separate population of DNA amplified in step (b) with itself;

(e) contacting DNA hybridized in step (c) with immobilized MutS;

(f) contacting each separate population of DNA hybridized in step (d) individually with immobilized MutS;

(g) separating unbound DNA from bound DNA contacted in step (e);

(h) separating unbound DNA from bound DNA contacted in step (f);

(i) labeling unbound DNA separated in step (g) by polymerase chain reaction using unlabeled primers;

(j) labeling each separate population of unbound DNA separated in step (h) by polymerase chain reaction using at least one primer having a distinguishable 5'-peptide-label capable of binding a partner molecule immobilized on a substrate;

(k) hybridizing DNA labeled in step (i) with DNA labeled in step (j);

(l) contacting DNA hybridized in step (k) with immobilized MutS;

(m) separating unbound DNA from bound DNA contacted in step (l);

(n) contacting unbound DNA separated in step (m) with one or more partner molecules capable of binding the distinguishable 5'-peptide-labeled primers; and (o) separating unbound DNA from bound DNA contacted in step (n), which unbound DNA separated in step (o) encodes one or more identified genes underlying the defined phenotype.

19. A method for identifying one or more alleles underlying a defined phenotype displayed by a cell or individual from which a first cDNA library is derived, but not displayed by a cell or individual from which a plurality of additional cDNA libraries is derived, comprising:

(a) hybridizing insert DNA from the first cDNA library with itself;

(b) hybridizing insert DNA from each of the plurality of additional cDNA libraries with itself;

(c) contacting DNA hybridized in step (a) with a first immobilized mismatch binding protein;

(d) contacting each separate population of DNA hybridized in step (b) individually with a second immobilized mismatch binding protein;

(e) separating unbound DNA from bound DNA contacted in step (c);

(f) separating unbound DNA from bound DNA contacted in step (d);

(g) labeling each separate population of unbound DNA separated in step (f) with a distinguishable label capable of binding a partner molecule immobilized on a substrate;

(h) hybridizing DNA labeled in step (g) with unbound DNA separated in step (e);

(i) contacting DNA hybridized in step (h) with a third immobilized mismatch binding protein;

(j) separating unbound DNA from bound DNA contacted in step (i);

(k) releasing bound DNA separated in step (j) from the immobilized mismatch binding protein;

(l) contacting DNA released in step (k) with one or more partner molecules capable of binding the distinguishable labels;

(m) denaturing DNA contacted in step (l); and (n) separating unbound DNA from bound DNA denatured in step (m), which unbound DNA separated in step (n) encodes one or more identified alleles underlying the defined phenotype.

20. The method of claim 18 or claim 19, wherein at least one cDNA library is normalized.

21. The method of claim 18 or claim 19, wherein at least one cDNA library is linearized.

22. The method of claim 19, wherein labeling is carried out by polymerase chain reaction using 5'-peptide labeled primers.

23. The method of claim 19, wherein at least one immobilized partner molecule is an antibody.

24. The method of claim 23, wherein the antibody is an anti-peptide antibody.

25. The method of claim 19, wherein the hybridization in step (h) is carried out using an excess of labeled DNA.

26. The method of claim 19, wherein the excess of labeled DNA is a three-fold excess.

27. The method of claim 19, wherein at least one of the immobilized mismatch binding proteins is MutS.

28. A method for identifying one or more alleles underlying a defined phenotype displayed by a cell or individual from which a first cDNA library is derived, but not displayed by a cell or individual from which a plurality of additional cDNA libraries is derived, comprising:

(a) amplifying insert DNA from the first cDNA library by polymerase chain reaction;

(b) amplifying insert DNA from each of the plurality of additional cDNA libraries by polymerase chain reaction;

(c) hybridizing DNA amplified in step (a) with itself;

(d) hybridizing DNA amplified from each library in step (b) with itself;

(e) contacting DNA hybridized in step (c) with immobilized MutS;

(f) contacting each population of DNA hybridized in step (d) individually with immobilized MutS;

(g) separating unbound DNA from bound DNA contacted in step (e);

(h) separating unbound DNA from bound DNA contacted in step (f);

(i) amplifying unbound DNA separated in step (g) by polymerase chain reaction using unlabeled primers;

(j) amplifying and labeling each population of unbound DNA separated in step (h) by polymerase chain reaction using a distinguishable 5'-peptide-labeled primer;

(k) hybridizing DNA amplified and labeled in step (j) with DNA amplified in step (i);

(l) contacting DNA hybridized in step (k) with immobilized MutS;

(m) separating unbound DNA from bound DNA contacted in step (l);

(n) releasing bound DNA separated in step (m) from immobilized MutS;

(o) contacting DNA released in step (n) with one or more immobilized antibodies specific for each distinguishable 5'-peptide-labeled primer;

(p) denaturing DNA contacted in step (o); and (q) separating unbound DNA from bound DNA denatured in step (p), which unbound DNA separated in step (q) encodes one or more identified alleles underlying the defined phenotype.

29. The method of claim 28, wherein releasing bound DNA from immobilized MutS in step (n) is carried out using ATP or proteinase K.

30. The method of any one of claims 1, 7, 18, 19 and 28, which further comprises using the one or more genes or alleles identified to carry out a prognosis or a diagnosis.

31. The method of claim 30, wherein the one or more genes or alleles identified, or an encoded protein thereof, is a target for drug intervention.

32. The method of claim 1, wherein the plurality of source populations is in the range of three to twelve source populations.

33. The method of claim 1, wherein the plurality of source populations is in the range of three to six source populations.

34. The method of claim 1, wherein the plurality of source populations consists of four source populations.

35. A method for identifying one or more genes underlying a defined phenotype displayed by a cell or individual from which a first cDNA library is derived, but not displayed by a cell or individual from which a plurality of additional cDNA libraries is derived, comprising:

(a) hybridizing insert DNA from each cDNA library with itself;

(b) contacting each separate population of DNA hybridized in step (a) individually with a first immobilized mismatch binding protein;

(c) separating unbound DNA from bound DNA contacted individually in step (b);

(d) labeling each separate population of unbound DNA separated in step (c) with a distinguishable label capable of binding a partner molecule immobilized on a substrate;

(e) hybridizing DNA separately labeled in step (d);

(f) contacting DNA hybridized in step (e) with a second immobilized mismatch binding protein; and (g) separating unbound DNA from bound DNA contacted in step (f), which bound DNA separated in step (g) encodes one or more identified genes underlying the defined phenotype.

36. A method for identifying one or more genes underlying a defined phenotype displayed by a cell or individual from which a first cDNA library is derived, but not displayed by a cell or individual from which a plurality of additional cDNA libraries is derived, comprising:

(a) amplifying insert DNA from each cDNA library by polymerase chain reaction;

(b) hybridizing each separate population of DNA amplified in step (a) with itself;

(c) contacting each separate population of DNA hybridized in step (b) individually with immobilized MutS;

(d) separating unbound DNA from bound DNA contacted in step (c);

(e) labeling each separate population of unbound DNA separated in step (d) by polymerase chain reaction using at least one primer having a distinguishable 5'-peptide-label capable of binding a partner molecule immobilized on a substrate;

(f) hybridizing DNA labeled in step (e);

(g) contacting DNA hybridized in step (f) with immobilized MutS; and (h) separating unbound DNA from bound DNA contacted in step (g), which bound DNA separated in step (h) encodes one or more identified genes underlying the defined phenotype.

37. A method for identifying one or more alleles underlying a defined phenotype displayed by a cell or individual from which a first cDNA library is derived, but not displayed by a cell or individual from which a plurality of additional cDNA libraries is derived, comprising:

(a) hybridizing insert DNA from each cDNA library with itself;

(b) contacting each separate population of DNA hybridized in step (a) individually with a first immobilized mismatch binding protein;

(c) separating unbound DNA from bound DNA contacted in step (b);

(d) labeling each separate population of unbound DNA separated in step (c) with a distinguishable label capable of binding a partner molecule immobilized on a substrate;

(e) hybridizing DNA labeled in step (d);

(f) contacting DNA hybridized in step (e) with a second immobilized mismatch binding protein; and (g) separating unbound DNA from bound DNA contacted in step (f), which DNA separated in step (g) encodes one or more identified alleles underlying the defined phenotype.

38. A method for identifying one or more alleles underlying a defined phenotype displayed by a cell or individual from which a first cDNA library is derived, but not displayed by a cell or individual from which a plurality of additional cDNA libraries is derived, comprising:

(a) amplifying insert DNA from each cDNA library by polymerase chain reaction;

(b) hybridizing DNA amplified from each library in step (a) with itself;

(c) contacting DNA from each library hybridized in step (b) individually with a first immobilized mismatch binding protein;

(d) separating unbound DNA from bound DNA contacted in step (c);

(e) amplifying and labeling each separate population of unbound DNA separated in step (d) by polymerase chain reaction using at least one primer having a distinguishable 5'-peptide-label;

(f) hybridizing DNA amplified and labeled in step (e);

(g) contacting DNA hybridized in step (f) with a second immobilized mismatch binding protein;

(h) separating unbound DNA from bound DNA contacted in step (g);

(i) releasing bound DNA separated in step (h); and (j) separating DNA released in step (i) into single strands, which DNA separated in step (i) encodes one or more identified alleles underlying the defined phenotype.

39. A method for identifying one or more alleles underlying a defined phenotype comprising the following steps in the order stated:

(a) removing mismatched duplex nucleic acid molecules formed from hybridization within each of a plurality of source populations of cDNAs;

(b) retaining mismatched duplex nucleic acid molecules formed from hybridization among the plurality of source populations; and (c) separating mismatched strands retained in step (b), which separated strands comprise one or more identified alleles underlying the defined phenotype that differ among source populations.

40. The method of claim 1, wherein the plurality of source populations comprises two or more cDNA libraries each labeled with a distinguishable label.

41. The method of claim 39, wherein the plurality of source populations comprises two or more cDNA libraries each labeled with a distinguishable label.

42. The method of claim 39, wherein the plurality of source populations comprises at least one normalized cDNA library.

43. The method of claim 39, wherein the plurality of source populations comprises at least one linearized cDNA library.

44. The method of claim 39, wherein the plurality of source populations comprises two or more cDNA libraries each labeled with a distinguishable label and the hybridization in step (b) is carried out using an excess of labeled DNA from one or more source populations.

45. The method of claim 44, wherein the excess of labeled DNA is a three-fold excess.

46. The method of claim 39, wherein each of the source populations is derived from a cell line.

47. The method of claim 39, wherein the defined phenotype is selected from the group consisting of a plant phenotype, a microorganism phenotype, and a pathologic phenotype.

48. The method of claim 47, wherein the defined phenotype is a pathologic phenotype that is selected from the group consisting of cancer, osteoporosis, obesity, type II diabetes, and a prion-related disease.

49. The method of any one of claims 35–39, which further comprises using the one or more genes or alleles identified to carry out a prognosis or a diagnosis.

50. The method of claim 49, wherein the one or more genes or alleles identified, or an encoded protein thereof, is a target for drug intervention.

51. The method of claim 39, wherein the plurality of source populations is in the range of three to twelve source populations.

52. The method of claim 39, wherein the plurality of source populations is in the range of three to six source populations.

53. The method of claim 39, wherein the plurality of source populations consists of four source populations.

* * * * *

SEQUENCE LISTING

<160> NUMBER OF SEQ ID NOS: 81

<210> SEQ ID NO 1
<211> LENGTH: 329
<212> TYPE: DNA
<213> ORGANISM: Escherichia coli
<220> FEATURE:
<221> NAME/KEY: modified_base
<222> LOCATION: 300
<223> OTHER INFORMATION: n=a, c, g, or t

<400> SEQUENCE: 1

```
gggccaccgc ttcaattttt ggcgtaattg tccgaaaaac ggcatgaatt tgcttagaaa      60
tggctttata tttggcaaaa tcaggggtca gaaagatccc gtctggcgct aaacgccgcg     120
cttctgcgga tcgcatggcc gaatgaatgc caagttggcg cgcgacatag ttcgccgtcg     180
tcaccacccc acgaccccca gtttctgctg gatcacgcga ataattaat ggctggtggc      240
gtaatgccgg attgtcacgc atctcgactt gggcatagaa ggcatcgata tcaacatggn     300
ggaattttac gtgtatcagt tgtcaataa                                        329
```

<210> SEQ ID NO 2
<211> LENGTH: 256
<212> TYPE: DNA
<213> ORGANISM: Escherichia coli

<400> SEQUENCE: 2

```
ccgggcgttt aggcagacgg gatctttctg acccctgatt ttgccaaata taaagccatt      60
tctaagcaaa ttcatgccgt ttttcggaca attacgccaa aaattgagcc ggtggtgatt     120
gatgaggctt acttagatgt gaccgccaat gcgttgtcag gcgcactgct ggccgcacag     180
ttacggcatg acatttatat acacacgaga ttactctagt tcggtgggtg tatcgtatac     240
catactatta gcgatg                                                       256
```

<210> SEQ ID NO 3
<211> LENGTH: 248
<212> TYPE: DNA
<213> ORGANISM: Escherichia coli
<220> FEATURE:
<221> NAME/KEY: modified_base
<222> LOCATION: all "n" positions
<223> OTHER INFORMATION: n=a, c, g, or t

<400> SEQUENCE: 3

```
gggatgaggc ttacttagat gtgaccgaca atgcgttgtc aggcgcaatn ctggccgcac      60
agttacggca tgacatttat aaacaancac gnttaactag ttcggtgggt gtatcgtata     120
acaaactatt agcgaagttg ggatctgant ttaataagcc aaacggtgtg acggtgatta     180
cgncggaaaa ccgcctggnt tttttagntc atttnccgat tggtgaattt cgcggggtcg     240
gtgagaaa                                                                248
```

<210> SEQ ID NO 4
<211> LENGTH: 387
<212> TYPE: DNA
<213> ORGANISM: Escherichia coli

<400> SEQUENCE: 4

```
gccaacttgg cattcattcg gccatgcgat ccgcagaagc gcggcgttta gcgccagacg      60
ggatctttct gacccctgat tttgccaaat ataaagccat ttctaagcaa attcatgccg     120
```

-continued

```
ttttcggac aattacgcca aaaattgaag cggtggccct tgatgaggct tacttagatg        180
tgaccgccaa tgcgttgtca ggcgcactgc tggccgcaca gttacggcat gacatttata        240
tacacacacg attactctag ttcggtgggt gtatcgtata ccatactatt agcgaggttg        300
ggatctgatt taataagcca aacggtgtga cggtgattac gcggaaaacc gcctggtttt        360
ttagtcattt ccgattggtg aatttcg                                            387
```

<210> SEQ ID NO 5
<211> LENGTH: 381
<212> TYPE: DNA
<213> ORGANISM: Escherichia coli

<400> SEQUENCE: 5

```
gccaacttgg cattcattcg gccatgcgat ccgaagcgcg gcgtttaggc agcagacggg         60
atctttctga cccctgattt tgccaaatat aaagccattt ctaagcaaat tcatgccgtt        120
tttcggacaa ttacgccaaa aattgaagcg gtggtgattg atgaggctta cttagatgtg        180
accgccaatg cgttgtcagg cgcaatctgg ccgcacagtt acggcatgac atttataaac        240
aacacgttaa ctagttcggt gggtgtatcg tataacaaac tattagcgaa gttgggatct        300
gatttaataa gccaaacggt gtgacggtga ttacgcggaa aaccgcctgg ttttttagtc        360
atttccgatt ggtgaatttc g                                                  381
```

<210> SEQ ID NO 6
<211> LENGTH: 567
<212> TYPE: DNA
<213> ORGANISM: Escherichia coli

<400> SEQUENCE: 6

```
ttattgacaa ctgatacacg taaaattccc catgttgata tcgatgcctt ctatgcccaa         60
gtcgagatgc gtgacaatcc ggcattacgc caccagccat taattatttc gcgtgatcca        120
gcagaaactg ggggtcgtgg ggtggtgacg acggcgaact atgtcgcgcc aacttggcat        180
tcattcggcc atgcgatccg cagaagcgcc gggcgtttag gcagacggga tctttctgac        240
ccctgatttt gccaaatata aagccatttc taagcaaatt catgccgttt ttcggacaat        300
tacgccaaaa attgagccgg tggtgattga tgaggcttac ttagatgtga ccgccaatgc        360
gttgtcaggc gcactgctgg ccgcacagtt acggcatgac atttataaac aacacgttaa        420
ctagttcggt gggtgtatcg tataacaaac tattagcgaa gttgggatct gatttaataa        480
gccaaacggt gtgacggtga ttacgcggaa aaccgcctgg ttttttagtc atttccgatt        540
ggtgaatttc gcggggtcgg tgagaaa                                            567
```

<210> SEQ ID NO 7
<211> LENGTH: 63
<212> TYPE: PRT
<213> ORGANISM: Escherichia coli

<400> SEQUENCE: 7

Arg Gly Val Val Thr Thr Ala Asn Tyr Val Ala Arg Leu Gly Ile His
1               5                   10                  15

Ser Ala Met Arg Ser Ala Glu Ala Arg Arg Leu Ala Pro Asp Gly Ile
            20                  25                  30

Phe Leu Thr Pro Asp Phe Ala Lys Tyr Lys Ala Ile Ser Lys Gln Ile
        35                  40                  45

His Ala Val Phe Arg Thr Ile Thr Pro Lys Ile Glu Ala Val Ala
    50                  55                  60

-continued

<210> SEQ ID NO 8
<211> LENGTH: 64
<212> TYPE: PRT
<213> ORGANISM: Escherichia coli

<400> SEQUENCE: 8

Arg Gly Val Ile Ser Thr Ala Asn Tyr Pro Ala Arg Lys Phe Gly Val
 1               5                  10                  15

Arg Ser Ala Met Pro Thr Gly Met Ala Leu Lys Leu Cys Pro His Leu
            20                  25                  30

Thr Leu Leu Pro Gly Arg Phe Asp Ala Tyr Lys Glu Ala Ser Asn His
        35                  40                  45

Ile Arg Glu Ile Phe Ser Arg Tyr Thr Ser Arg Ile Glu Pro Leu Ser
    50                  55                  60

<210> SEQ ID NO 9
<211> LENGTH: 4
<212> TYPE: PRT
<213> ORGANISM: Escherichia coli

<400> SEQUENCE: 9

Thr Ala Asn Tyr
 1

<210> SEQ ID NO 10
<211> LENGTH: 29
<212> TYPE: PRT
<213> ORGANISM: Escherichia coli
<220> FEATURE:
<221> NAME/KEY: SITE
<222> LOCATION: 3
<223> OTHER INFORMATION: Xaa=unknown amino acid

<400> SEQUENCE: 10

Lys Phe Xaa His Val Asp Ile Asp Ala Phe Tyr Ala Gln Val Glu Met
 1               5                  10                  15

Arg Asp Asn Pro Ala Leu Arg His Gln Pro Leu Ile Ile
            20                  25

<210> SEQ ID NO 11
<211> LENGTH: 29
<212> TYPE: PRT
<213> ORGANISM: Escherichia coli

<400> SEQUENCE: 11

Lys Ile Ile His Val Asp Met Asp Cys Phe Phe Ala Ala Val Glu Met
 1               5                  10                  15

Arg Asp Asn Pro Ala Leu Arg Asp Ile Pro Ile Ala Ile
            20                  25

<210> SEQ ID NO 12
<211> LENGTH: 10
<212> TYPE: PRT
<213> ORGANISM: Escherichia coli

<400> SEQUENCE: 12

Val Glu Met Arg Asp Asn Pro Ala Leu Arg
 1               5                  10

<210> SEQ ID NO 13
<211> LENGTH: 55

```
<212> TYPE: PRT
<213> ORGANISM: Escherichia coli

<400> SEQUENCE: 13

Arg Gly Val Val Thr Thr Ala Asn Tyr Val Ala Arg Gln Leu Gly Ile
 1               5                  10                  15

His Ser Ala Met Arg Ser Ala Glu Ala Arg Arg Leu Ala Pro Asp Gly
            20                  25                  30

Ile Phe Leu Thr Pro Asp Phe Ala Lys Tyr Lys Ala Ile Ser Lys Gln
        35                  40                  45

Ile His Ala Val Phe Arg Thr
    50                  55

<210> SEQ ID NO 14
<211> LENGTH: 55
<212> TYPE: PRT
<213> ORGANISM: Escherichia coli

<400> SEQUENCE: 14

Arg Ser Val Val Ser Thr Cys Asn Tyr Val Ala Arg Ser Tyr Gly Ile
 1               5                  10                  15

Arg Ser Gly Met Ser Ile Leu Lys Ala Leu Glu Leu Cys Pro Asn Ala
            20                  25                  30

Ile Phe Ala His Ser Asn Phe Arg Asn Tyr Arg Lys His Ser Lys Arg
        35                  40                  45

Ile Phe Ser Val Ile Glu Ser
    50                  55

<210> SEQ ID NO 15
<211> LENGTH: 5
<212> TYPE: PRT
<213> ORGANISM: Escherichia coli

<400> SEQUENCE: 15

Asn Tyr Val Ala Arg
 1               5

<210> SEQ ID NO 16
<211> LENGTH: 28
<212> TYPE: PRT
<213> ORGANISM: Escherichia coli
<220> FEATURE:
<221> NAME/KEY: SITE
<222> LOCATION: 2
<223> OTHER INFORMATION: Xaa=unknown amino acid

<400> SEQUENCE: 16

Phe Xaa His Val Asp Ile Asp Ala Phe Tyr Ala Gln Val Glu Met Arg
 1               5                  10                  15

Asp Asn Pro Ala Leu Arg His Gln Pro Leu Ile Ile
            20                  25

<210> SEQ ID NO 17
<211> LENGTH: 28
<212> TYPE: PRT
<213> ORGANISM: Escherichia coli

<400> SEQUENCE: 17

Phe Leu Tyr Phe Asp Phe Asp Ala Phe Phe Ala Ser Val Glu Glu Leu
 1               5                  10                  15

Glu Asn Pro Glu Leu Val Asn Gln Pro Leu Ile Val
            20                  25
```

```
<210> SEQ ID NO 18
<211> LENGTH: 4
<212> TYPE: PRT
<213> ORGANISM: Escherichia coli

<400> SEQUENCE: 18

Gln Pro Leu Ile
  1

<210> SEQ ID NO 19
<211> LENGTH: 34
<212> TYPE: PRT
<213> ORGANISM: Escherichia coli

<400> SEQUENCE: 19

Val Asp Ile Asp Ala Phe Tyr Ala Gln Val Glu Met Arg Asp Asn Pro
  1               5                  10                  15

Ala Leu Arg His Gln Pro Leu Ile Ile Ser Arg Asp Pro Ala Glu Thr
             20                  25                  30

Gly Gly

<210> SEQ ID NO 20
<211> LENGTH: 34
<212> TYPE: PRT
<213> ORGANISM: Escherichia coli

<400> SEQUENCE: 20

Val Asp Met Gln Ser Phe Tyr Ala Ser Val Glu Lys Ala Glu Asn Pro
  1               5                  10                  15

His Leu Lys Asn Arg Pro Val Ile Val Ser Gly Asp Pro Glu Lys Arg
             20                  25                  30

Gly Gly

<210> SEQ ID NO 21
<211> LENGTH: 59
<212> TYPE: PRT
<213> ORGANISM: Escherichia coli

<400> SEQUENCE: 21

Gly Val Val Thr Thr Ala Asn Tyr Val Ala Arg Gln Leu Gly Ile His
  1               5                  10                  15

Ser Ala Met Arg Ser Ala Glu Ala Arg Arg Leu Ala Pro Asp Gly Ile
             20                  25                  30

Phe Leu Thr Pro Phe Ala Lys Tyr Lys Ala Ile Ser Lys Gln Ile His
         35                  40                  45

Ala Val Phe Arg Thr Ile Thr Pro Lys Ile Glu
     50                  55

<210> SEQ ID NO 22
<211> LENGTH: 60
<212> TYPE: PRT
<213> ORGANISM: Escherichia coli

<400> SEQUENCE: 22

Gly Val Val Leu Ala Ala Cys Pro Leu Ala Lys Gln Lys Gly Val Val
  1               5                  10                  15

Asn Ala Ser Arg Leu Trp Glu Ala Gln Glu Lys Cys Pro Glu Ala Val
             20                  25                  30

Val Leu Arg Pro Arg Met Gln Arg Tyr Ile Asp Val Ser Leu Gln Ile
```

```
            35                  40                  45
Thr Ala Ile Leu Glu Glu Tyr Thr Asp Leu Val Glu
        50                  55                  60

<210> SEQ ID NO 23
<211> LENGTH: 60
<212> TYPE: PRT
<213> ORGANISM: Escherichia coli

<400> SEQUENCE: 23

Arg Gly Val Val Thr Thr Ala Asn Tyr Val Ala Arg Gln Leu Gly Ile
 1               5                  10                  15

His Ser Ala Met Arg Ser Ala Glu Ala Arg Arg Leu Ala Pro Asp Gly
            20                  25                  30

Ile Phe Leu Thr Pro Asp Phe Ala Lys Tyr Lys Ala Ile Ser Lys Gln
        35                  40                  45

Ile His Ala Val Phe Arg Thr Ile Thr Pro Lys Ile
    50                  55                  60

<210> SEQ ID NO 24
<211> LENGTH: 60
<212> TYPE: PRT
<213> ORGANISM: Escherichia coli

<400> SEQUENCE: 24

Lys Gly Ile Val Val Thr Cys Ser Tyr Glu Ala Arg Ala Arg Gly Val
 1               5                  10                  15

Lys Thr Thr Met Pro Val Trp Gln Ala Lys Arg His Cys Pro Glu Leu
            20                  25                  30

Ile Val Leu Pro Pro Asn Phe Asp Arg Tyr Arg Asn Ser Ser Arg Ala
        35                  40                  45

Met Phe Thr Ile Leu Arg Glu Tyr Thr Asp Leu Val
    50                  55                  60

<210> SEQ ID NO 25
<211> LENGTH: 35
<212> TYPE: PRT
<213> ORGANISM: Escherichia coli

<400> SEQUENCE: 25

Ile Phe Leu Tyr Lys Ala Ile Ser Lys Gln Ile His Ala Val Phe Arg
 1               5                  10                  15

Thr Ile Thr Pro Lys Ile Glu Pro Val Val Ile Asp Glu Ala Tyr Leu
            20                  25                  30

Asp Val Thr
        35

<210> SEQ ID NO 26
<211> LENGTH: 50
<212> TYPE: PRT
<213> ORGANISM: Escherichia coli

<400> SEQUENCE: 26

Ile Val Leu Pro Pro Asn Phe Asp Arg Tyr Arg Asn Ser Ser Arg Ala
 1               5                  10                  15

Met Phe Thr Ile Leu Arg Glu Tyr Thr Asp Leu Val Glu Pro Val Ser
            20                  25                  30

Ile Asp Glu Gly Tyr Met Asp Met Thr Asp Thr Pro Tyr Ser Ser Arg
        35                  40                  45
```

Ala Leu
    50

<210> SEQ ID NO 27
<211> LENGTH: 35
<212> TYPE: PRT
<213> ORGANISM: Escherichia coli

<400> SEQUENCE: 27

Phe Ala Lys Tyr Lys Ala Ile Ser Lys Gln Ile His Ala Val Phe Arg
 1               5                  10                  15

Thr Ile Thr Pro Lys Ile Glu Pro Val Val Ile Asp Glu Ala Tyr Leu
            20                  25                  30

Asp Val Thr
        35

<210> SEQ ID NO 28
<211> LENGTH: 35
<212> TYPE: PRT
<213> ORGANISM: Escherichia coli

<400> SEQUENCE: 28

Phe Asp Ala Tyr Lys Glu Ala Ser Asn His Ile Arg Glu Ile Phe Ser
 1               5                  10                  15

Arg Tyr Thr Ser Arg Ile Glu Pro Leu Ser Leu Asp Glu Ala Tyr Leu
            20                  25                  30

Asp Val Thr
        35

<210> SEQ ID NO 29
<211> LENGTH: 8
<212> TYPE: PRT
<213> ORGANISM: Escherichia coli

<400> SEQUENCE: 29

Asp Glu Ala Tyr Leu Asp Val Thr
 1               5

<210> SEQ ID NO 30
<211> LENGTH: 69
<212> TYPE: PRT
<213> ORGANISM: Escherichia coli
<220> FEATURE:
<221> NAME/KEY: SITE
<222> LOCATION: all "Xaa" positions
<223> OTHER INFORMATION: Xaa=unknown amino acid

<400> SEQUENCE: 30

Ser Gly Ala Xaa Leu Ala Ala Gly Leu Arg His Asp Ile Tyr Lys Gln
 1               5                  10                  15

Xaa Arg Leu Thr Ser Ser Val Gly Val Ser Tyr Asn Lys Leu Leu Ala
            20                  25                  30

Lys Leu Gly Ser Xaa Phe Asn Lys Pro Asn Gly Val Thr Val Ile Thr
        35                  40                  45

Xaa Glu Asn Arg Leu Xaa Phe Leu Xaa His Xaa Pro Ile Gly Glu Phe
    50                  55                  60

Arg Gly Val Gly Glu
 65

<210> SEQ ID NO 31
<211> LENGTH: 69
<212> TYPE: PRT

<213> ORGANISM: Escherichia coli

<400> SEQUENCE: 31

Ser Ala Thr Leu Ile Ala Gln Glu Ile Arg Gln Thr Ile Phe Asn Glu
1               5                   10                  15

Leu Gln Leu Thr Ala Ser Ala Gly Val Ala Pro Val Lys Phe Leu Ala
            20                  25                  30

Lys Ile Ala Ser Asp Met Asn Lys Pro Asn Gly Gln Phe Val Ile Thr
        35                  40                  45

Pro Ala Glu Val Pro Ala Phe Leu Gln Thr Leu Pro Leu Ala Lys Ile
    50                  55                  60

Pro Gly Val Gly Lys
 65

<210> SEQ ID NO 32
<211> LENGTH: 5
<212> TYPE: PRT
<213> ORGANISM: Escherichia coli

<400> SEQUENCE: 32

Asn Lys Pro Asn Gly
1               5

<210> SEQ ID NO 33
<211> LENGTH: 10
<212> TYPE: PRT
<213> ORGANISM: Escherichia coli

<400> SEQUENCE: 33

Asp Glu Ala Tyr Leu Asp Val Thr Asp Asn
1               5                   10

<210> SEQ ID NO 34
<211> LENGTH: 10
<212> TYPE: PRT
<213> ORGANISM: Escherichia coli

<400> SEQUENCE: 34

Asp Glu Ala Tyr Leu Asp Val Thr Asp Ser
1               5                   10

<210> SEQ ID NO 35
<211> LENGTH: 9
<212> TYPE: PRT
<213> ORGANISM: Escherichia coli

<400> SEQUENCE: 35

Asp Glu Ala Tyr Leu Asp Val Thr Asp
1               5

<210> SEQ ID NO 36
<211> LENGTH: 65
<212> TYPE: PRT
<213> ORGANISM: Escherichia coli
<220> FEATURE:
<221> NAME/KEY: SITE
<222> LOCATION: all "Xaa" positions
<223> OTHER INFORMATION: Xaa=unknown amino acid

<400> SEQUENCE: 36

Ala Ala Gln Leu Arg His Asp Ile Tyr Lys Gln Xaa Arg Leu Thr Ser
1               5                   10                  15

Ser Val Gly Val Ser Tyr Asn Lys Leu Leu Ala Lys Leu Gly Ser Xaa

-continued

```
                    20                  25                  30
Phe Asn Lys Pro Asn Gly Val Thr Val Ile Thr Xaa Glu Asn Arg Ile
            35                  40                  45
Xaa Phe Leu Xaa His Xaa Pro Ile Gly Glu Phe Arg Gly Val Gly Glu
        50                  55                  60
Lys
 65

<210> SEQ ID NO 37
<211> LENGTH: 65
<212> TYPE: PRT
<213> ORGANISM: Escherichia coli

<400> SEQUENCE: 37

Ala Lys Glu Ile Gln Ser Arg Leu Gln Lys Glu Leu Leu Pro Ser
  1               5                  10                  15
Ser Ile Gly Ile Ala Pro Asn Lys Phe Leu Ala Lys Met Ala Ser Asp
            20                  25                  30
Met Lys Lys Pro Leu Gly Ile Thr Ile Leu Arg Lys Arg Gln Val Pro
        35                  40                  45
Asp Ile Leu Trp Pro Leu Pro Val Gly Glu Met His Gly Val Gly Lys
    50                  55                  60
Lys
 65

<210> SEQ ID NO 38
<211> LENGTH: 17
<212> TYPE: PRT
<213> ORGANISM: Escherichia coli
<220> FEATURE:
<221> NAME/KEY: SITE
<222> LOCATION: 16
<223> OTHER INFORMATION: Xaa=unknown amino acid

<400> SEQUENCE: 38

Asp Glu Ala Tyr Leu Asp Val Thr Asp Asn Ala Leu Ser Gly Ala Xaa
  1               5                  10                  15
Leu

<210> SEQ ID NO 39
<211> LENGTH: 17
<212> TYPE: PRT
<213> ORGANISM: Escherichia coli

<400> SEQUENCE: 39

Asp Glu Gly Tyr Met Asp Met Thr Asp Thr Pro Tyr Ser Ser Arg Ala
  1               5                  10                  15
Leu

<210> SEQ ID NO 40
<211> LENGTH: 66
<212> TYPE: PRT
<213> ORGANISM: Escherichia coli
<220> FEATURE:
<221> NAME/KEY: SITE
<222> LOCATION: all "Xaa" positions
<223> OTHER INFORMATION: Xaa=unknown amino acid

<400> SEQUENCE: 40

Leu Ala Ala Gln Leu Arg His Asp Ile Tyr Lys Gln Xaa Arg Leu Thr
  1               5                  10                  15
Ser Ser Val Gly Val Ser Tyr Asn Lys Leu Leu Ala Lys Leu Gly Ser
```

```
                   20                  25                  30

Xaa Phe Asn Lys Pro Asn Gly Val Thr Val Ile Thr Xaa Glu Asn Arg
             35                  40                  45

Leu Xaa Phe Leu Xaa Glu Xaa Pro Ile Gly Glu Phe Arg Gly Val Gly
     50                  55                  60

Glu Lys
 65

<210> SEQ ID NO 41
<211> LENGTH: 66
<212> TYPE: PRT
<213> ORGANISM: Escherichia coli

<400> SEQUENCE: 41

Ile Ala Lys Lys Ile Lys Asn Phe Val Phe Gln Asn Leu Arg Ile Lys
  1               5                  10                  15

Ile Ser Ile Gly Ile Ser Asp His Phe Leu Ile Ala Lys Ile Phe Ser
                 20                  25                  30

Asn Gln Ala Lys Pro Phe Gly Ile Lys Ser Cys Ser Val Lys Asp Ile
             35                  40                  45

Lys Lys Lys Leu Trp Pro Leu Pro Ile Thr Glu Ile Pro Gly Ile Gly
     50                  55                  60

Glu Lys
 65

<210> SEQ ID NO 42
<211> LENGTH: 61
<212> TYPE: PRT
<213> ORGANISM: Escherichia coli

<400> SEQUENCE: 42

Gln Leu Gly Ile His Ser Ala Met Arg Ser Ala Glu Ala Arg Arg Leu
  1               5                  10                  15

Ala Pro Asp Gly Ile Phe Leu Thr Pro Asp Phe Ala Lys Tyr Lys Ala
                 20                  25                  30

Ile Ser Lys Gln Ile His Ala Val Phe Arg Thr Ile Thr Pro Lys Ile
             35                  40                  45

Glu Ala Val Ala Leu Asp Glu Ala Tyr Leu Asp Val Thr
     50                  55                  60

<210> SEQ ID NO 43
<211> LENGTH: 61
<212> TYPE: PRT
<213> ORGANISM: Escherichia coli

<400> SEQUENCE: 43

Lys Phe Gly Val Arg Ser Ala Met Pro Thr Gly Met Ala Leu Lys Leu
  1               5                  10                  15

Cys Pro His Leu Thr Leu Leu Pro Gly Arg Phe Asp Ala Tyr Lys Glu
                 20                  25                  30

Ala Ser Asn His Ile Arg Glu Ile Phe Ser Arg Tyr Thr Ser Arg Ile
             35                  40                  45

Glu Pro Leu Ser Leu Asp Glu Ala Tyr Leu Asp Val Thr
     50                  55                  60

<210> SEQ ID NO 44
<211> LENGTH: 9
<212> TYPE: PRT
<213> ORGANISM: Escherichia coli
```

```
<400> SEQUENCE: 44

Leu Asp Glu Ala Tyr Leu Asp Val Thr
 1               5

<210> SEQ ID NO 45
<211> LENGTH: 39
<212> TYPE: PRT
<213> ORGANISM: Escherichia coli

<400> SEQUENCE: 45

Gln Leu Arg His Asp Ile Tyr Ile His Thr Arg Leu Leu Phe Gly Gly
 1               5                  10                  15

Cys Ile Val Tyr His Thr Ile Ser Glu Val Gly Ile Phe Asn Lys Pro
            20                  25                  30

Asn Gly Val Thr Val Ile Thr
        35

<210> SEQ ID NO 46
<211> LENGTH: 41
<212> TYPE: PRT
<213> ORGANISM: Escherichia coli

<400> SEQUENCE: 46

Glu Ile Arg Gln Thr Ile Phe Asn Glu Leu Gln Leu Thr Ala Ser Ala
 1               5                  10                  15

Gly Val Ala Pro Val Lys Phe Leu Ala Lys Ile Ala Ser Asp Met Asn
            20                  25                  30

Lys Pro Asn Gly Gln Phe Val Ile Thr
        35                  40

<210> SEQ ID NO 47
<211> LENGTH: 5
<212> TYPE: PRT
<213> ORGANISM: Escherichia coli

<400> SEQUENCE: 47

Asn Lys Pro Asn Gly
 1               5

<210> SEQ ID NO 48
<211> LENGTH: 38
<212> TYPE: PRT
<213> ORGANISM: Escherichia coli

<400> SEQUENCE: 48

Ser Gly Ala Leu Leu Ala His Ser Tyr Gly Met Thr Phe Ile Tyr Thr
 1               5                  10                  15

His Asp Tyr Ser Ser Ser Val Gly Val Ser Tyr Thr Ile Leu Leu Ala
            20                  25                  30

Lys Leu Gly Ser Asp Leu
        35

<210> SEQ ID NO 49
<211> LENGTH: 38
<212> TYPE: PRT
<213> ORGANISM: Escherichia coli

<400> SEQUENCE: 49

Ser Ala Thr Leu Ile Ala Gln Glu Ile Arg Gln Thr Ile Phe Asn Glu
 1               5                  10                  15
```

-continued

Leu Gln Leu Thr Ala Ser Ala Gly Val Ala Pro Val Lys Phe Leu Ala
            20                  25                  30
Lys Ile Ala Ser Asp Met
            35

<210> SEQ ID NO 50
<211> LENGTH: 68
<212> TYPE: PRT
<213> ORGANISM: Escherichia coli

<400> SEQUENCE: 50

Gly Ile His Ser Ala Met Arg Ser Ala Glu Ala Arg Arg Leu Ala Pro
 1               5                  10                  15
Asp Gly Ile Phe Leu Thr Pro Asp Phe Ala Lys Tyr Lys Ala Ile Ser
            20                  25                  30
Lys Gln Ile Asx Ala Val Phe Arg Thr Ile Thr Pro Lys Ile Glu Ala
            35                  40                  45
Val Ala Leu Asp Glu Ala Tyr Leu Asp Val Thr Ala Asn Ala Leu Ser
        50                  55                  60
Gly Ala Leu Leu
65

<210> SEQ ID NO 51
<211> LENGTH: 68
<212> TYPE: PRT
<213> ORGANISM: Escherichia coli

<400> SEQUENCE: 51

Gly Val Lys Thr Thr Met Pro Val Trp Gln Ala Lys Arg His Cys Pro
 1               5                  10                  15
Glu Leu Ile Val Leu Pro Pro Asn Phe Asp Arg Tyr Arg Asn Ser Ser
            20                  25                  30
Arg Ala Met Phe Thr Ile Leu Arg Glu Tyr Thr Asp Leu Val Glu Pro
            35                  40                  45
Val Ser Ile Asp Glu Gly Tyr Met Asp Met Thr Asp Thr Pro Tyr Ser
        50                  55                  60
Ser Arg Ala Leu
65

<210> SEQ ID NO 52
<211> LENGTH: 18
<212> TYPE: PRT
<213> ORGANISM: Escherichia coli

<400> SEQUENCE: 52

Ser Ser Val Gly Val Ser Tyr Thr Ile Leu Leu Ala Lys Leu Gly Ser
 1               5                  10                  15
Asp Leu

<210> SEQ ID NO 53
<211> LENGTH: 18
<212> TYPE: PRT
<213> ORGANISM: Escherichia coli

<400> SEQUENCE: 53

Ser Ser Ile Gly Ile Ala Pro Asn Lys Phe Leu Ala Lys Met Ala Ser
 1               5                  10                  15
Asp Met

```
<210> SEQ ID NO 54
<211> LENGTH: 61
<212> TYPE: PRT
<213> ORGANISM: Escherichia coli

<400> SEQUENCE: 54

Gln Leu Gly Ile His Ser Ala Met Arg Ser Ala Glu Ala Arg Arg Leu
 1               5                  10                  15

Ala Pro Asp Gly Ile Phe Leu Thr Pro Asp Phe Ala Lys Tyr Lys Ala
            20                  25                  30

Ile Ser Lys Gln Ile His Ala Val Phe Arg Thr Ile Thr Pro Lys Ile
        35                  40                  45

Glu Ala Val Ala Leu Asp Glu Ala Tyr Leu Asp Val Thr
    50                  55                  60

<210> SEQ ID NO 55
<211> LENGTH: 61
<212> TYPE: PRT
<213> ORGANISM: Escherichia coli

<400> SEQUENCE: 55

Lys Leu Gly Val Lys Ala Gly Met Pro Ile Ile Lys Ala Met Gln Ile
 1               5                  10                  15

Ala Pro Ser Ala Ile Tyr Val Pro Met Arg Lys Pro Ile Tyr Glu Ala
            20                  25                  30

Phe Ser Asn Arg Ile Met Asn Leu Leu Asn Lys His Ala Asp Lys Ile
        35                  40                  45

Glu Val Ala Ser Ile Asp Glu Ala Tyr Leu Asp Val Thr
    50                  55                  60

<210> SEQ ID NO 56
<211> LENGTH: 8
<212> TYPE: PRT
<213> ORGANISM: Escherichia coli

<400> SEQUENCE: 56

Asp Glu Ala Tyr Leu Asp Val Thr
 1               5

<210> SEQ ID NO 57
<211> LENGTH: 43
<212> TYPE: PRT
<213> ORGANISM: Escherichia coli

<400> SEQUENCE: 57

Val Thr Ala Asn Ala Leu Ser Gly Ala Leu Leu Ala His Ser Tyr Gly
 1               5                  10                  15

Met Thr Phe Ile Tyr Thr His Asp Tyr Ser Ser Ser Val Gly Val Ser
            20                  25                  30

Tyr Thr Ile Leu Leu Ala Lys Leu Gly Ser Asp
        35                  40

<210> SEQ ID NO 58
<211> LENGTH: 43
<212> TYPE: PRT
<213> ORGANISM: Escherichia coli

<400> SEQUENCE: 58

Val Glu Gly Asn Phe Glu Asn Gly Ile Glu Leu Ala Arg Lys Ile Lys
 1               5                  10                  15

Gln Glu Ile Leu Glu Lys Glu Lys Ile Thr Val Thr Val Gly Val Ala
```

-continued

```
                    20                  25                  30
Pro Asn Lys Ile Leu Ala Lys Ile Ile Ala Asp
            35                  40

<210> SEQ ID NO 59
<211> LENGTH: 20
<212> TYPE: PRT
<213> ORGANISM: Escherichia coli

<400> SEQUENCE: 59

Leu Thr Ser Ser Val Gly Val Ser Tyr Asn Lys Leu Leu Ala Lys Leu
 1               5                  10                  15

Gly Ser Asp Leu
            20

<210> SEQ ID NO 60
<211> LENGTH: 20
<212> TYPE: PRT
<213> ORGANISM: Escherichia coli

<400> SEQUENCE: 60

Leu Pro Ser Ser Ile Gly Ile Ala Pro Asn Lys Phe Leu Ala Lys Met
 1               5                  10                  15

Ala Ser Asp Met
            20

<210> SEQ ID NO 61
<211> LENGTH: 35
<212> TYPE: PRT
<213> ORGANISM: Escherichia coli

<400> SEQUENCE: 61

Phe Ala Lys Tyr Lys Ala Ile Ser Lys Gln Ile His Ala Val Phe Arg
 1               5                  10                  15

Thr Ile Thr Pro Lys Ile Glu Ala Val Val Ile Asp Glu Ala Tyr Leu
            20                  25                  30

Asp Val Thr
        35

<210> SEQ ID NO 62
<211> LENGTH: 35
<212> TYPE: PRT
<213> ORGANISM: Escherichia coli

<400> SEQUENCE: 62

Phe Asp Ala Tyr Lys Glu Ala Ser Asn His Ile Arg Glu Ile Phe Ser
 1               5                  10                  15

Arg Tyr Thr Ser Arg Ile Glu Pro Leu Ser Ile Asp Glu Ala Tyr Leu
            20                  25                  30

Asp Val Thr
        35

<210> SEQ ID NO 63
<211> LENGTH: 8
<212> TYPE: PRT
<213> ORGANISM: Escherichia coli

<400> SEQUENCE: 63

Asp Glu Ala Tyr Leu Asp Val Thr
 1               5
```

```
<210> SEQ ID NO 64
<211> LENGTH: 20
<212> TYPE: PRT
<213> ORGANISM: Escherichia coli

<400> SEQUENCE: 64

Leu Thr Ser Ser Val Gly Val Ser Tyr Asn Lys Leu Ala Lys Leu
 1               5                  10                  15

Gly Ser Asp Leu
            20

<210> SEQ ID NO 65
<211> LENGTH: 20
<212> TYPE: PRT
<213> ORGANISM: Escherichia coli

<400> SEQUENCE: 65

Leu Thr Ala Ser Ala Gly Val Ala Pro Val Lys Phe Leu Ala Lys Ile
 1               5                  10                  15

Ala Ser Asp Met
            20

<210> SEQ ID NO 66
<211> LENGTH: 17
<212> TYPE: PRT
<213> ORGANISM: Escherichia coli

<400> SEQUENCE: 66

Ile Ser Glu Val Gly Ile Phe Asn Lys Pro Asn Gly Val Thr Val Ile
 1               5                  10                  15

Thr

SEQ ID NO 67
<211> LENGTH: 18
<212> TYPE: PRT
<213> ORGANISM: Escherichia coli

<400> SEQUENCE: 67

Leu Ala Lys Ile Ala Ser Asp Met Asn Lys Pro Asn Gly Gln Phe Val
 1               5                  10                  15

Ile Thr

SEQ ID NO 68
LENGTH: 5

TYPE: PRT
ORGANISM: Escherichia coli

<400> SEQUENCE: 68

Asn Lys Pro Asn Gly
 1               5

<210> SEQ ID NO 69
<211> LENGTH: 41
TYPE: PRT
ORGANISM: Escherichia coli

<400> SEQUENCE: 69

Ile Phe Leu Thr Pro Asp Phe Ala Lys Tyr Lys Ala Ile Ser Lys Gln
 1               5                  10                  15

Ile His Ala Val Phe Arg Thr Ile Thr Pro Lys Ile Glu Ala Val Val
```

```
                          20                  25                  30

Ile Asp Glu Ala Tyr Leu Asp Val Thr
            35                  40

SEQ ID NO 70
LENGTH: 41
<212> TYPE: PRT
<213> ORGANISM: Escherichia coli

<400> SEQUENCE: 70

Ile Val Leu Pro Pro Asn Phe Asp Arg Tyr Arg Asn Ser Ser Arg Ala
 1               5                  10                  15

Met Phe Thr Ile Leu Arg Glu Tyr Thr Asp Leu Val Glu Pro Val Ser
            20                  25                  30

Ile Asp Glu Gly Tyr Met Asp Met Thr
            35                  40

<210> SEQ ID NO 71
<211> LENGTH: 11
<212> TYPE: PRT
<213> ORGANISM: Oryctolagus cuniculus

<400> SEQUENCE: 71

Lys Phe Ser Arg Glu Lys Lys Ala Ala Lys Thr
 1               5                  10

<210> SEQ ID NO 72
<211> LENGTH: 11
<212> TYPE: PRT
<213> ORGANISM: Oryctolagus cuniculus

<400> SEQUENCE: 72

Asp Gln Lys Arg Tyr His Glu Asp Ile Phe Gly
 1               5                  10

<210> SEQ ID NO 73
<211> LENGTH: 15
<212> TYPE: PRT
<213> ORGANISM: Oryctolagus cuniculus

<400> SEQUENCE: 73

Asp Leu Lys Glu Glu Lys Asp Ile Asn Asn Asn Val Lys Lys Thr
 1               5                  10                  15

<210> SEQ ID NO 74
<211> LENGTH: 9
<212> TYPE: PRT
<213> ORGANISM: Oryctolagus cuniculus

<400> SEQUENCE: 74

Cys Thr Gly Glu Glu Asp Thr Ser Glu
 1               5

<210> SEQ ID NO 75
<211> LENGTH: 11
<212> TYPE: PRT
<213> ORGANISM: Oryctolagus cuniculus

<400> SEQUENCE: 75

Pro Glu Glu Thr Gln Thr Gln Asp Gln Pro Met
 1               5                  10
```

```
<210> SEQ ID NO 76
<211> LENGTH: 13
<212> TYPE: PRT
<213> ORGANISM: Oryctolagus cuniculus

<400> SEQUENCE: 76

Gln Lys Ser Asp Gln Gly Val Glu Gly Pro Gly Ala Thr
 1               5                  10

<210> SEQ ID NO 77
<211> LENGTH: 12
<212> TYPE: PRT
<213> ORGANISM: Oryctolagus cuniculus

<400> SEQUENCE: 77

Asp Ile Gly Gln Ser Ile Lys Lys Phe Ser Lys Val
 1               5                  10

<210> SEQ ID NO 78
<211> LENGTH: 10
<212> TYPE: PRT
<213> ORGANISM: Oryctolagus cuniculus

<400> SEQUENCE: 78

Gln Arg Ala Asp Ser Leu Ser Ser His Leu
 1               5                  10

<210> SEQ ID NO 79
<211> LENGTH: 9
<212> TYPE: PRT
<213> ORGANISM: Oryctolagus cuniculus

<400> SEQUENCE: 79

Tyr Pro Tyr Asp Val Pro Asp Tyr Ala
 1               5

<210> SEQ ID NO 80
<211> LENGTH: 10
<212> TYPE: PRT
<213> ORGANISM: Oryctolagus cuniculus

<400> SEQUENCE: 80

Glu Gln Lys Leu Ile Ser Glu Glu Asp Leu
 1               5                  10

<210> SEQ ID NO 81
<211> LENGTH: 11
<212> TYPE: PRT
<213> ORGANISM: Oryctolagus cuniculus

<400> SEQUENCE: 81

Tyr Thr Asp Ile Glu Met Asn Lys Leu Gly Lys
 1               5                  10
```